United States Patent
Tang et al.

(10) Patent No.: US 11,578,265 B2
(45) Date of Patent: Feb. 14, 2023

(54) AIEGENS FOR CANCER CELL IMAGING

(71) Applicant: THE HONG KONG UNIVERSITY OF SCIENCE AND TECHNOLOGY, Hong Kong (CN)

(72) Inventors: Benzhong Tang, Hong Kong (CN); Xiujuan Shi, Hong Kong (CN); Yee Yung Yu, Hong Kong (CN); Tsz Kin Kwok, Hong Kong (CN); Zheng Zhao, Hong Kong (CN); Pengfei Zhang, Hong Kong (CN); Huifang Su, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 1001 days.

(21) Appl. No.: 16/319,436

(22) PCT Filed: Jul. 21, 2017

(86) PCT No.: PCT/CN2017/093831
§ 371 (c)(1),
(2) Date: Jan. 21, 2019

(87) PCT Pub. No.: WO2018/014865
PCT Pub. Date: Jan. 25, 2018

(65) Prior Publication Data
US 2021/0371735 A1 Dec. 2, 2021

Related U.S. Application Data

(60) Provisional application No. 62/495,029, filed on Aug. 31, 2016, provisional application No. 62/493,902, filed on Jul. 21, 2016.

(51) Int. Cl.
| | | |
|---|---|---|
| *C09K 11/06* | (2006.01) | |
| *C07D 221/14* | (2006.01) | |
| *C07D 213/57* | (2006.01) | |
| *C07D 401/12* | (2006.01) | |
| *C07D 285/14* | (2006.01) | |
| *A61N 5/06* | (2006.01) | |
| *G01N 33/533* | (2006.01) | |
| *G01N 33/58* | (2006.01) | |
| *C07C 211/43* | (2006.01) | |

(52) U.S. Cl.
CPC ............ *C09K 11/06* (2013.01); *A61N 5/06* (2013.01); *G01N 33/533* (2013.01); *G01N 33/582* (2013.01); *C07C 211/43* (2013.01); *C07D 213/57* (2013.01); *C07D 221/14* (2013.01); *C07D 285/14* (2013.01); *C07D 401/12* (2013.01); *C09K 2211/1007* (2013.01); *C09K 2211/1018* (2013.01)

(58) Field of Classification Search
None
See application file for complete search history.

(56) References Cited

U.S. PATENT DOCUMENTS

| | | |
|---|---|---|
| 8,129,111 B2 | 3/2012 | Tang et al. |
| 9,109,155 B2 | 8/2015 | Tang et al. |
| 2014/0255696 A1 | 9/2014 | Tang et al. |

FOREIGN PATENT DOCUMENTS

| | | |
|---|---|---|
| CN | 103788940 A | 5/2014 |
| CN | 103842472 A | 6/2014 |
| CN | 104974745 A | 10/2015 |

OTHER PUBLICATIONS

Hu, Rongrong, et al. "AIE macromolecules: syntheses, structures and functionalities", Chem. Soc. Rev., vol. 43, Apr. 15, 2014, pp. 4494-4562.
Yu, Chris Y.Y., et al., "A photostable AIEgen for nucleolus and mitochondria imaging with organelle-specific emission", Journal of Materials Chemistry B, No. 4, Mar. 11, 2016, pp. 2614-2619.
Hong, Yuning, et al., "Aggregation-induced emission", Chem. Soc. Rev., vol. 40, Jul. 29, 2011, pp. 5361-5388.

*Primary Examiner* — Joseph R Kosack
(74) *Attorney, Agent, or Firm* — Nath, Goldberg & Meyer; Joshua B. Goldberg

(57) ABSTRACT

The present subject matter is directed to a luminogen exhibiting aggregation induced emission, wherein T1, T2, and T3 comprise one or more polyynes as a conjugated bridge. The present subject matter is also directed to an AIEgen comprising a hydrophilic pyridium group as a strong electron-withdrawing group; a piperazine group as an electron-donating group; and a α-Cyanostilbene; wherein the AIEgen exhibits aggregation induced emission. The present subject matter is directed to a method of synthesizing an AIEgen and is further directed to a method of labeling comprising incubating a subject having cells with a conjugate formed by conjugating an AIEgen with an antibody; and selectively labeling desired cells by turn-on imaging, wherein labeling occurs when the desired cells are selectively stained by fluorescent emission of the AIEgen upon degradation of the antibody after cellular internalization of the conjugate through endocytosis.

5 Claims, 37 Drawing Sheets

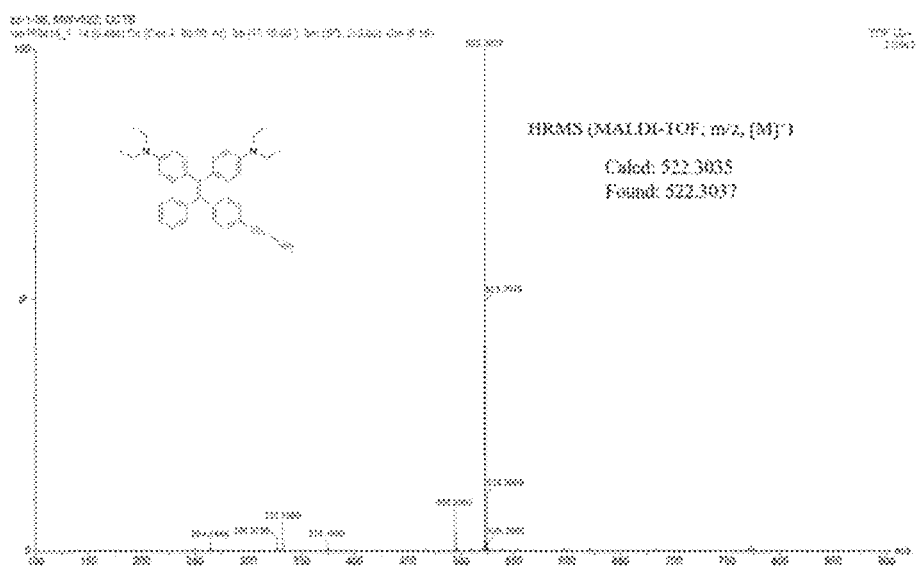
FIG. 2
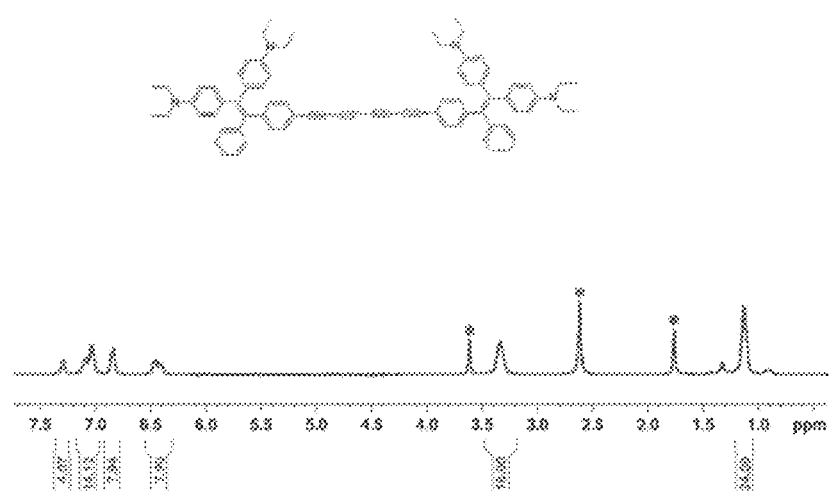
FIG. 3A

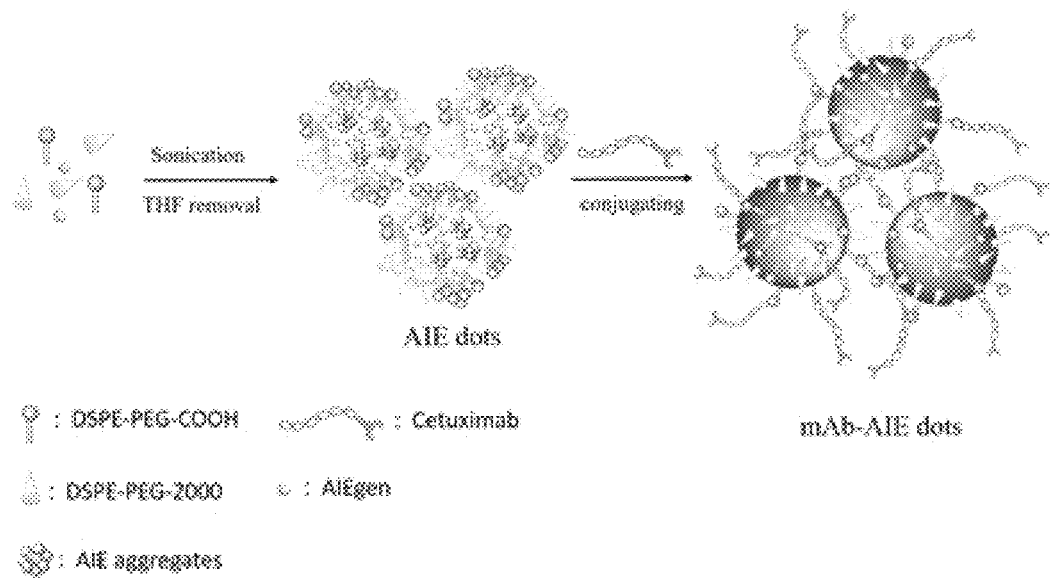
FIG. 8A
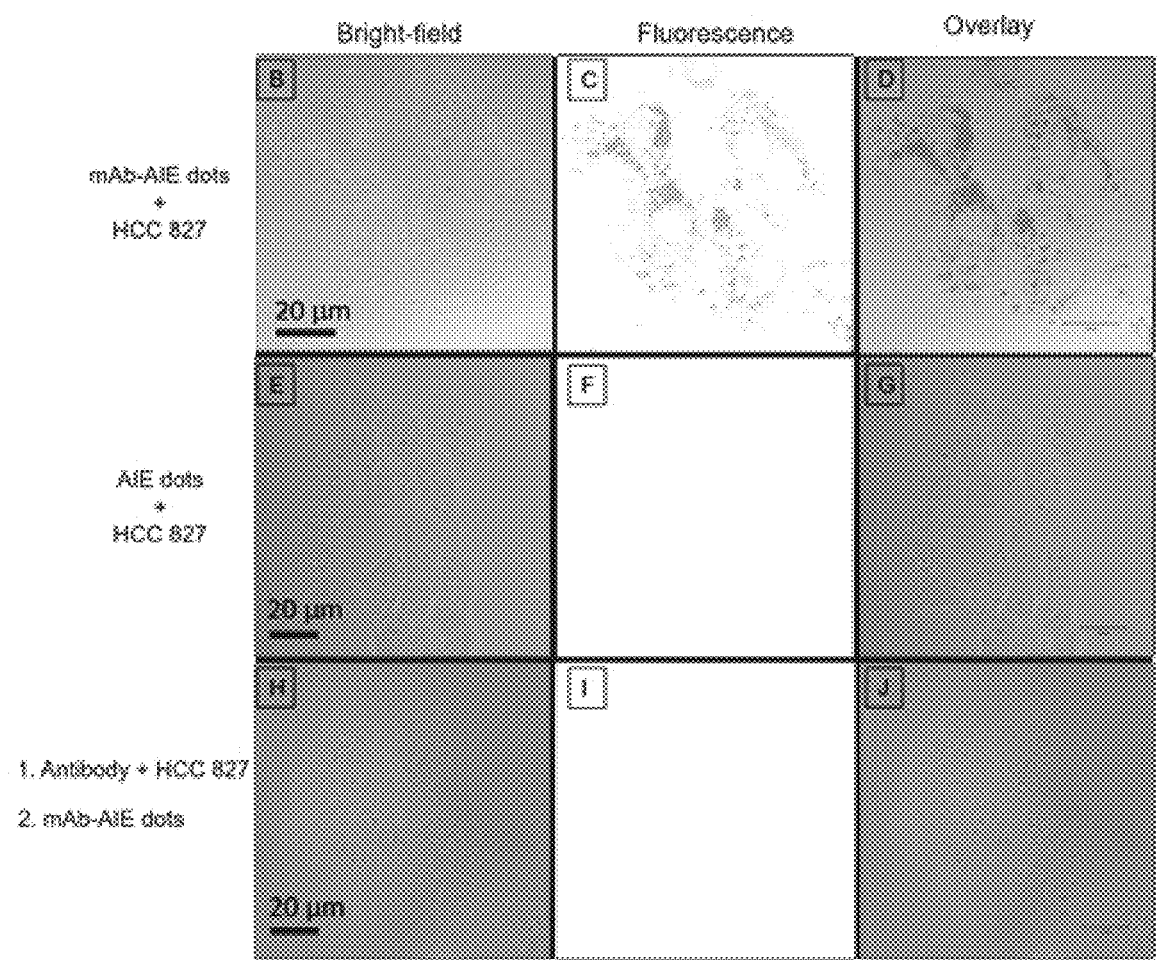
FIG. 8B-J

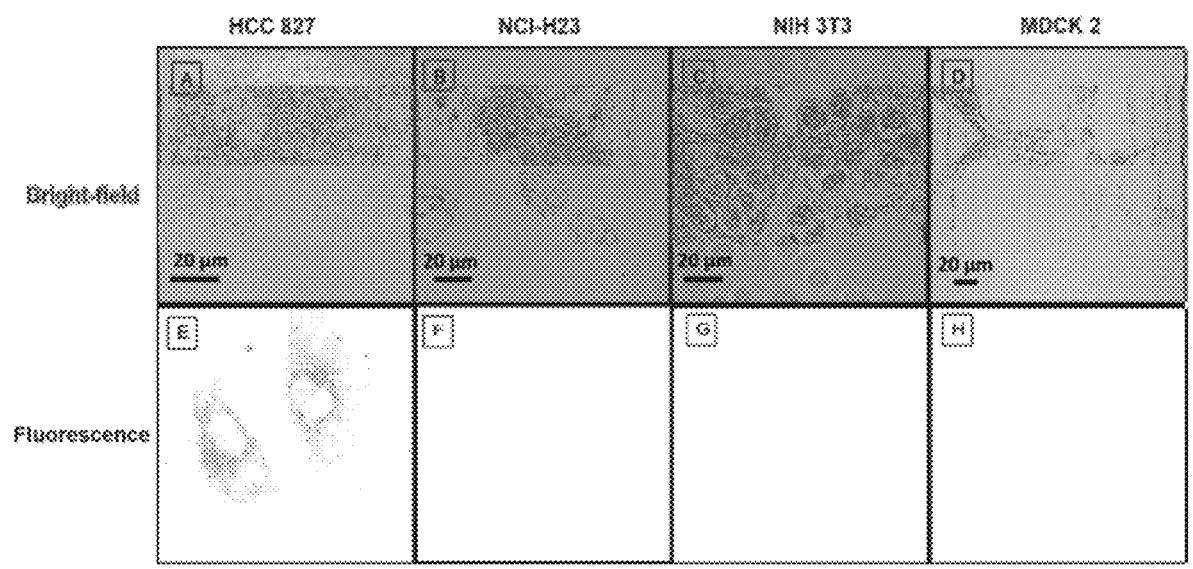
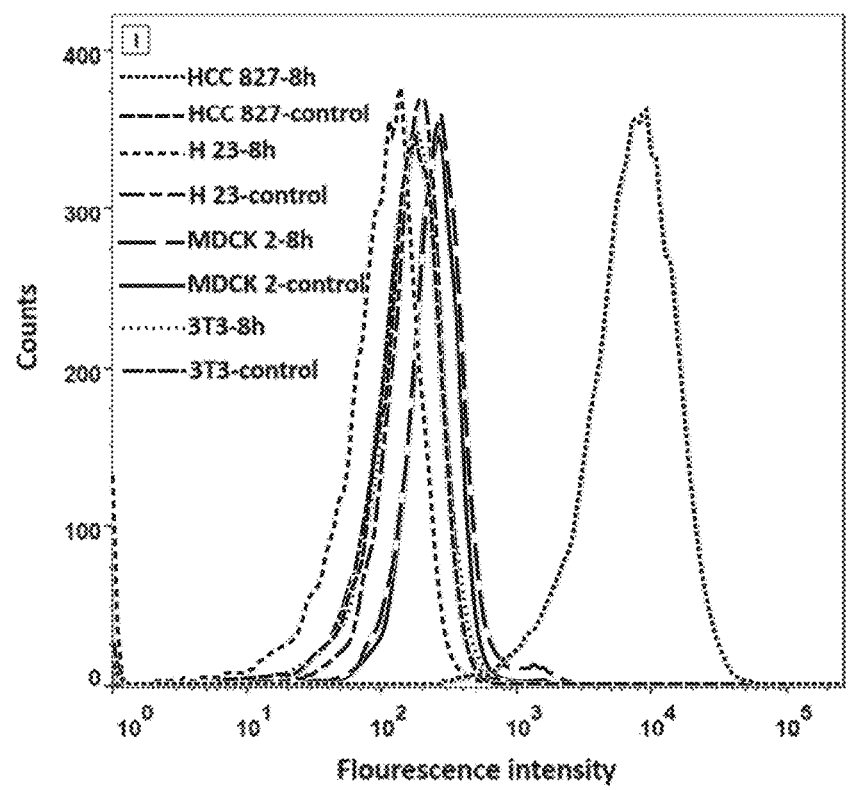
FIG. 9A-I

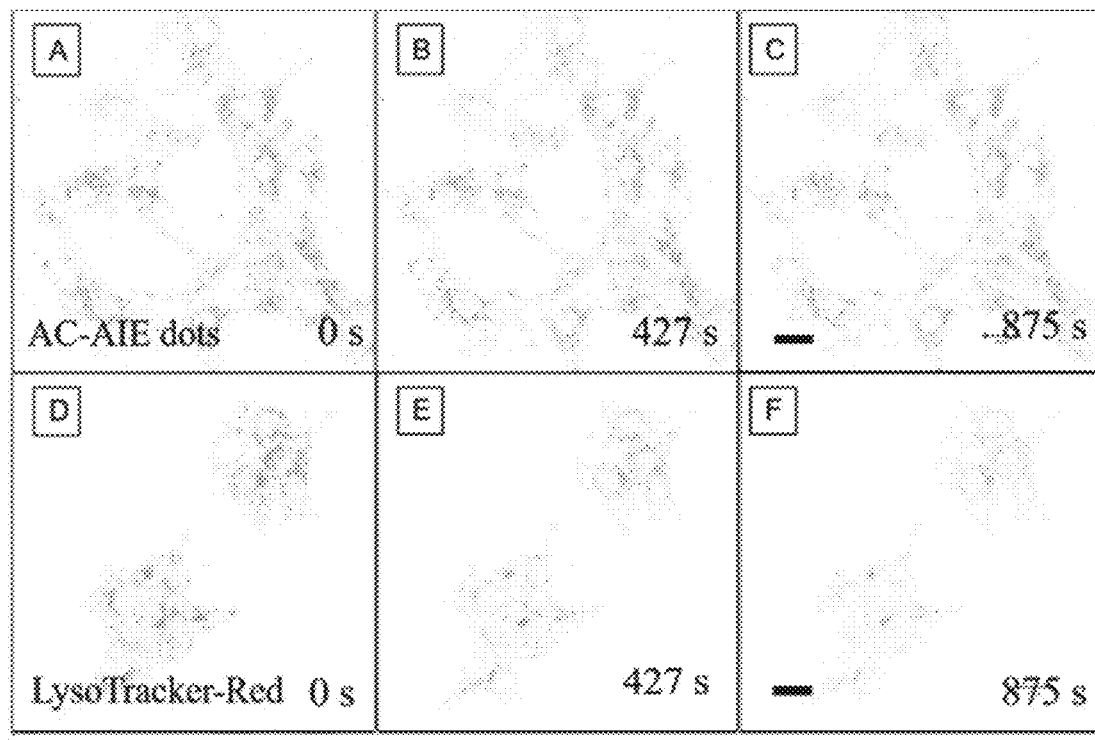
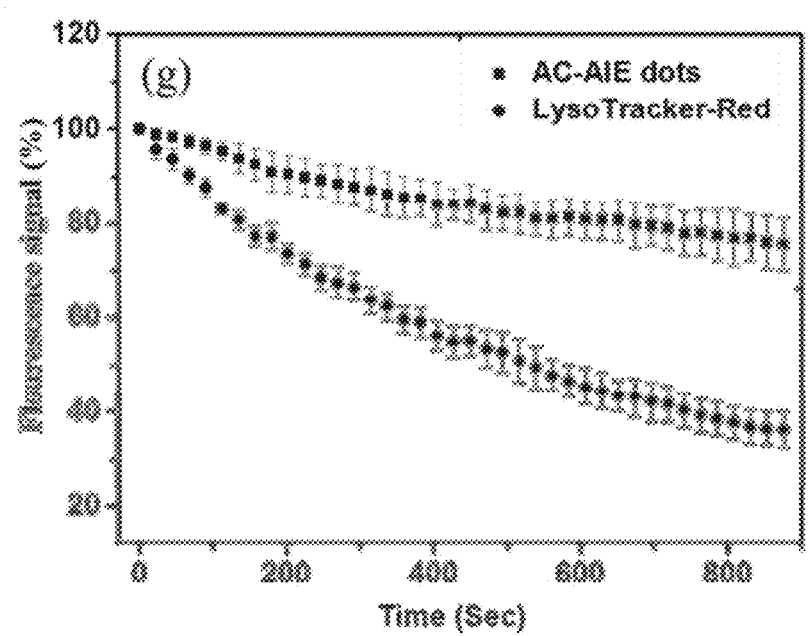
FIG. 10A-G

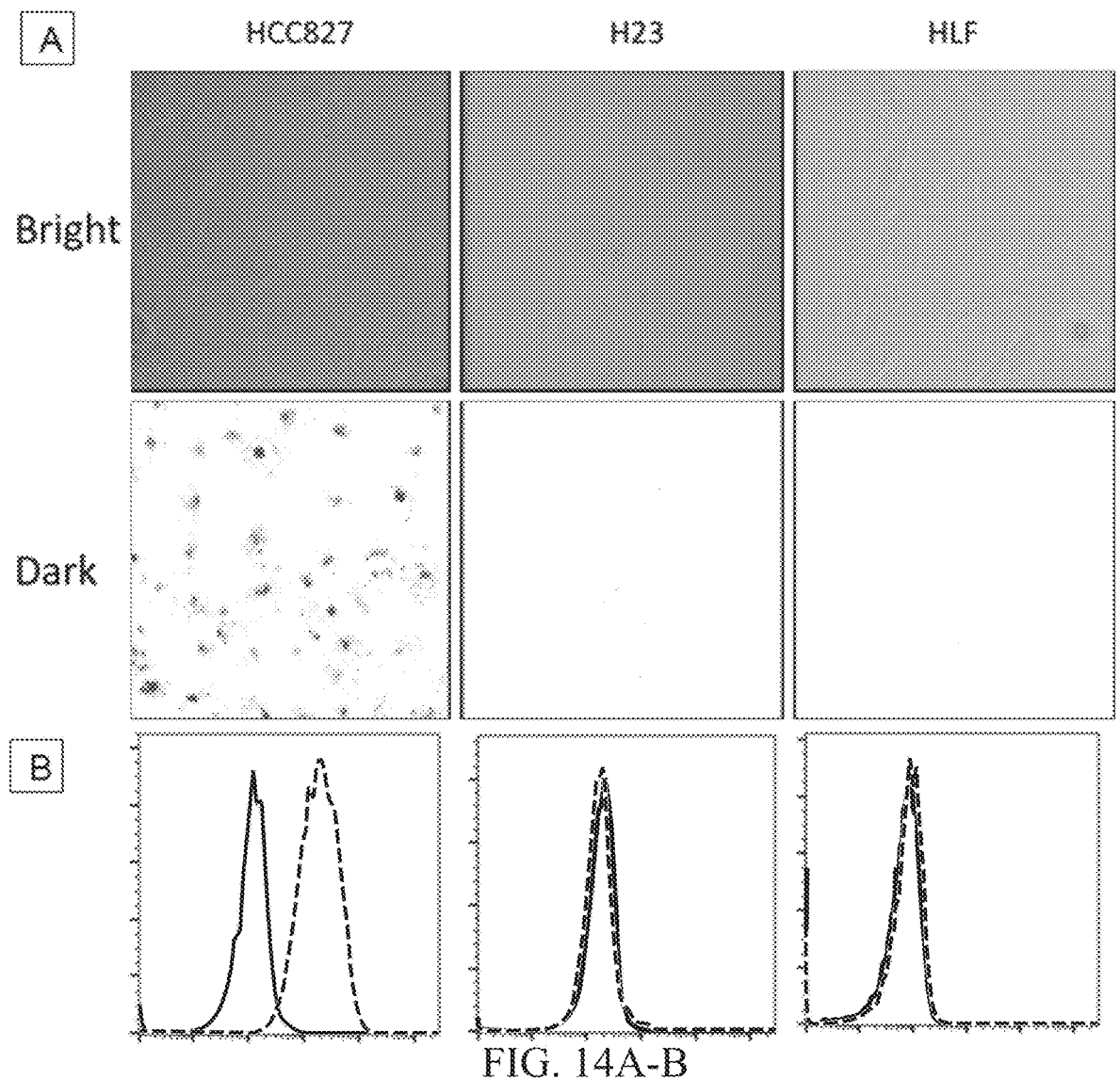
FIG. 14A-B

AIEGENS FOR CANCER CELL IMAGING

RELATED APPLICATIONS

This is a National Phase Application filed under 35 U.S.C. 371 as a national stage of PCT/CN2017/093831, filed Jul. 21, 2017, which claims priority to provisional U.S. Patent Application No. 62/493,902 filed Jul. 21, 2016, and provisional U.S. Patent Application No. 62/495,029 filed Aug. 31, 2016, which were filed by the inventors hereof and are incorporated by reference herein in their entirety.

TECHNICAL FIELD

The present subject matter relates to water-soluble aggregation induced emission (AIE) luminogens (AIEgens) for cancer cell imaging. In particular, the present subject matter relates to AIEgens for antibody labeling, a strategy for design of red emissive or near-infrared (NIR) emissive AIEgens, and application in targeted cancer cell imaging.

BACKGROUND

Organic dyes with red emission are favorable in many fields, such as the non-limiting examples of organic light-emitting diode (OLED), fluorescent imaging, and anti-counterfeit technologies, among others. For instance, fluorescent imaging as a biocompatible imaging technology can realize noninvasive, high resolution, and real time visualization as well as dynamic tracking of living organisms at a cellular level. As such, fluorescent imaging shows great potential in early detection and accurate diagnosis of various diseases. Compared to other imaging techniques, such as computed tomography (CT), magnetic resonance imaging (MRI), and positron emission tomography, fluorescent imaging has several advantages, such as low cost, high resolution, and real-time monitoring ability.

A large variety of fluorescent materials including natural polymers, organic small molecular dyes, inorganic quantum dots, and organic fluorescent nanoparticles have been investigated for fluorescence imaging and sensing. Among them, fluorescent nanoparticles based on organic dyes have been a research focus for their tunable size, low cytotoxicity, good photostability, and surface functionalization feasibility. Although organic emitters are rich in variety, the emissions of the traditional planar organic dyes are often weakened or even quenched in aggregates, which is known as aggregation-caused quenching (ACQ) and greatly restricts their application. This phenomenon is more serious for dyes with red or near-infrared red (NIR) emission, since the elongated π-conjugation or strong donor-acceptor (D-A) interaction favors strong π-π interaction to quench the emission. As such, there is a need for a red-emitting or NIR-emitting dye that withstands ACQ.

In addition, for cancer diagnosis and therapy, fluorescence molecular imaging is superior in sensitivity, resolution, low cost, and portability compared to other imaging modalities. Monoclonal antibodies are popular in preparing fluorescent molecular probes because monoclonal antibodies have high specificity to cancer cells and have acquired favorable clinical and pre-clinical results.

However, for a conventional "always-on" mAb-dye conjugate, the large amount of unbound probes will increase the background signal, thereby decreasing the target-to-background ratio (TBR), which results in poor image contrast. In contrast, if a "turn-on" mAb-dye conjugate is used, this trouble may be avoided, as "turn-on" mAb-dye conjugates emit considerable fluorescence inside cancer cells, thereby maximizing the signal from the target and minimizing the signal from the background, leading to high TBR and high image contrast.

There are several strategies of designing fluorescent "turn-on" antibody probes, such as fluorescence resonance energy transfer (FRET), H-dimer formation, and photo-induced electron transfer (PET). However, the development of antibody probes with FRET is complicated because it requires a well-matching and a precise distance between the donor and the acceptor. Moreover, it is also difficult to design and synthesize PET dyes that can conjugate with an antibody.

Further, the fluorescence of the probes may be activated by lysosomal conditions in specific cells including low pH, oxidation, unfolding, catabolism, or protein cleavage by lysosomal enzymes. However, there are problems with these conventional techniques, as not all of the fluorophores are able to form H-dimers and emissions of the fluorophores may not be fully extinguished upon conjugation with an antibody. As such, in order to attain the emission quenching, multiple fluorescent molecules are typically labeled in one antibody in conventional techniques. However, such a high labeling ratio is likely to interfere with the binding affinity. In addition, the nonspecific adsorbed dyes on the antibody and the dye molecules released after catabolism may return to the blood circulation, generating false-positive signals. Thus, a simple design of fluorescent molecules with improved properties remains highly desirable for developing fluorescent "turn-on" antibody probes.

SUMMARY

In an embodiment, the present subject matter is directed to a luminogen exhibiting aggregation induced emission, the luminogen comprising a structure of:

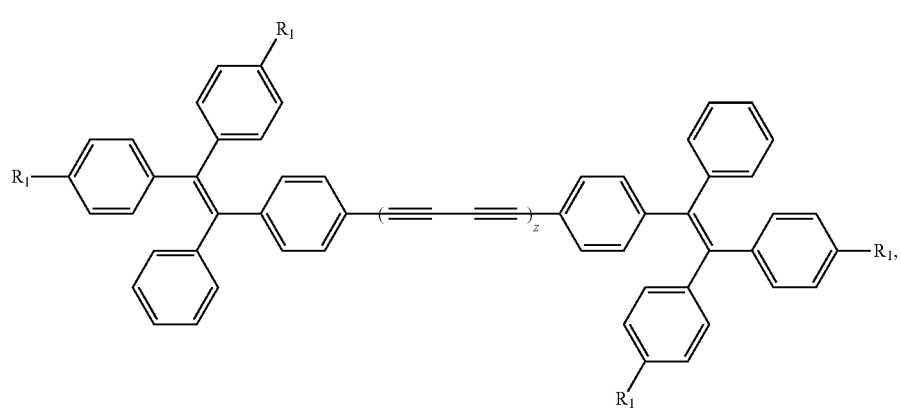

$T_1$

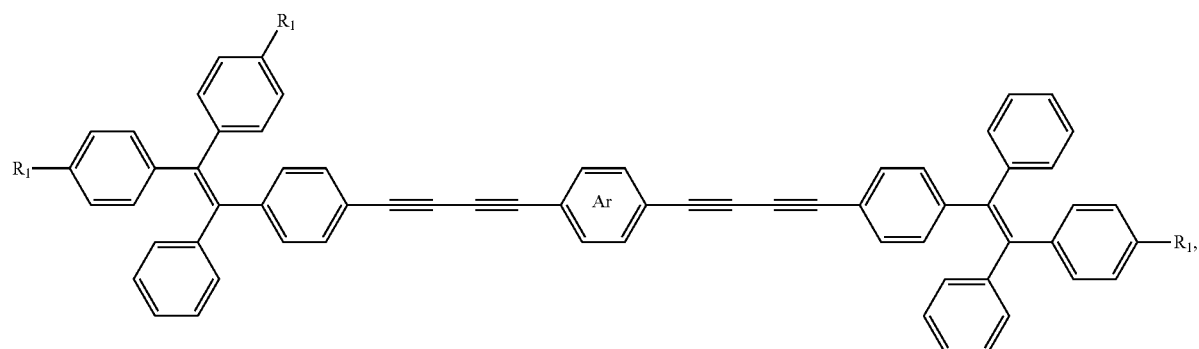
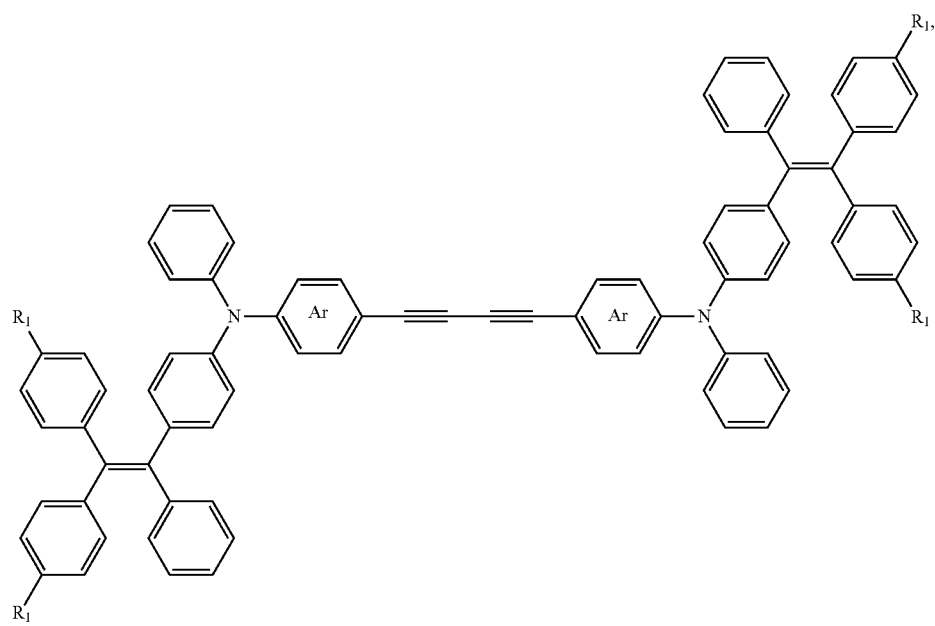
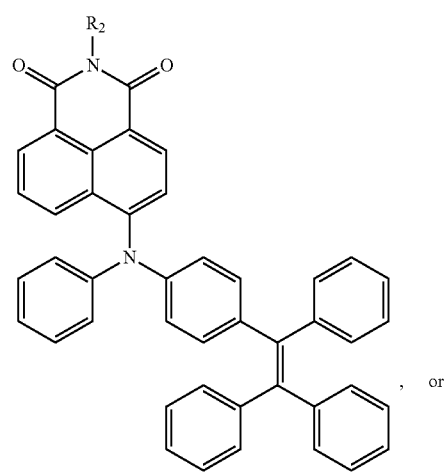
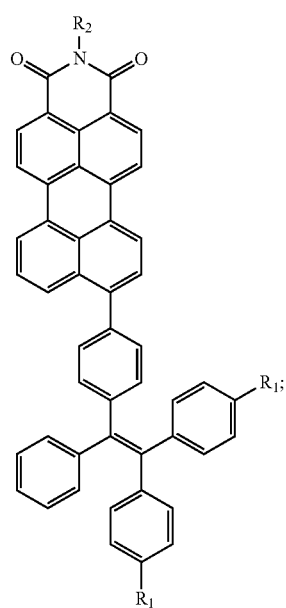

wherein

is selected from the group consisting of

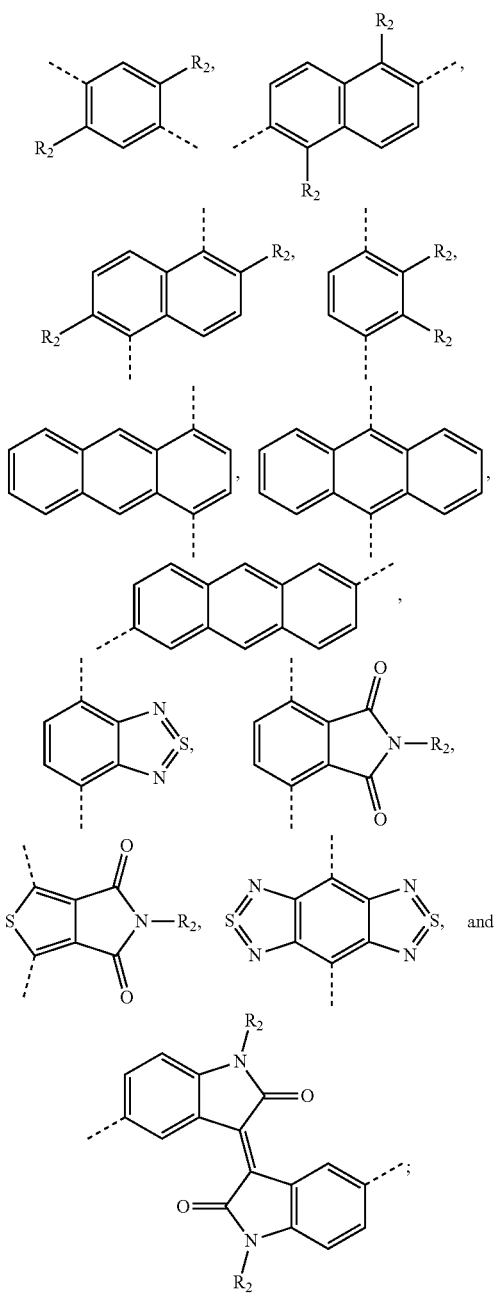

$R_1$ and $R_2$ are independently selected from the group consisting of —H, —OH, —SH, —$C_nH_{2n+1}$, —$OC_nO_mH_{2n+1}$, —$SC_nO_mH_{2n+1}$, —$NH_2$, and $N(C_nO_mH_{2n+1})_2$;

n is an integer from 1 to 24;
m is an integer from 0 to 10; and
z is 1 or 2; and wherein T1, T2, and T3 comprise one or more polyynes as a conjugated bridge.

In an embodiment, the present subject matter is directed to an AIEgen comprising: a hydrophilic pyridium group as a strong electron-withdrawing group; a piperazine group as an electron-donating group; and a α-Cyanostilbene; wherein the AIEgen exhibits aggregation induced emission.

In an embodiment, the present subject matter is directed to a method of synthesizing an AIEgen, comprising:

reacting

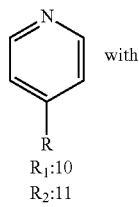

$R_1$:10
$R_2$:11 with

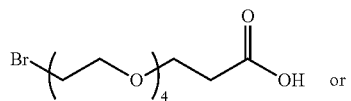

or

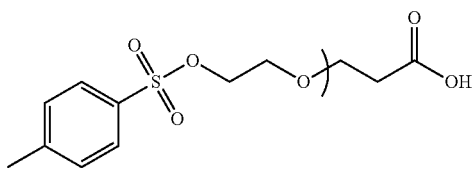

and toluene to obtain an intermediate; and reacting the intermediate with DCC, NHS, and DMF to obtain the AIEgen; wherein the intermediate is

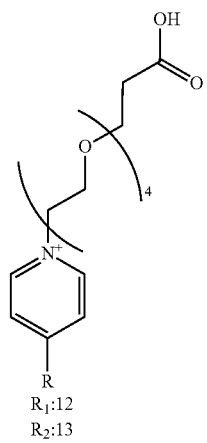

$R_1$:12
$R_2$:13 and the AIEgen is

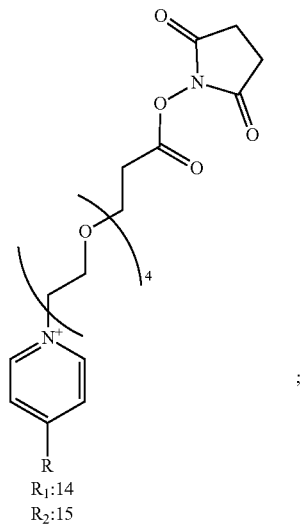

R₁:14
R₂:15 wherein R₁ comprises

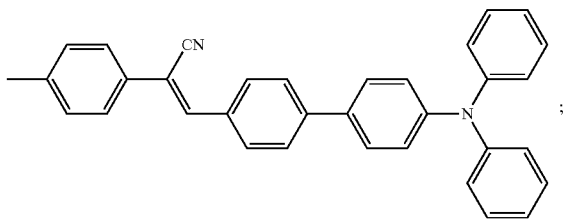 [SMILES: Cc1ccc(/C(C#N)=C/c2ccc(-c3ccc(N(c4ccccc4)c4ccccc4)cc3)cc2)cc1]

and
wherein R₂ comprises

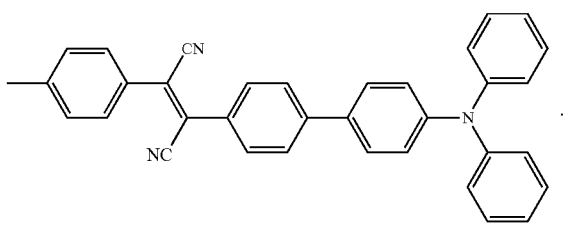 [SMILES: Cc1ccc(/C(C#N)=C(\C#N)c2ccc(-c3ccc(N(c4ccccc4)c4ccccc4)cc3)cc2)cc1]

In an embodiment, the present subject matter is directed to a method of labeling comprising incubating a subject having cells with a conjugate formed by conjugating an AIEgen with an antibody; and selectively labeling desired cells by turn-on imaging, wherein labeling occurs when the desired cells are selectively stained by fluorescent emission of the AIEgen upon degradation of the antibody after cellular internalization of the conjugate through endocytosis.

BRIEF DESCRIPTION OF DRAWINGS

FIG. 2 shows a high resolution mass spectrum (MALDI-TOF) of TPE-2E.

FIG. 3A-B shows (A) $^1$H NMR and (B) $^{13}$C NMR spectra of 2TPE-4E.

FIG. 8A-J shows A) the fabrication of mAb-AIE dots; and B-J) confocal images of HCC 827 cells after incubation with mAb-AIE dots (2.5 μg mL$^{-1}$ of 2TPE-4E), AIE dots (2.5 μg mL$^{-1}$ of 2TPE-4E), and firstly antibody, then mAb-AIE dots for 6 hours. Scale bar=20 μm.

FIG. 9A-I shows confocal images of HCC 827 (A, E), NCI-H 23 (B, F), NIH 3T3 (C, G), and MDCK 2 (D, H) cells after incubation with AC-AIE dots for 8 hours; and I) flow cytometry histograms of HCC 827, NCI-H 23, NIH 3T3, MDCK 2 cells after incubation with mAb-AIE dots (2.5 μg mL$^{-1}$ of 2TPE-4E) at 37° C. for 8 hours.

FIG. 10A-G shows images of HCC 827 cells cultured by AC-AIE dots (A-C), and LysoTracker-Red (D-F) upon laser scanning with different scanning time. G) Fluorescence signal attenuation after continuous exposure for designated time intervals.

FIG. 14A-B shows confocal images of A) HCC 827, NCI-H 23, and HLF cells after incubation with org-5-mAb-AIE dots for 8 hours. B) Flow cytometry histograms of HCC 827, NCI-H 23, HLF cells after incubation with org-5-mAb-AIE dots (2.5 μg mL$^{-1}$ of 2TPE-4E) at 37° C. for 8 hours.

DETAILED DESCRIPTION

Definitions

Figure 1A:
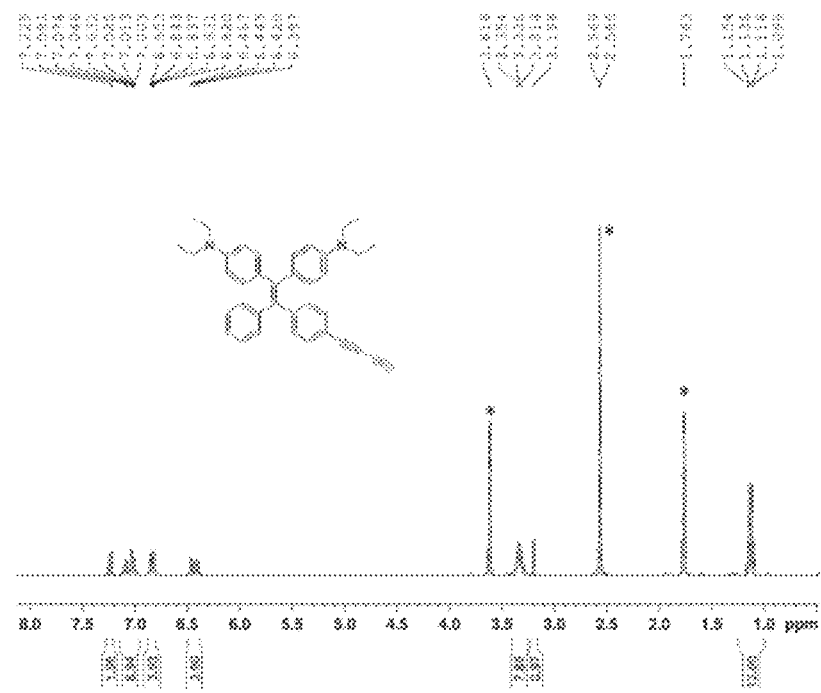
FIG. 1A-B shows (A) $^1$H NMR and (B) $^{13}$C NMR spectra of TPE-2E.

The following definitions are provided for the purpose of understanding the present subject matter and for constructing the appended patent claims.

It is noted that, as used in this specification and the appended claims, the singular forms "a", "an", and "the" include plural references unless the context clearly dictates otherwise.

"Aggregation-induced emission", or AIE, means the fluorescence/phosphorescence is turned on upon aggregation formation or in the solid state. When molecularly dissolved, the material is non-emissive, but emission is turned on when intramolecular rotation is restricted.

"Emission intensity" refers to the magnitude of fluorescence/phosphorescence normally obtained from a fluorescence spectrometer or fluorescence microscopy measurement; "fluorophore" or "fluorogen" refers to a molecule which exhibits fluorescence; "luminogen" refers to a molecule which exhibits luminescence; and "AIEgen" refers to a molecule exhibiting AIE characteristics.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Luminogens and Luminogens with Polyynes as a Conjugated Bridge

Molecular rotors with aggregation-induced emission (AIE) characteristics generally show non-emission or weak emission in dilute solution, but show enhanced fluorescence in aggregates through restriction of intramolecular motion (RIM). The unique emission property of AIE luminogens (AIEgens) has paved the way for preparation of highly emissive organic fluorescence nanoparticles.

Due to lower cellular or tissue auto-fluorescence interference and anti-photo bleaching ability, long wavelength red emissive organic dyes are more favorable compared to other traditional visible-light emissive dyes in bio-application. Until now, the design and synthesis of the red and NIR emissive AIEgens has been challenging. For example, most of the AIEgens have highly twisted structures. As such, effectively red-shifting the emission by merely expanding the electron delocalization of a π-system has been very difficult due to the poor π-conjugation of the involved molecular backbone. Additionally, the occurrence of too large π-conjugation through fused rings or double bonds likely leads to poor solubility and/or increases the instability of the AIEgens, and may even lead to ACQ problems.

Constructing D-A structures is a very efficient strategy for affording red emitters. However, the twisted structures make the emission of D-A type AIEgens suffer the influence of twisted intramolecular charge transfer (TICT), which has been proposed as one of the major non-radiative decay pathways for D-A type fluorophores. Additionally, expanding the π-conjugation of D-A structures probably also results in ACQ problems due to the strong intermolecular π-π interaction. As a sp-hybridized carbon allotrope, polyynes represent a special class of conjugated bridges that endow organic π-functional materials with big π-conjugation and unique electronic, optical and physical properties.

However, using polyynes to construct red emissive AIEgens has not been investigated until now. In the present subject matter, the polyyne moieties work as a bridge to expand the π-conjugation and also act as an electron acceptor to promote the ICT and to achieve red emission.

In an embodiment of the present subject matter, a strategy was proposed for red AIEgen design by employing polyynes as a conjugated bridge. The polyynes-based AIEgens consist of three parts, namely TPE, silole, or cyano-stilbene derivatives as rotators; polyynes as a conjugated bridge; and electron-deficient moieties as acceptors. These AIEgens show red or NIR emission, which present non-emission or weak emissions in a solution state, but present enhanced emission in an aggregation state.

In an embodiment, the present subject matter is directed to a luminogen exhibiting aggregation induced emission, the luminogen comprising a structure of:

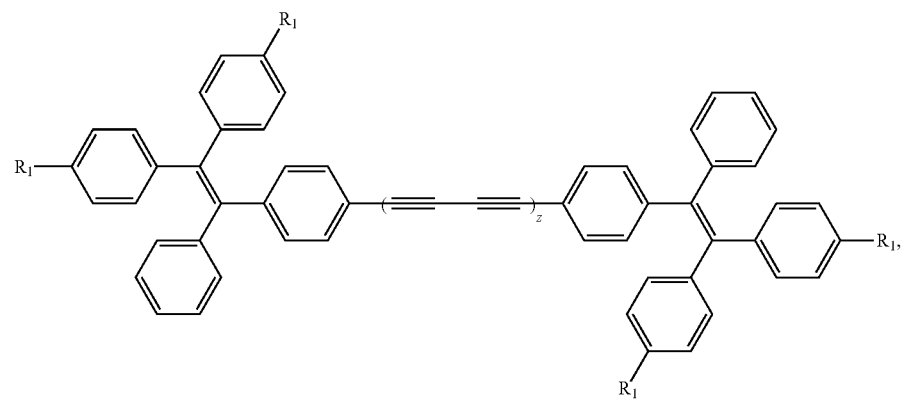
T₁
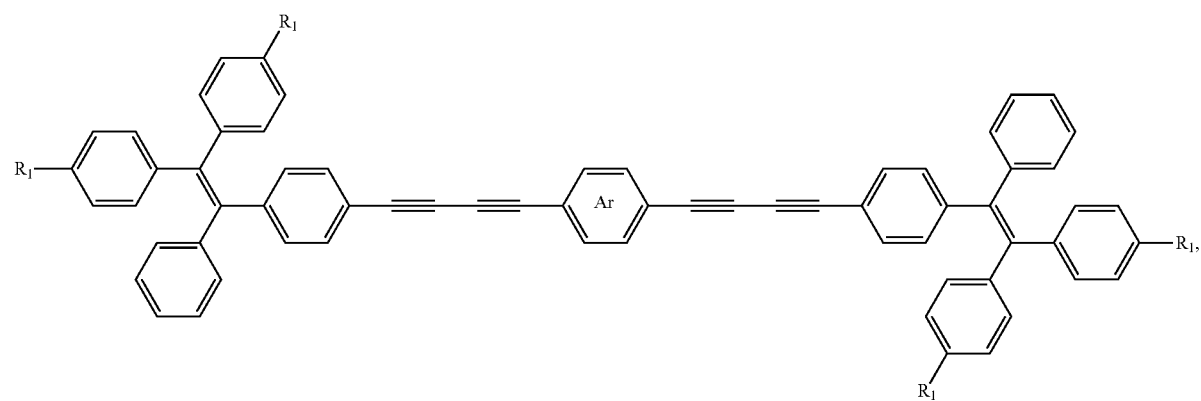
T₂
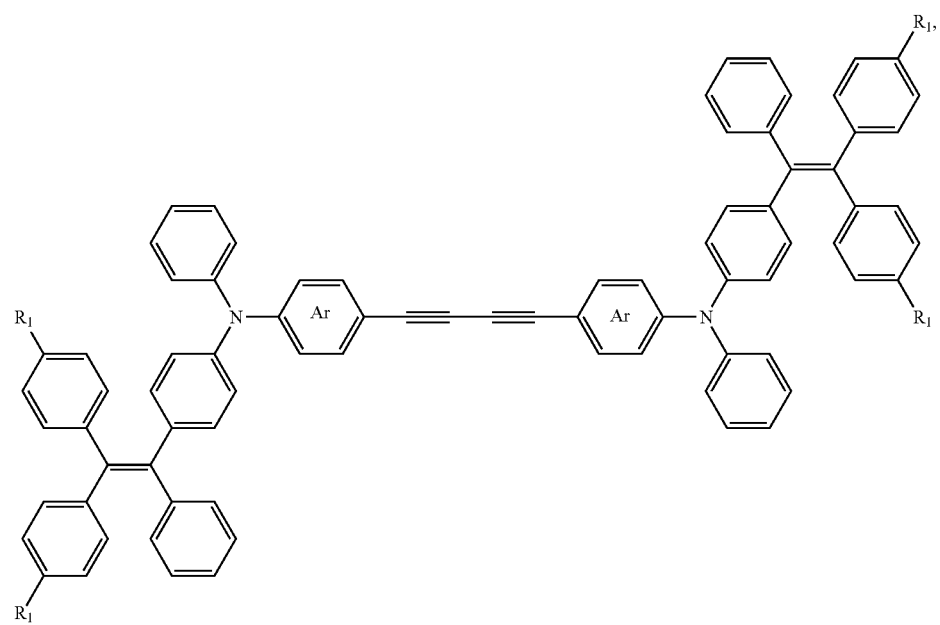
T₃

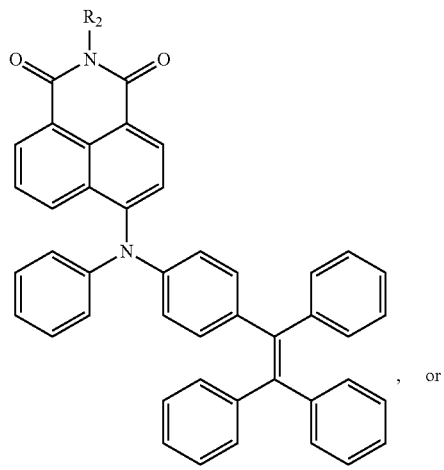, or 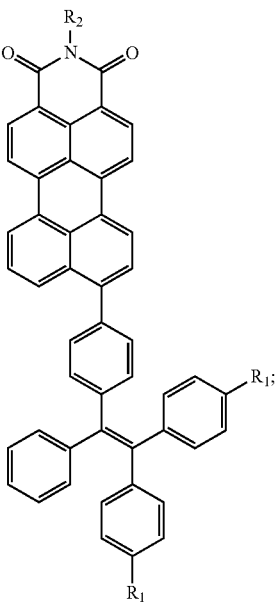;

wherein

is selected from the group consisting of

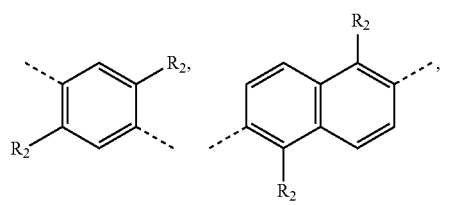

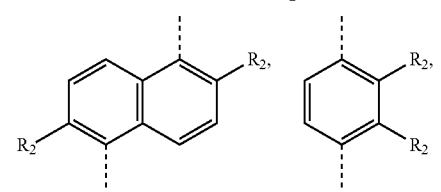

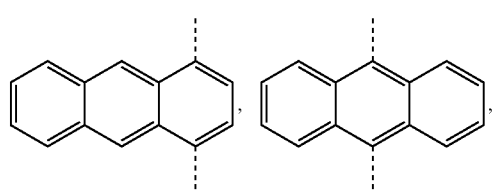

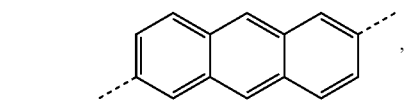

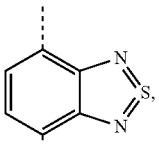 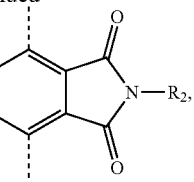

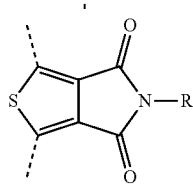 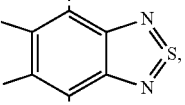, and

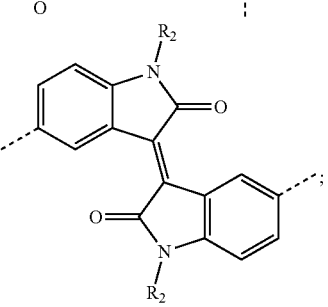;

$R_1$ and $R_2$ are independently selected from the group consisting of —H, —OH, —SH, —CnH2n+1, —OC$_n$O$_m$H$_{2n+1}$, —SC$_n$O$_m$H$_{2n+1}$, —NH$_2$, and N(C$_n$O$_m$H$_{2n+1}$)$_2$;

n is an integer from 1 to 24;

m is an integer from 0 to 10; and z is 1 or 2; and wherein T1, T2, and T3 comprise one or more polyynes as a conjugated bridge.

For example, a non-limiting embodiment of the present subject matter is directed to synthetic routes shown below for 2TPE-4E and other derivatives, such as T2, TPETA-BT2E, org-5, and T6.

Scheme 1
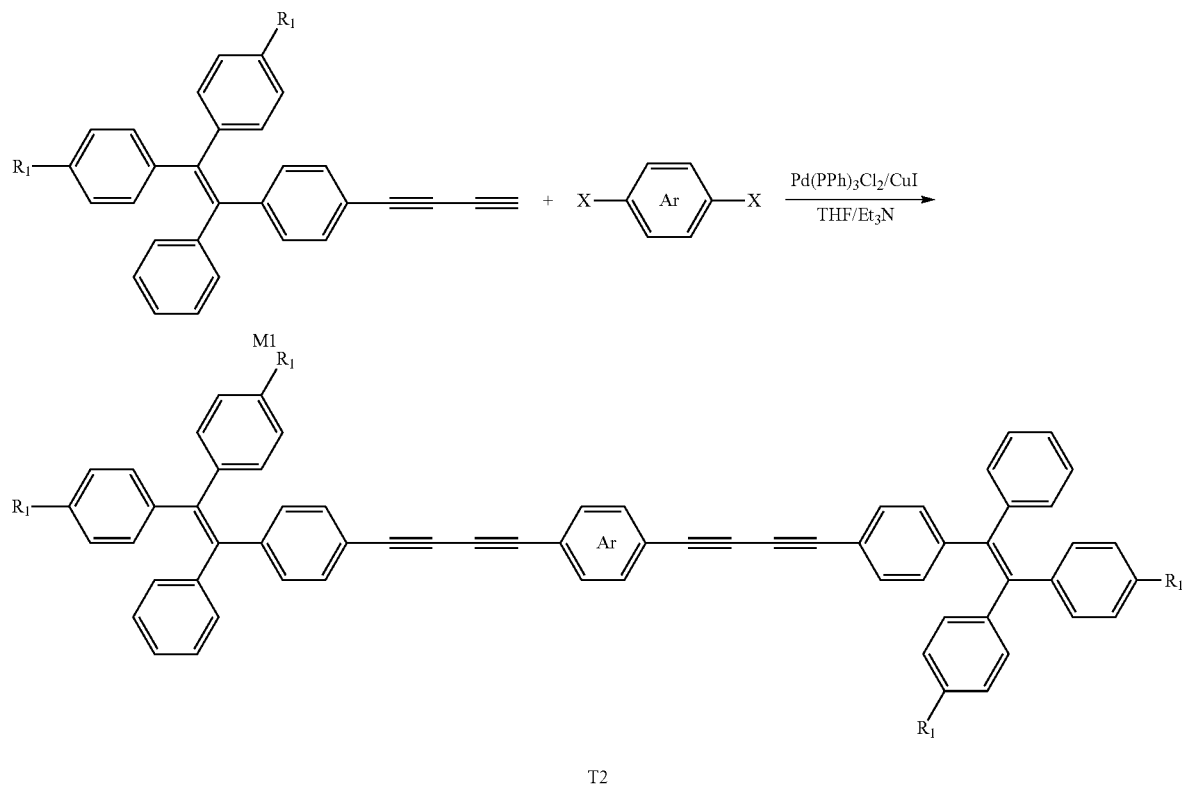
T2
Scheme 2
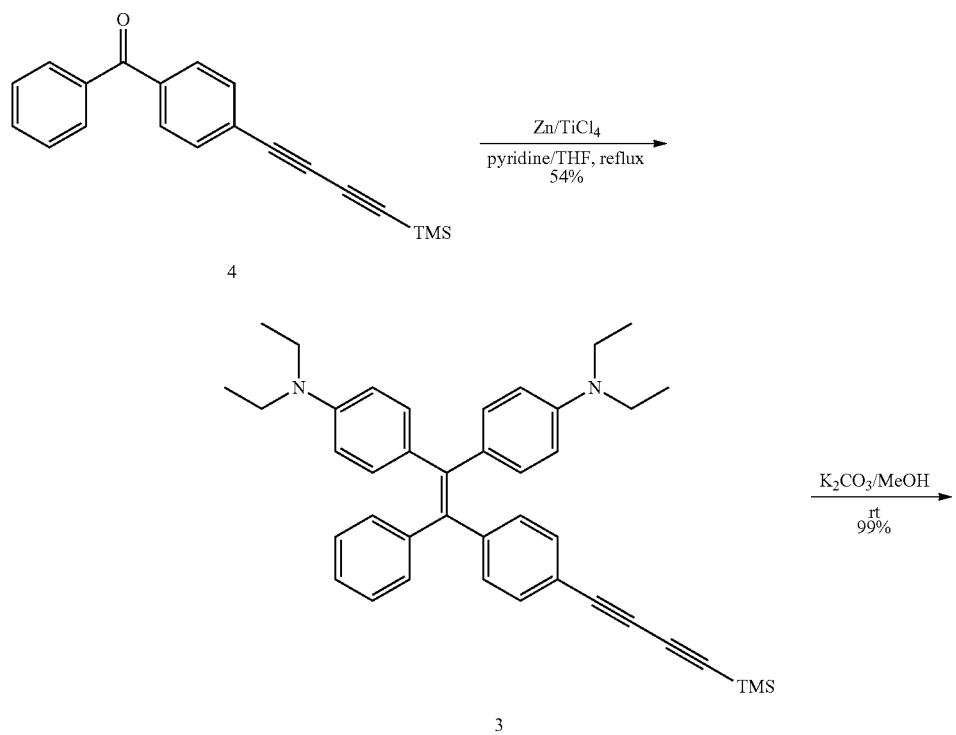

-continued
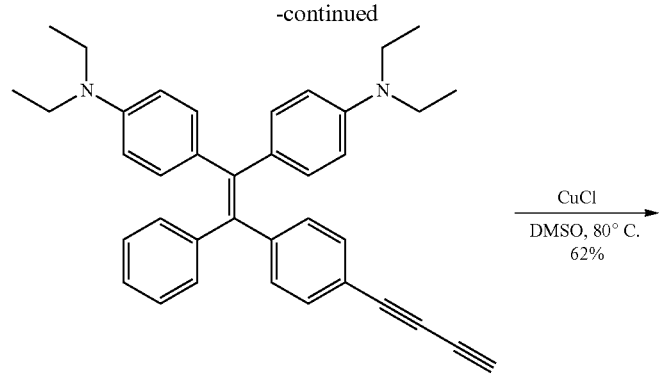
2
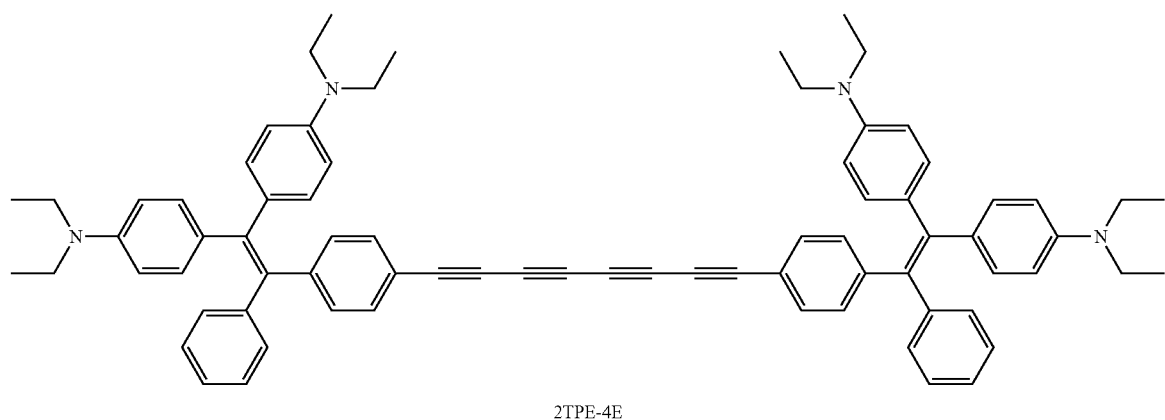
2TPE-4E
Scheme 3
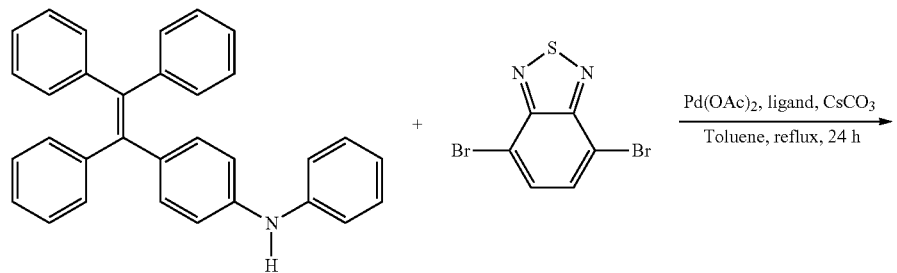

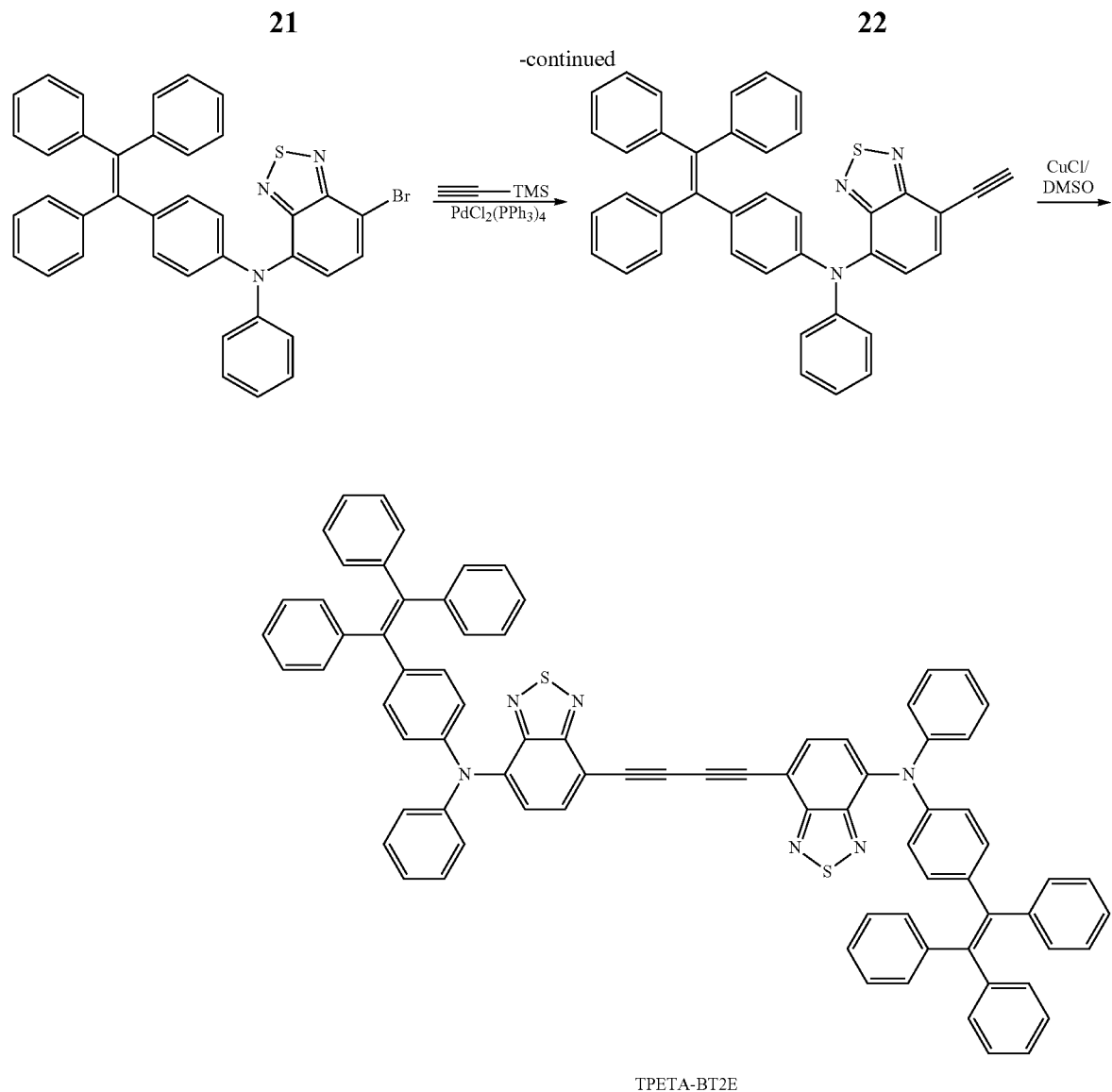
TPETA-BT2E
Scheme 4
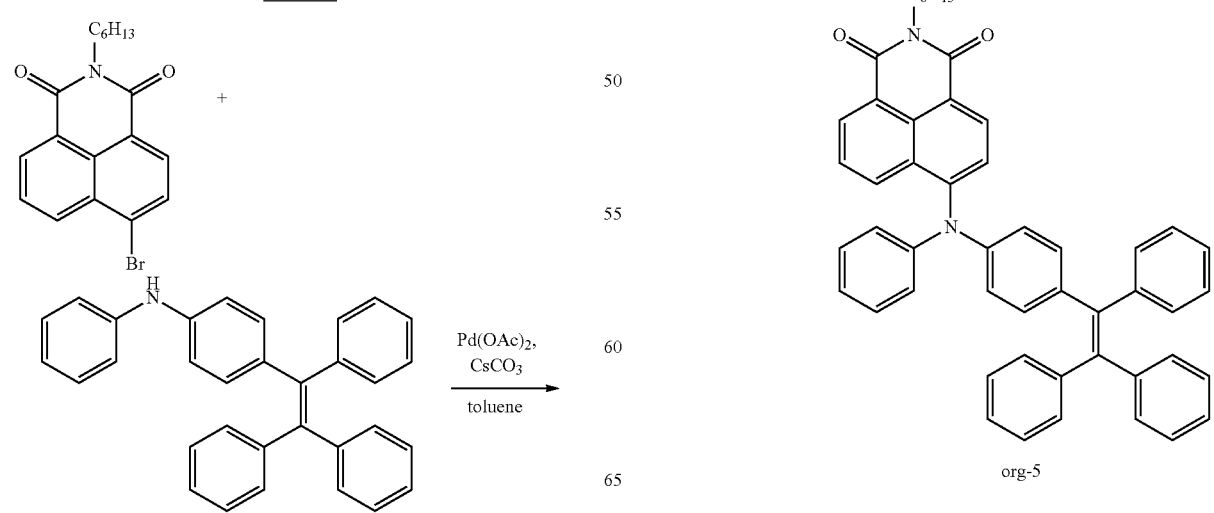
org-5

Scheme 5

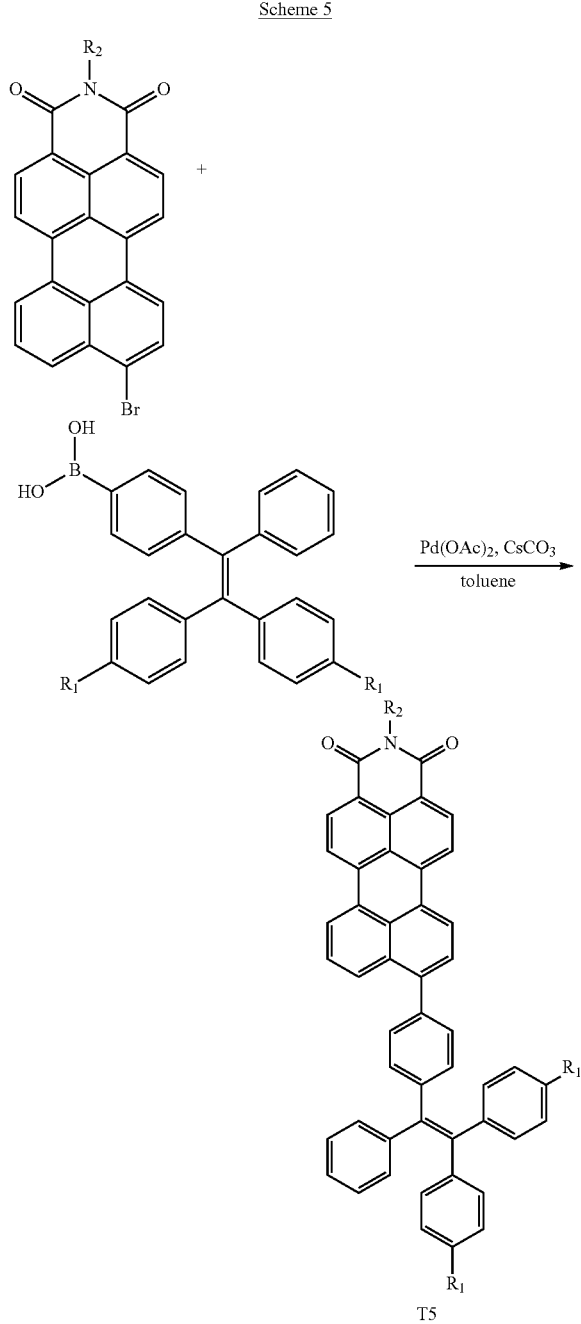

T5

In an embodiment of the present subject matter, the fluorescent nanoparticles were fabricated and successfully conjugated with aptamer and antibody, resulting in the targeted AIE dots. The aptamer and antibody anchored nanoparticle encapsulation strategy may also be applied for other AIEgens.

These kinds of targeted AIE dots have many applications, such as the non-limiting examples of cancer cell targeted imaging, accurate diagnosis of disease, and imaging guided drug delivery. For example, by encapsulating a chemotherapeutic drug (Paclitaxel, PTX) simultaneously into the AIE dots, the targeted AIE dots showed better therapeutic effects relative to the un-targeted one.

Figure 1B:
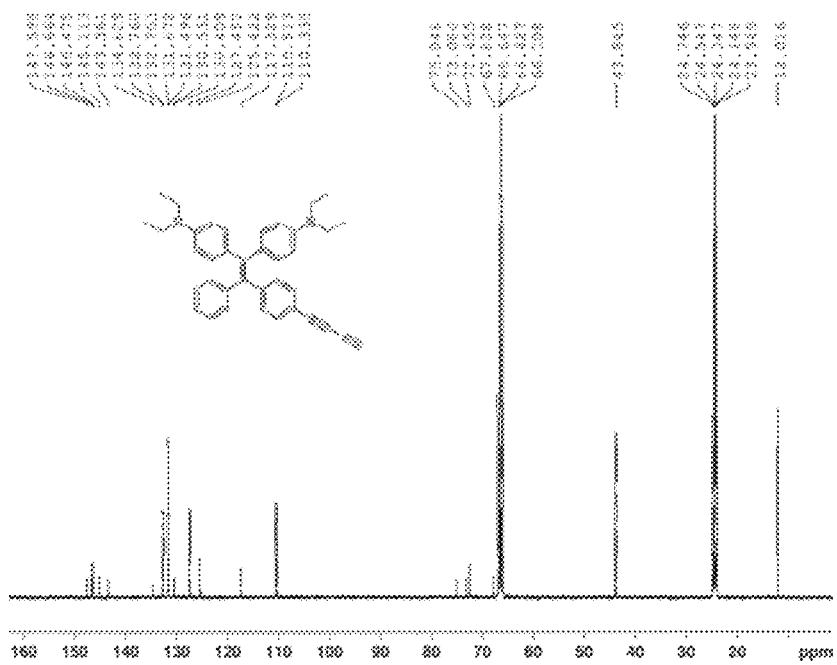
Figure 3B:
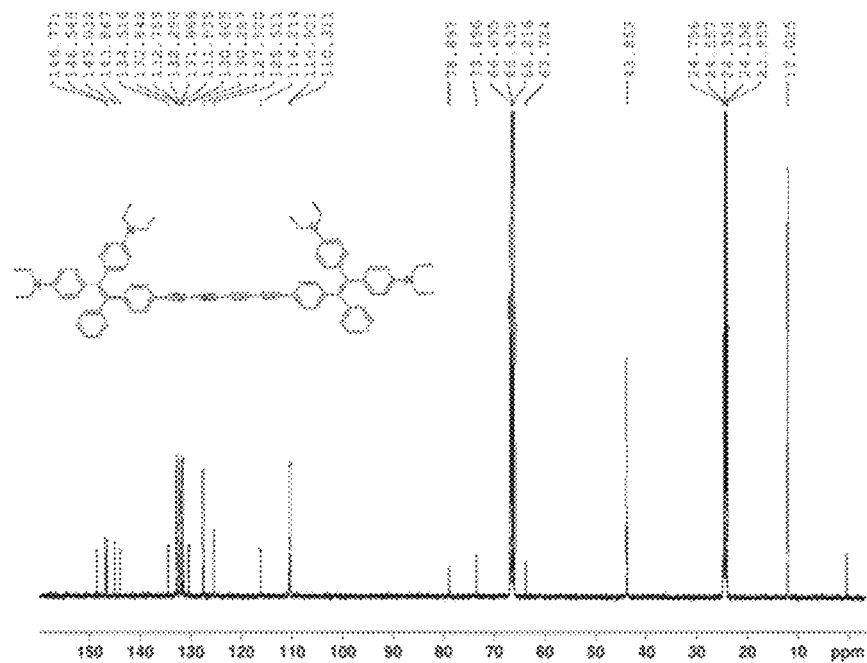
Figure 4:
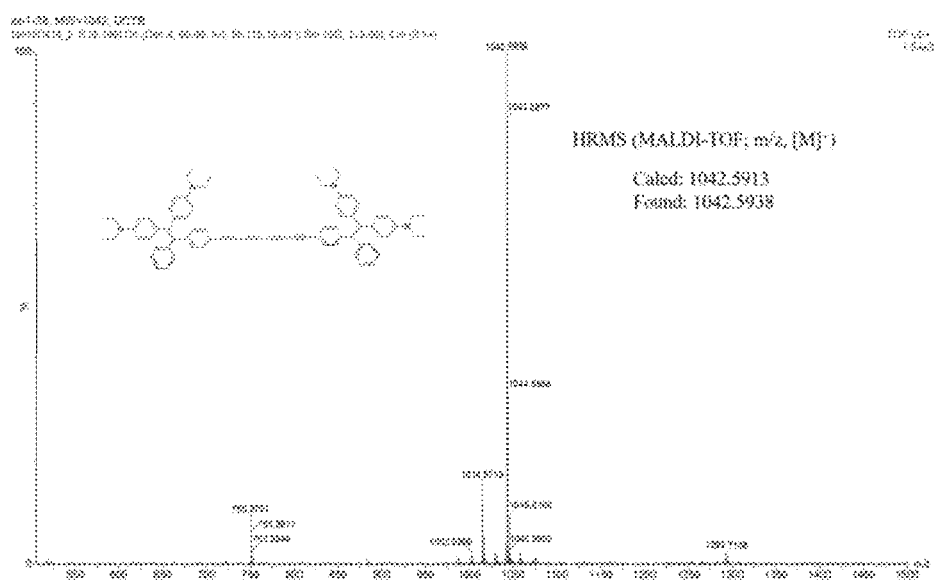
FIG. 4 shows a high resolution mass spectrum (MALDI-TOF) of 2TPE-4E.
Figure 5A:
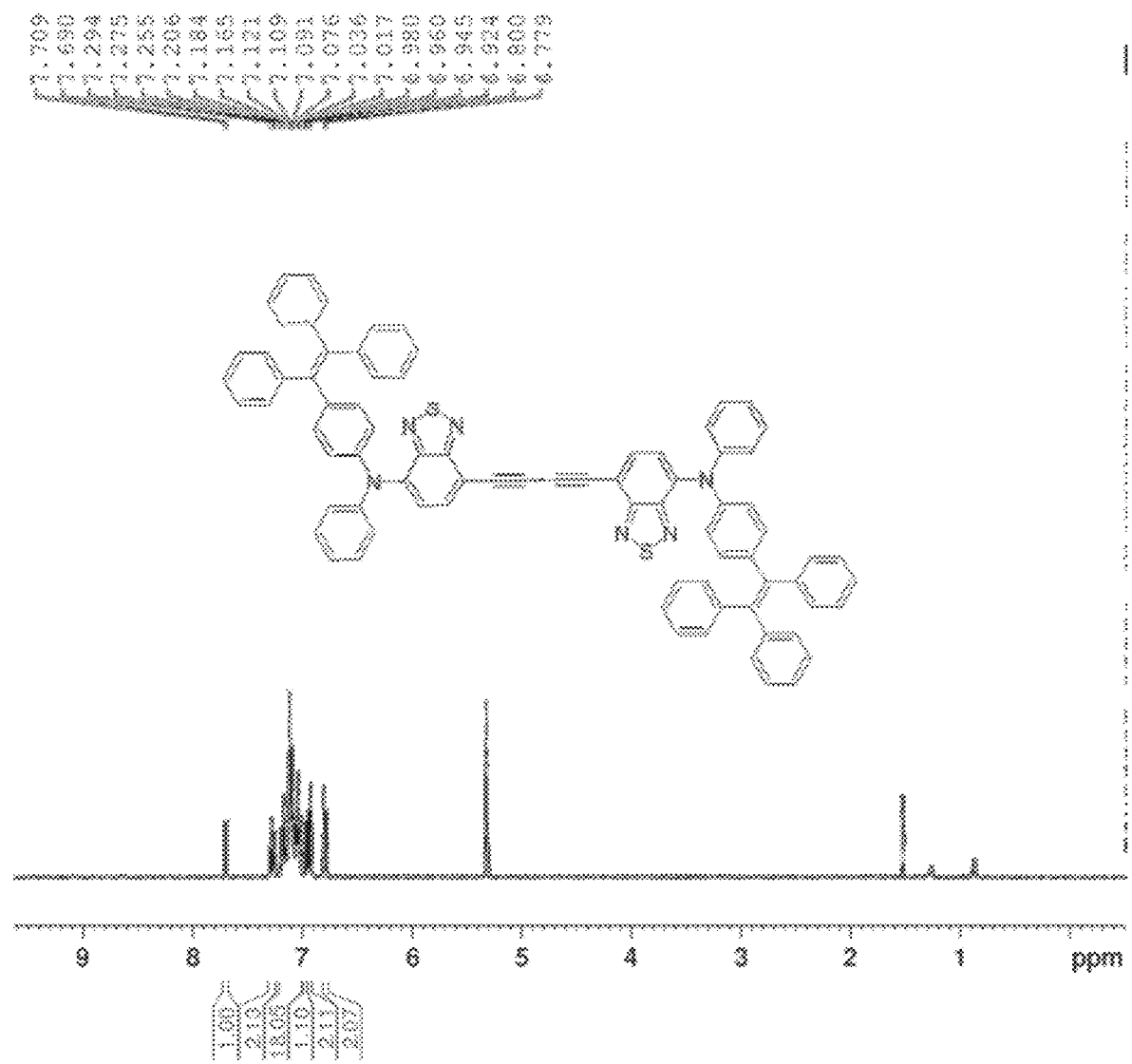
FIG. 5A-B shows (A) $^1$H NMR and (B) $^{13}$C NMR spectra of TPETA-BT2E.
Figure 5B:
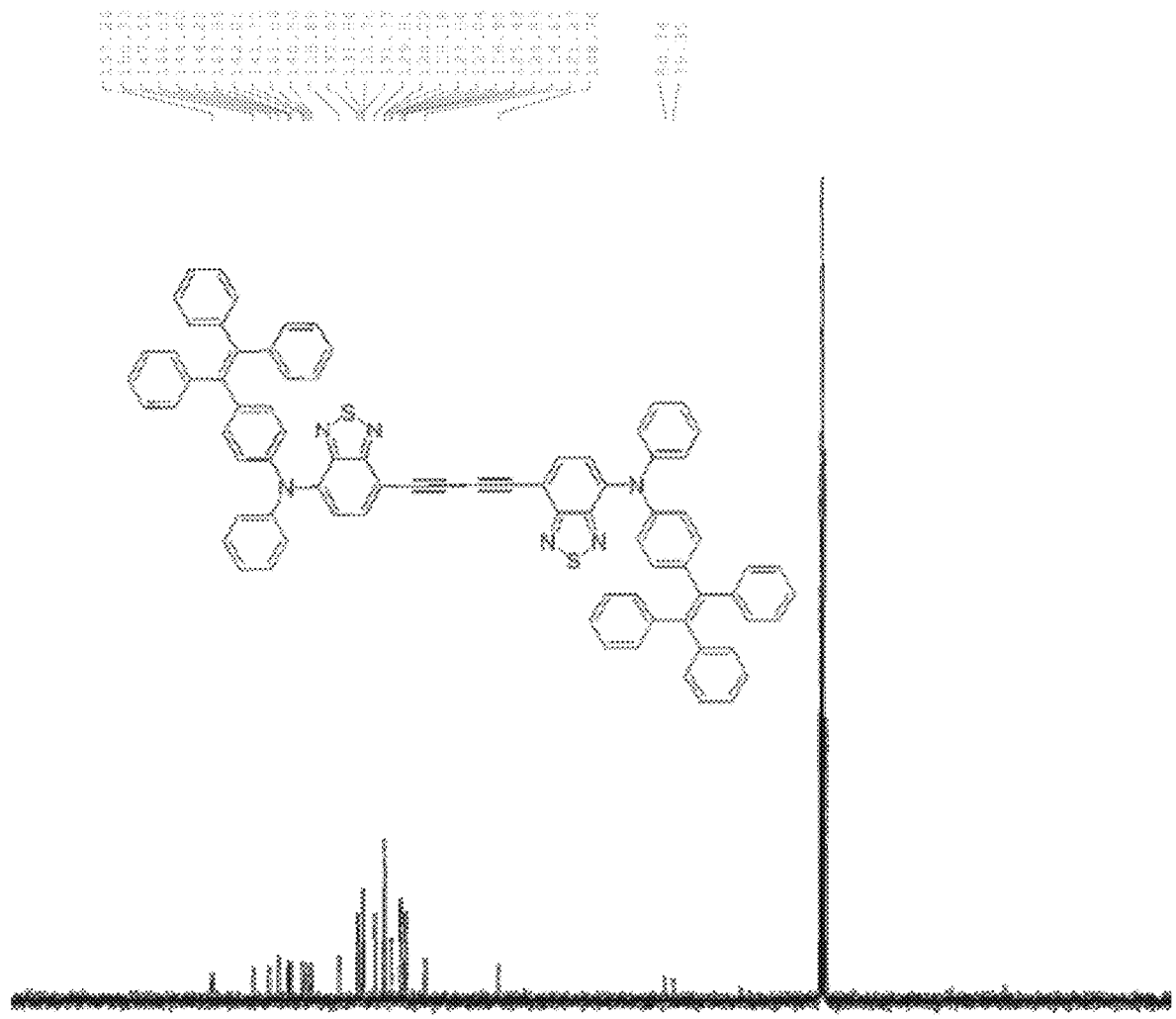
Figure 6A:
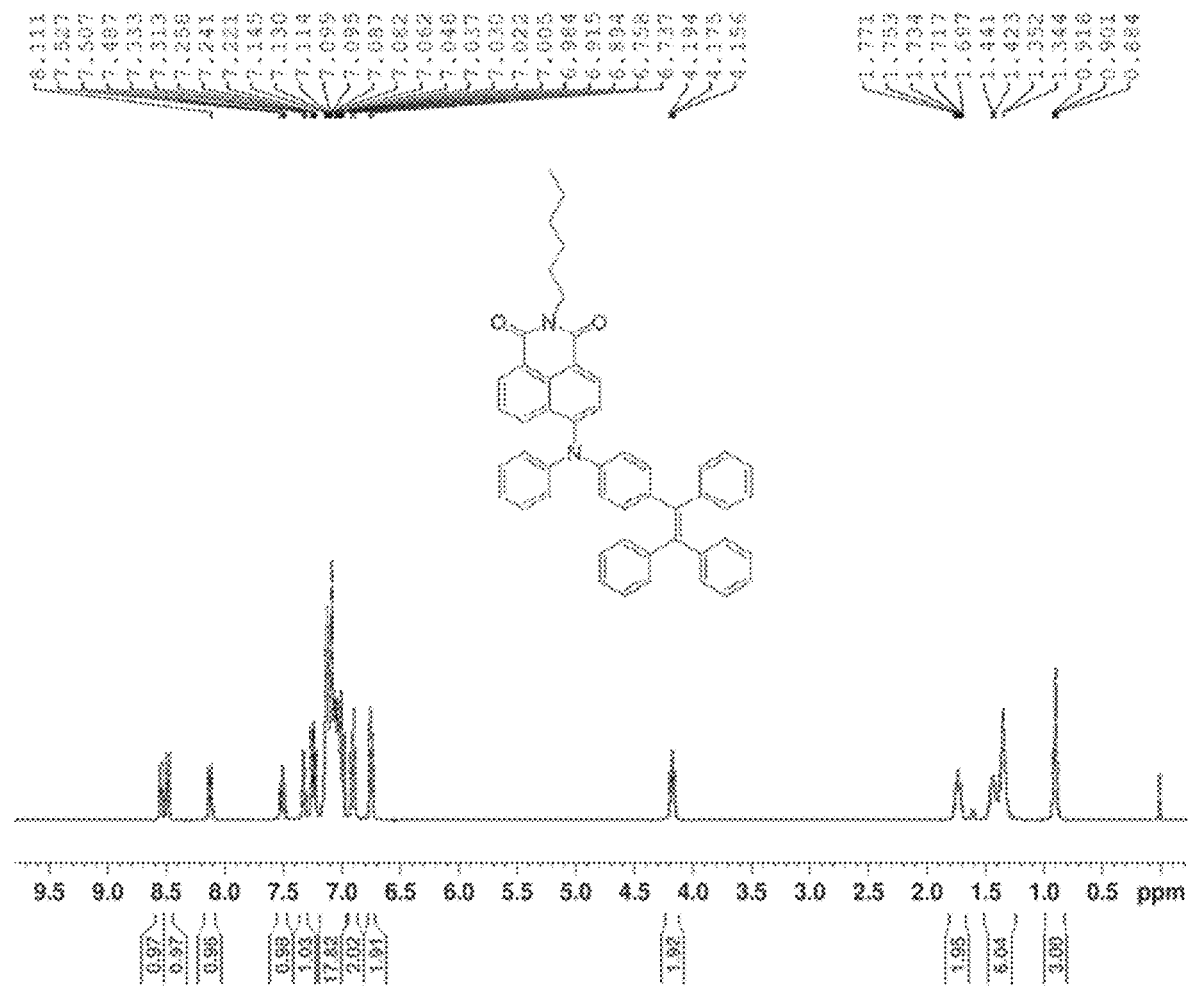
FIG. 6A-B shows (A) $^1$H NMR and (B) $^{13}$C NMR spectra of org-5.
Figure 6B:
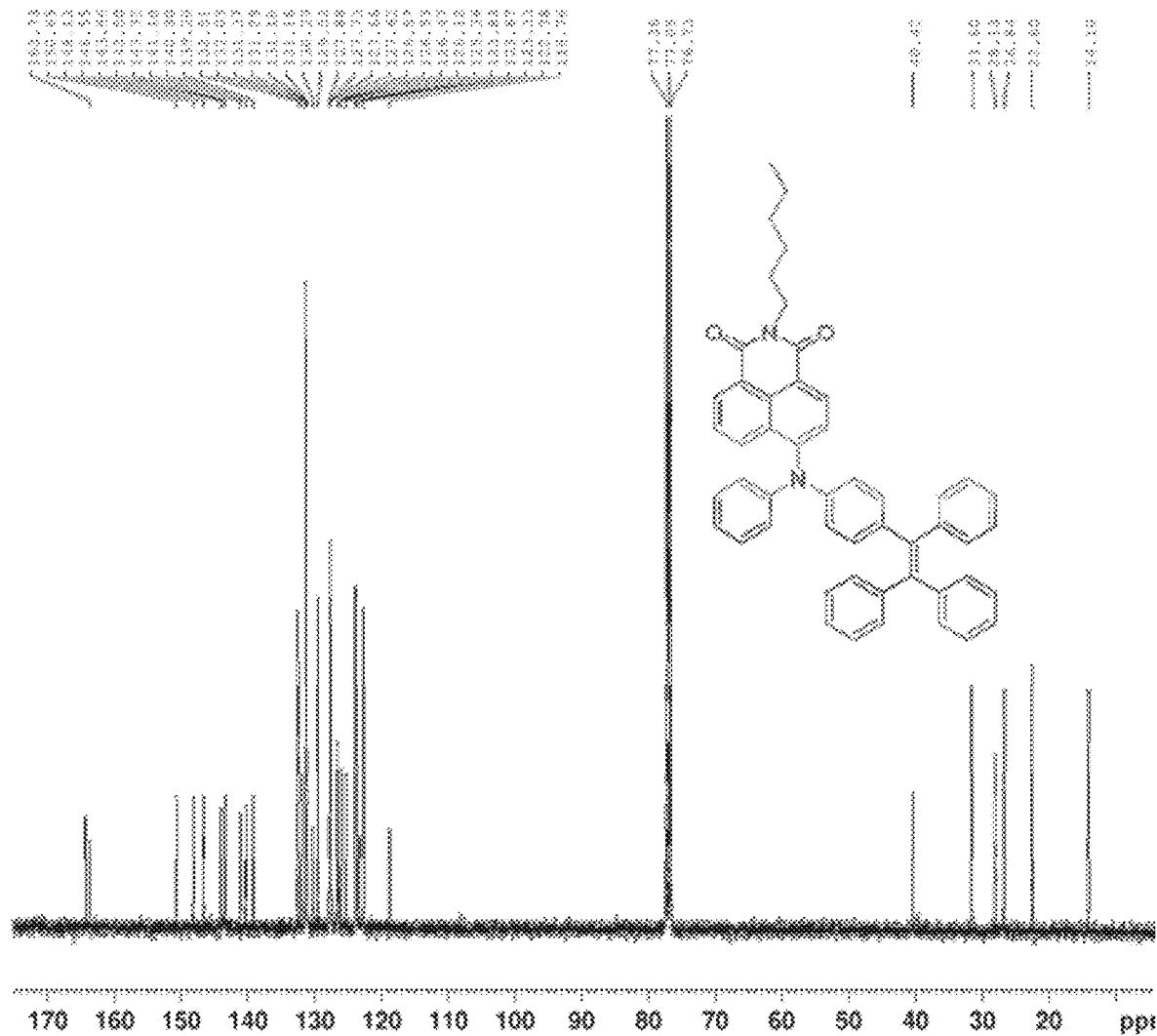

In addition, the $^1$H NMR, $^{13}$C NMR, and MALDI-TOF spectra were taken for TPE-2E (FIG. 1A-B and FIG. 2) and 2TPE-4E (FIG. 3A-B and FIG. 4), and the $^1$H NMR and $^{13}$C NMR spectra were taken for TPETA-BT2E (FIG. 5A-B) and org-5 (FIG. 6A-B). For FIG. 1, the shift A model compound according to the present subject matter is 2TPE-4E, which is distinguished by a big π-system using an octatetrayne (C≡C—C≡C—C≡C—C≡C) as a conjugate bridge and acceptor. In application, AIE dots based on 2TPE-4E were fabricated and successfully conjugated with C225 and aptamer, affording the antibody or aptamer targeted AIE dots for cancer cell imaging. The resulted mAb-AIE dots show excellent specificity to HCC-827 lung cancer cells with high EGFR expression level. The aptamer anchored AIE dots can target several cancer cells. These targeting groups conjugated AIE dots can also be applied to other AIEgens, indicating their practicability. Thanks to the high photostability of mAb-AIE dots, the targeting process of the mAb-AIE dots could be investigated.

Imaging guided therapy was explored by encapsulating the AIEgens and chemotherapeutic drug (Paclitaxel, PTX) simultaneously into the AIE dots. This not only demonstrated an effective strategy for affording red emissive AIEgen, but also indicated the targeted-AIE dots are excellent fluorescent imaging agents for targeted imaging of cancer cells. As another non-limiting application, AIE dots based on 2TPE-4E were fabricated and successfully conjugated with AS1411 aptamer, affording the aptamer-targeted AIE dots (aptamer-AIE dots) for specific breast cancer cell and lung cancer cell imaging. The aptamer-AIE dots show excellent specificity to MCF-7 breast cancer cells and lung cancer cells with high nucleolin expression levels. Aptamer-AIE dot nanoprobes are suitable for longtime, real-time, and dynamic sensing, tracking, and imaging, making them extremely promising for use in vivo study and disease diagnosis.

In an embodiment, the luminogen of the present subject matter exhibits red emission or near infrared emission. In an embodiment, the luminogen of the present subject matter is a nanoparticle fabricated in a polyethylene glycol (PEG) matrix. In an embodiment, the nanoparticle is conjugated with an antibody, aptamer, folic acid, or peptide to form an AIE dot. In an embodiment, the luminogen of the present subject matter is used for targeted imaging of cancer cells.

In an embodiment, the luminogen of the present subject matter is 2TPE-4E having a structure of:

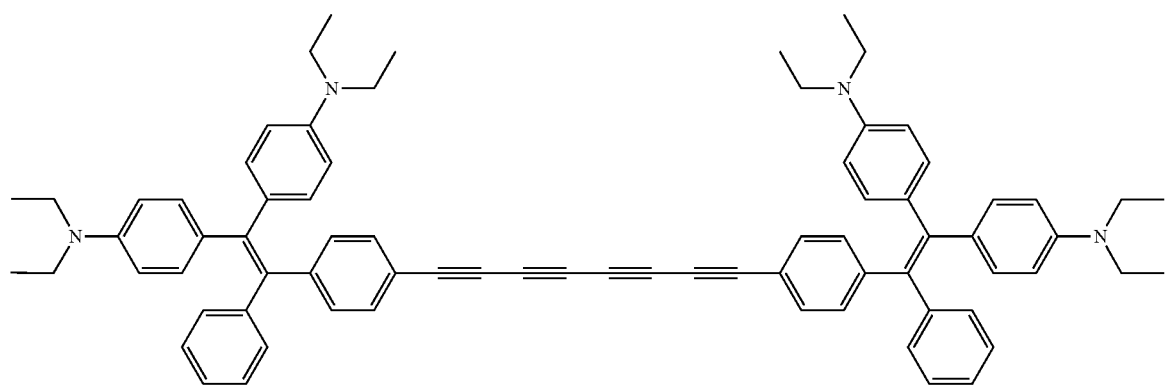
2TPE-E4
In an embodiment, the luminogen of the present subject matter is TPETA-BT2E having a structure of:
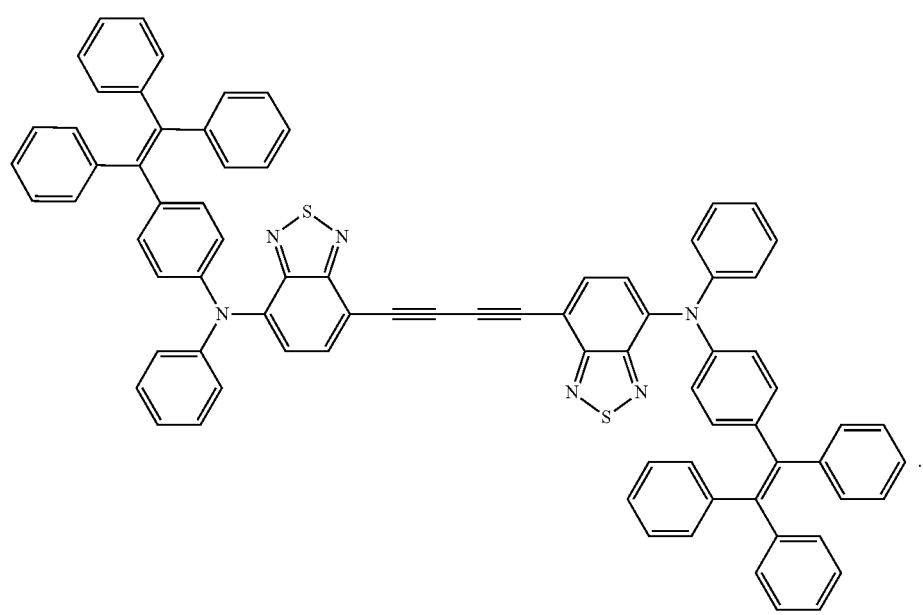
TPETA-BT2E In an embodiment, the luminogen of the present subject matter is org-5 having a structure of:

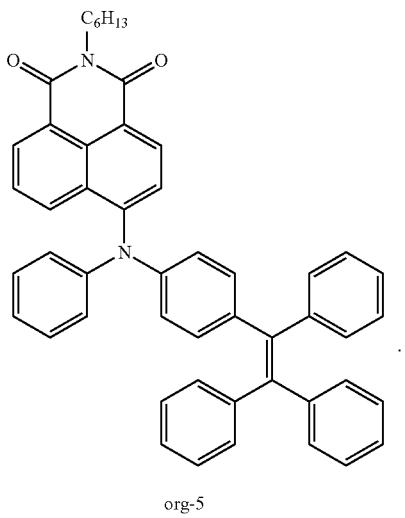

org-5

In an embodiment of the present subject matter, a key intermediate in the polyynes-based AIEgen is $M_1$:

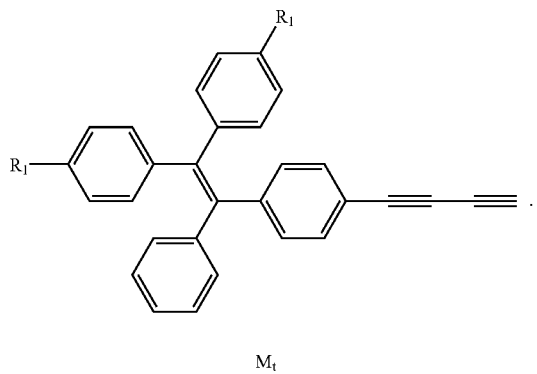

$M_t$

Synthesis, Characterization, and Design Principle of 2TPE-4E

The synthetic route for 2TPE-4E was shown in Scheme 2. Compound 4 was synthesized according to the literature method where 4-bromobenzophenon undergoes Sonogashira coupling twice to obtain the diyyne substituted benzophenone. Asymmetric McMurry coupling between compound 4 and 4,4'-bis(diethylamino)benzophenone affords compound 3 in moderate yield. The TMS-alkyne deprotection of compound 3 is highly efficient, giving compound 2 in almost quantitative yield. Finally, the target compound 2TPE-4E could be facilely prepared by self-coupling of compound 2 using the low-cost CuCl as catalyst in a yield of 62%. The synthetic details are presented as follows:

Synthesis of compound 4. Compound 4 was synthesized according to the literature method. In general, 4-bromobenzophenon undergoes Sonogashira coupling twice to obtain the diyyne substituted benzophenone.

Synthesis of compound 3. To a solution of zinc powder (195 mg, 3 mmol) in dry THF (30 mL), $TiCl_4$ (285 mg, 164 μL, 1.5 mmol) was added slowly at −5° C. under $N_2$ protection. The resulting mixture was then stirred at room temperature for 0.5 hour and refluxed for another 2.5 hours. The temperature was decreased to −5° C. again, and pyridine (59 mg) was added. After reacting at −5° C. for 10 minutes, a mixture of Compound 4 (303 mg, 1 mmol) and 4,4'-bis (diethylamino)benzo-phenone (357 mg, 1.1 mmol) in THF (10 mL) was added dropwise. Then, the mixture was stirred under reflux overnight. After cooling to room temperature, saturated $K_2CO_3$ aq was added and the mixture was extracted with DCM (50 mL×3). The combined organic phase was concentrated and separated with chromatography (hexane/DCM=4/1) to give the product as yellow solid (320 mg, 54%). $^1$H NMR (400 MHz, THF-d8) δ 0.23 (s, 9H), 1.10-1.16 (m, 12H), 3.31-3.35 (m, 8H), 6.40-6.42 (d, J=8.8 Hz, 2H), 6.45-6.47 (d, J=8.8 Hz, 2H), 6.83-6.86 (m, 4H), 7.00-7.04 (m, 7H), 7.2 (d, 3H). $^{13}$C NMR (100 MHz, THF-d8) δ 1.3, 12.0, 24.0, 24.2, 24.3, 24.5, 24.7, 43.9, 88.2, 89.3, 110.3, 110.5, 117.5, 125.4, 127.5, 130.4, 130.5, 131.5, 131.6, 131.7, 132.7, 132.8, 134.7, 143.4, 145.1. HRMS (MALDI-TOF), m/z: $[M+H]^+$ calcd: 595.3503, found: 595.3511.

Synthesis of compound 2. A mixture of Compound 3 (250 mg, 0.42 mmol) and $K_2CO_3$ (348 mg, 2.52 mmol) in THF/MeOH (15/3 mL) was stirred at room temperature for 4 hours. Removing the solvents under reduced pressure, the solid was re-dissolved in DCM and washed with brine. The organic phase was then concentrated, giving the pure product as yellow solid (218 mg, 99%). $^1$H NMR (400 THF-d8, δ): 0.23 (s, 9H), 1.09-1.16 (m, 12H), 3.20 (s, 1H), 3.31-3.36 (m, 8H), 6.40-6.47 (m, 4H), 6.82-6.85 (m, 4H), 7.00-7.09 (m, 7H), 7.23 (d, 2H). $^{13}$C NMR (100 MHz, THF-d8, δ): 12.0, 24.0, 24.1, 24.3, 24.5, 24.7, 43.8, 67.8, 72.5, 73.1, 75.0, 110.4, 110.5, 117.3, 125.4, 127.5, 130.4, 130.5, 131.5, 131.7, 132.7, 132.8, 134.7, 143.4, 145.1, 146.5, 146.7, 147.6. HRMS (MALDI-TOF), m/z: $[M]^+$ calcd: 522.3035, found: 522.3037.

Synthesis of compound 2TPE-4E. To the DMSO solution (7 mL) of Compound 2 (100 mg, 0.19 mmol), CuCl (4 mg, 20%) was added and stirred at 80° C. for 8 hours. After cooling to room temperature, red solid was precipitated and collected by filtration. The product was purified by chromatography, affording the pure product as red solid (63 mg, 62%). $^1$H NMR (400 THF-d8, δ): 1.11-1.14 (m, 24H), 3.34 (br, 16H), 6.40-6.47 (m, 8H), 6.84 (br, 8H), 7.03-7.10 (m, 14H), 7.28-7.30 (m, 2H). $^{13}$C NMR (100 MHz, THF-d8, δ): 12.0, 24.0, 24.1, 24.4, 24.6, 24.8, 43.9, 63.7, 73.5, 78.9, 110.3, 110.5, 116.2, 125.5, 127.5, 130.3, 130.4, 131.5, 131.9, 132.3, 132.7, 132.8, 134.5, 143.9, 145.0, 146.5, 146.8. HRMS (MALDI-TOF), m/z: $[M]^+$ calcd: 1042.5913, found: 1042.5938.

Synthesis of compound TPETA-BT2E. Under $N_2$, a mixture of alkynyl precursor (50 mg, 0.079 mmol), $Pd(OAc)_2$ (1 mg, 0.0045 mmol), $^nBu_4NBr$ (14.5 mg, 0.045 mmol), $K_2CO_3$ (10.9 mg, 0.079 mmol), 2.5 mL DMF, 1.3 mL $H_2O$ and 3.8 mL iPrOH was refluxed for 16 hours. The mixture was then evaporated to dryness under reduced pressure. The crude product was purified by silical gel column chromatography using DCM/hexane (v/v=1/2) as eluent to afford 2DATPE-BT (37.5 mg, 85.8%)$^1$H NMR (400 THF-d8, δ): 7.71-7.69 (d, 1H), 7.29-7.25 (m, 2H), 7.20-7.01 (m, 19H), 6.98-6.92 (m, 2H), 6.80-6.78 (d, 2H).

Photophysical Properties

Figure 7A:
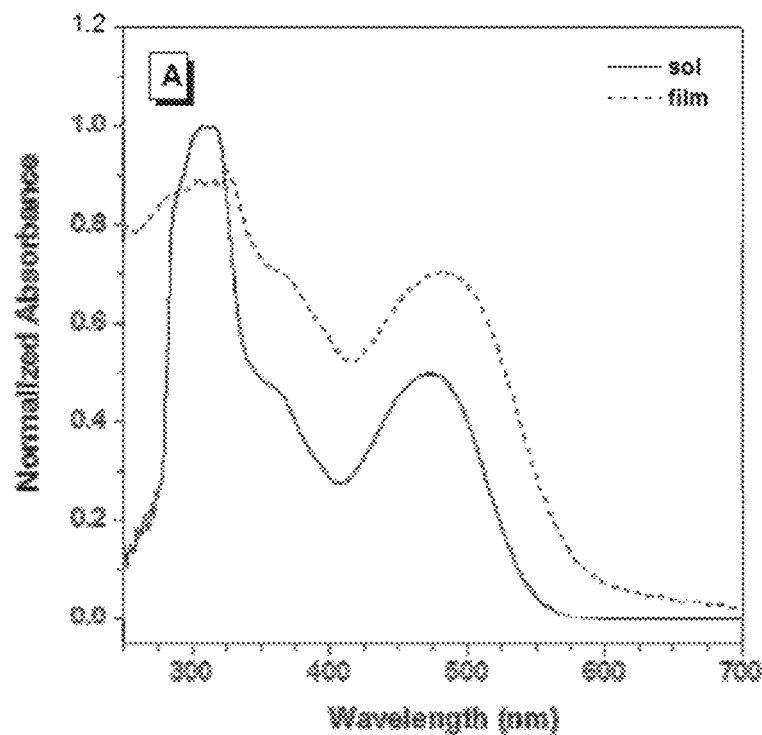
FIG. 7A-C shows (A) UV spectra of 2TPE-4E in THF and thin film. (B) PL spectra of 2TPE-4E in THF and thin film (C) in acetonitrile/water mixtures with different fractions ($f_W$). Concentration: 20 μM. (C) PL spectra of PL spectra of 2TPE-4E in THF/water mixtures with different fractions ($f_W$) (Concentration: 10 μM); and the plot of emission maximum in wavelength and relative emission intensity ($I/I_0$) vs. the composition of aqueous mixture.
Figure 7B:
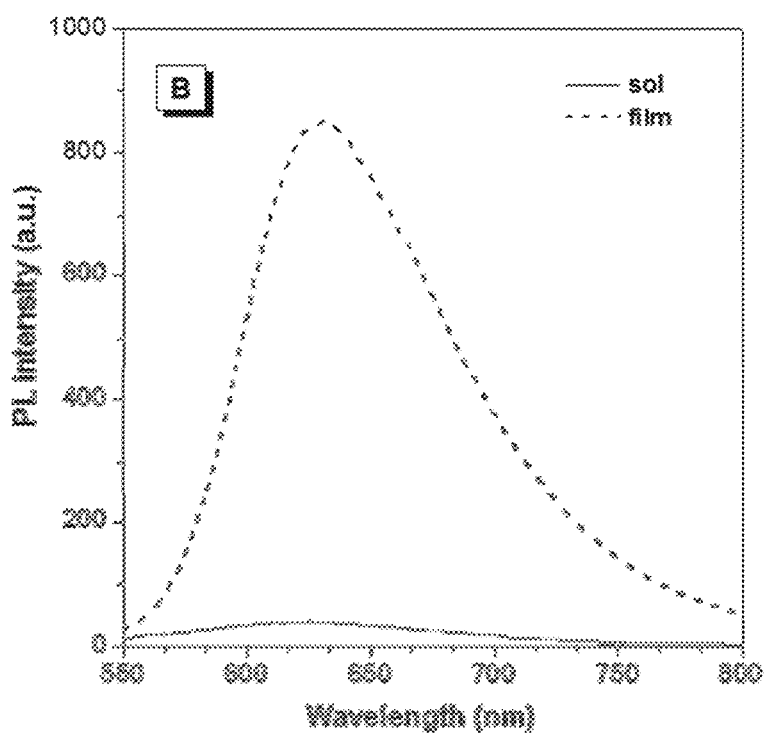

The photophysical properties of 2TPE-4E were investigated by UV-vis (FIG. 7A) and photoluminescence (PL) spectra. (FIG. 7B) Interestingly, 2TPE-4E shows a much longer absorption wavelength (maximum absorption: 473 nm). Additionally, both in dilute THF solution (concentration: $7 \times 10^{-6}$ M) and thin film, 2TPE-4E shows strong absorption with two absorption peaks at about 310 nm and 473 nm, respectively, with a molar extinction coefficient (E)

of about $7 \times 10^4$ $M^{-1}$ $cm^{-1}$. The high ε means 2TPE-4E could be excited by a weak laser power, which is beneficial for bio-application due to the weak photo-damage and photo-bleaching.

Figure 7C:
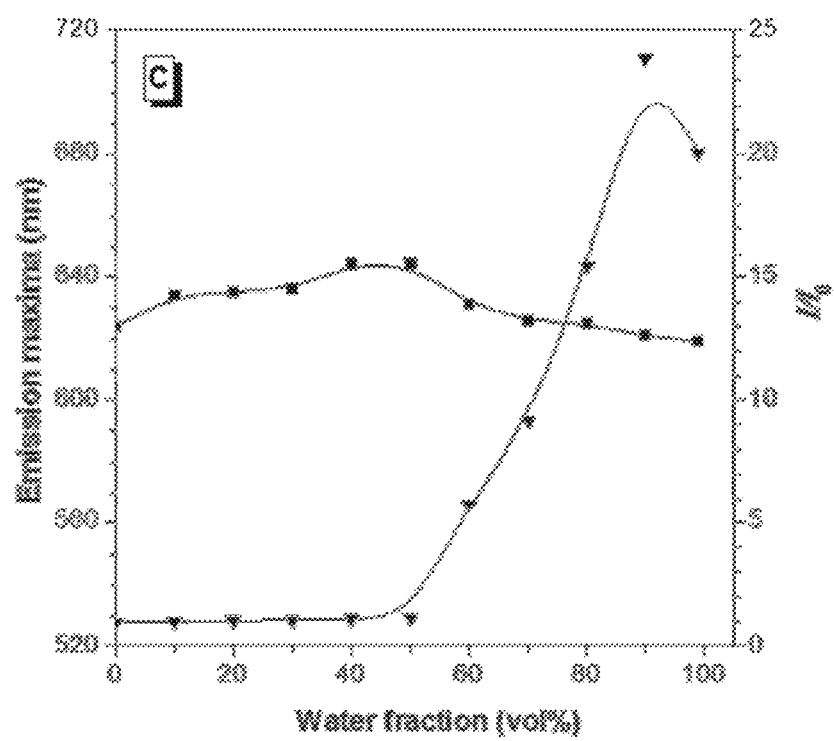

The photoluminescence (PL) behaviors of 2TPE-4E in dilute THF solution and thin film were investigated as shown in FIG. 7C. As expected, 2TPE-4E shows a much longer solid emission wavelength (630 nm). Although the film of 2TPE-4E looked bright, its quantum yield (QY) was measured to be around 6%, which can probably be ascribed to the high molar extinction coefficient. In dilute THF solution, 2TPE-4E shows very weak emission which could be explained by the rotation of TPE moieties and octatetrayne. With the water fraction ($f_w$) increasing, 2TPE-4E began to aggregate and gave a highest intensity at a $f_w$ of 90% due to the restriction of intramolecular rotation.

AIE Dots and mAb-AIE Dots

Preparation

AIE dots based on 2TPE-4E were prepared through a nano-precipitation method using DSPE-$PEG_{2000}$ and DSPE-PEG-COOH as the encapsulation matrix (FIG. 8A). Driven by the hydrophilic and hydrophobic interaction, DSPE will intertwine with 2TPE-4E to form the hydrophobic core, while the hydrophilic PEG segment will self-assemble to form the outside layer with surface carboxyl groups for further modification. Through dehydration between the carboxyl groups on the surface of AIE dots and the amino groups of cetuximab, antibody conjugated AIE dots (mAb-AIE dots) were finally afforded and purified by using an Amicon Ultra-4 centrifugal filter. The amount of 2TPE-4E encapsulated in mAb-AIE dots was determined from the standard curve, which gives the encapsulation concentration of 15.2 µg $mL^{-1}$. The particle size of mAb-AIE dots was evaluated by dynamic light scattering (DLS), giving an average hydrodynamic diameter of about 117 nm with a polydispersity index (PDI) of 0.25. The AIE dots fabrication and cell incubation details are presented as follows:

Preparation of 2TPE-4E loaded AIE dots: THF solutions of 2TPE-4E (3 mg/mL), DSPE-PEG (3 mg/mL), and DSPE-PEG-COOH (3 mg/mL) were first prepared for later use. Then, 300 µL 2TPE-4E, DSPE-PEG, DSPE-PEG-COOH solution and 100 µL THF were mixed together, giving 1 mL mixture. 9 mL dd $H_2O$ was added to the mixture, followed by sonicating the mixture for 1 minute at 25 W output using a microtip probe sonicator (XL2000, Misonix Incorporated, NY). The mixture was then stirred at room temperature overnight to evaporate the organic solvent. The suspension was further filtered with a 0.22 µm syringe filter to obtain AIE dots.

Conjugation of antibody to 2TPE-4E loaded AIE dots: Cetuximab was conjugated to the surface of AIE dots through the following procedure. A 2 mL 2TPE-4E loaded AIE dots aqueous solution was added to 6 mL dd $H_2O$ under stirring. 40 µL cetuximab (5 mg/mL) was then added to the mixture followed by 20 µL EDC (5 mg/mL) and 20 µL NHSS (5 mg/mL). The mixture was stirred for 4 hours and then purified by using Amicon Ultra-4 centrifugal filters. The antibody conjugated AIE dots were stored at 4° C. for further use.

Preparation of org-5 loaded AIE dots: THF solutions of org-5 (3 mg/mL), DSPE-PEG (3 mg/mL), and DSPE-PEG-COOH (3 mg/mL) prepared firstly for later use. Then, 300 µL org-5, DSPE-PEG, DSPE-PEG-COOH solution and 100 µL THF were mixed together, giving 1 mL mixture. 9 mL dd $H_2O$ was added to the mixture, followed by sonicating the mixture for 1 minute at 25 W output using a microtip probe sonicator (XL2000, Misonix Incorporated, NY). The mixture was then stirred at room temperature overnight to evaporate the organic solvent. The suspension was further filtered with a 0.22 µm syringe filter to obtain AIE dots.

Conjugation of antibody to org-5 loaded AIE dots: Cetuximab was conjugated to the surface of AIE dots through the following procedure. 2 mL org-5 loaded AIE dots aqueous solution was added to 6 mL dd $H_2O$ under stirring. 40 µL cetuximab (5 mg/mL) was then added to the mixture followed by 20 µL EDC (5 mg/mL) and 20 µL NHSS (5 mg/mL). The mixture was stirred for 4 hours and then purified by using Amicon Ultra-4 centrifugal filters. The antibody conjugated AIE dots were stored at 4° C. for further use.

Figure 13A:
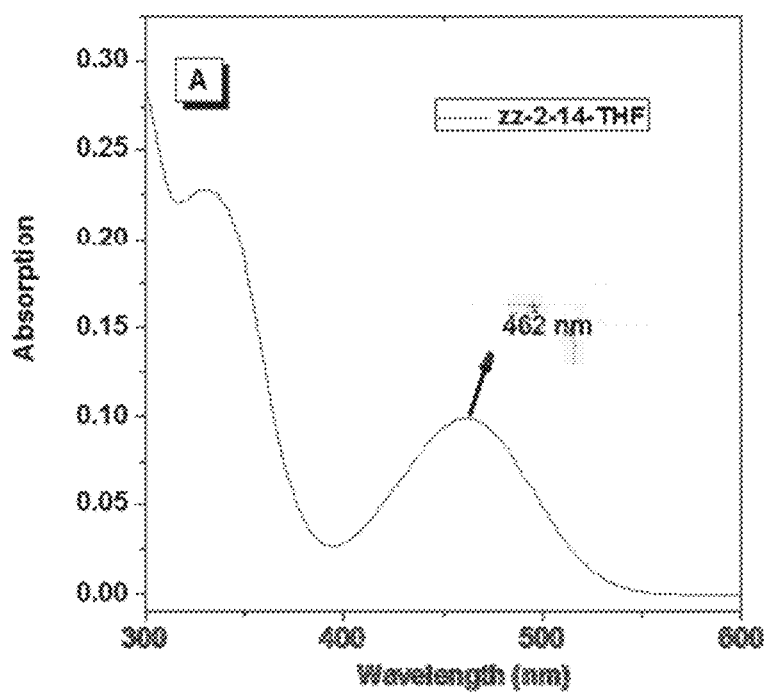
FIG. 13A-C shows photophysical properties of org-5.
Figure 13B:
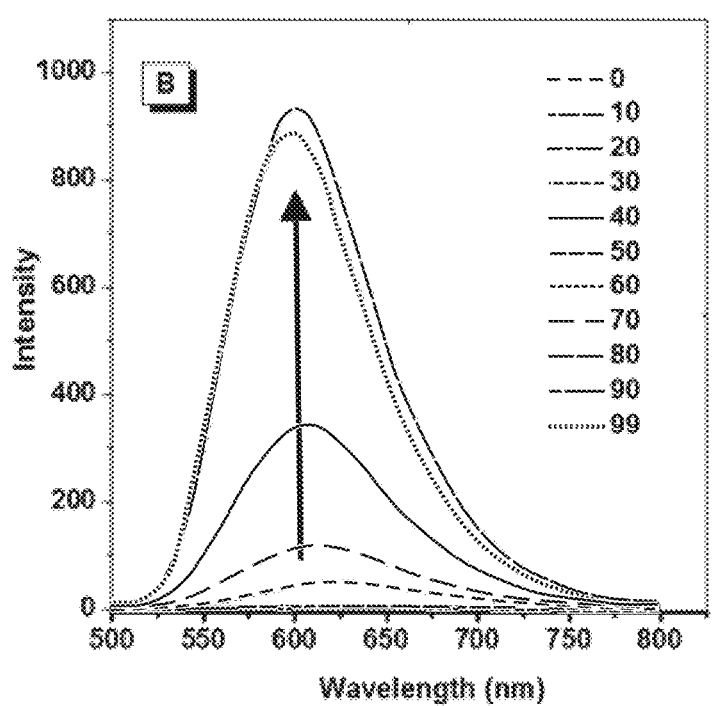
Figure 13C:
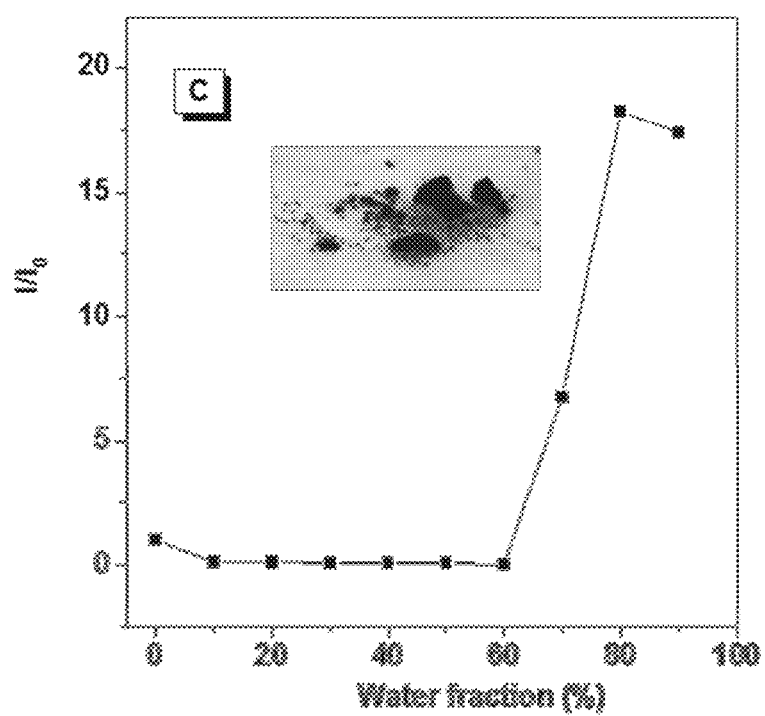
Figure 15A:
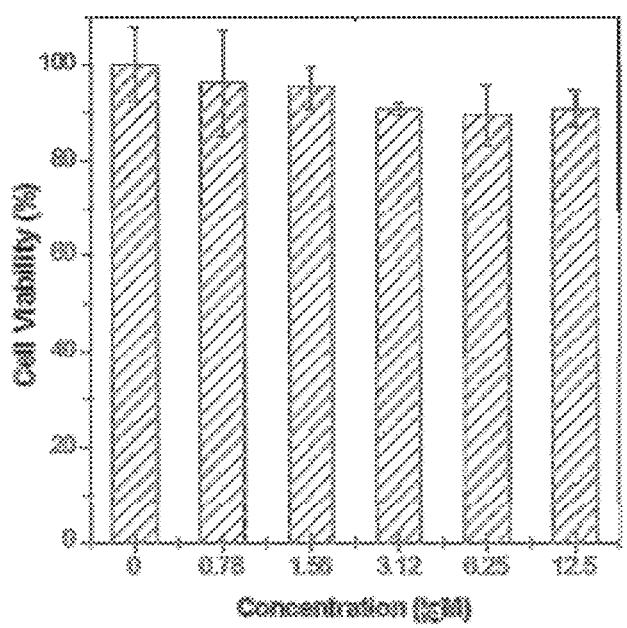
FIG. 15A-C shows cell viability of A) HCC 827, B) NCI-H23, and C) HLF cells upon treatment with different concentrations of org-5-mAb-AIE dots.
Figure 15B:
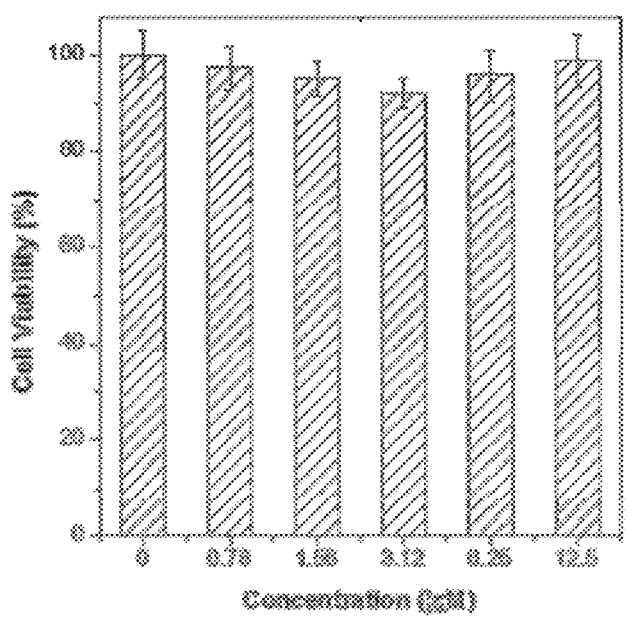
Figure 15C:
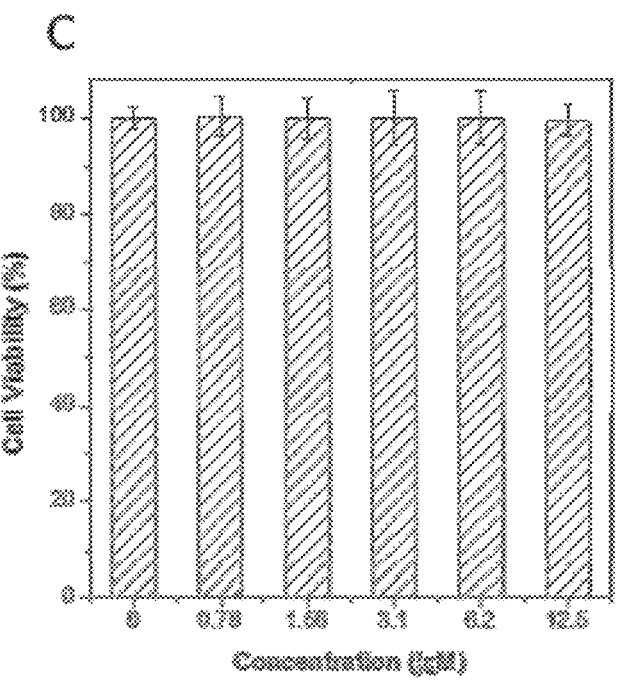

Further, in FIG. 13, the UV spectra of org-5 (FIG. 13A), PL spectra of 2TPE-4E (FIG. 13B), and emission intensity of org-5 (FIG. 13C) are shown. In FIG. 14, the confocal images of HCC 827, H23, and HLF cells after incubation with antibody targeted AIE dots based on org-5 for 8 hours (FIG. 14A); and flow cytometry histograms of HCC 827, H23, and HLF cells after incubation with AIE dots at 37° C. for 8 hour (FIG. 14B) are shown. In FIG. 15, the cell viability of HCC 827 (FIG. 15A), H23 (FIG. 15B), and HLF (FIG. 15C) cells upon treatment with different concentrations of AIE dots is shown.

Cell culture: HCC-827, NCI-H23, MDCK-2, and NIH-3T3 cells were purchased from ATCC. The first two cell lines were cultured in RPMI-1640 with 1% penicillin-streptomycin and 10% FBS, while the other two were cultured in Dulbecco's Modified Eagle's Medium with 1% penicillin-streptomycin and 10% FBS at 37° C. in a humidified incubator with 5% $CO_2$. The culture medium was changed every 2 days, and cells were collected by treating with 0.25% trypsin-EDTA solution after reaching confluence.

To verify whether the antibody successfully conjugated with AIE dots, a cell stain experiment was performed by incubating HCC-827 cells (non-small lung cancer cells overexpressing EGFR) with mAb-AIE dots and AIE dots, respectively. As shown in FIG. 8B-D, upon incubation of HCC-827 cells with mAb-AIE dots for 8 hours at room temperature, a strong red fluorescence signal was observed in the cytoplasm of HCC-827 cells. However, at the same conditions, no obvious fluorescence was observed in HCC-827 cells when using non-conjugated AIE dots as a probe (FIG. 8E-G). This not only indicates that the antibody was successfully conjugated with AIE-dots, it also demonstrates the cancer cell targeting ability of the mAb-AIE dots.

Receptor blocking experiments were implemented to further confirm the antibody dependent targeting. First, free antibody C225 was incubated with HCC-827 cells to block off receptors on the cell surface, then mAb-AIE dots were added. No obvious fluorescence signal could be observed in the HCC-827 cells (FIG. 8H-J). The data unambiguously demonstrates that the antibody may play a key role in targeted imaging of lung cancer cells.

Specificity of mAb-AIE Dots to HCC-827 Cells

To test the targeting specificity of the mAb-AIE dots, the mAb-AIE dots were then incubated with HCC-827, MDCK-2, NIH-3T3, and NCI-H23 cells simultaneously. As shown in FIG. 9, only HCC-827 cells with overexpression of EGFR exhibit strong red fluorescence signals, while the normal cells (MDCK-2 and NIH-3T3 cells) and the cancer cells with low EGFR expression (NCI-H23 cells) show very weak fluorescence signals after incubating by mAb-AIE dots with the same concentration and time. This demonstrates the exceedingly high cancer cell targeting specificity of the mAb-AIE dots.

In addition, the specificity of the mAb-AIE dots probe was also confirmed by flow cytometry analysis (FIG. 9I). Confocal images of HCC-827 (FIG. 9A, E), NCI—H23 (FIG. 9B, F), NIH-3T3 (FIG. 9C, G), and MDCK-2 cells (FIG. 9D, H) are shown in bright-field and fluorescence after incubation with AC-AIE dots for 8 hours. As shown in FIG. 9, the labeling ratio for HCC-827 cells is much higher than that of the other cell lines and the control after 8 hours incubation.

Photostability and Biocompatibility of mAb-AIE Dots and Imaging Guided Therapy

High photostability and biocompatibility are necessary characteristics of fluorescent visualizer for bio-imaging, which allows a prolonged imaging process with attenuated photobleaching. To evaluate the photo-bleaching resistance of mAb-AIE dots, a confocal fluorescence microscope was used to continuously scan the mACb-AIE dots and LysoTracker Red labeled HCC-827 cells, respectively. Images of HCC-827 cells cultured by AC-AIE dots are shown in FIG. 10A-C, while the HCC-827 cells cultured by LysoTracker-Red are shown in FIG. 10D-F, upon laser scanning with different scanning times. As shown in FIG. 10G, there was only 20% fluorescence signal loss for mAb-AIE dots at a total irradiation time of 875 seconds. In contrast, more than 60% of the fluorescence of the LysoTracker-Red is lost after the same irradiation time. Therefore, mAb-AIE dots show a much higher photostability.

Figure 11:
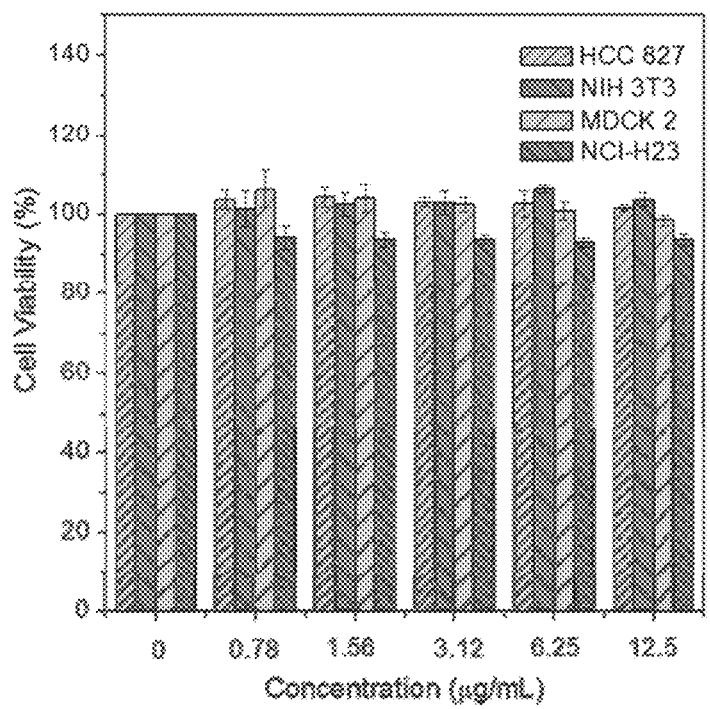
FIG. 11 shows cell viability of HCC 827, NIH 3T3, MDCK 2, and NCI-H23 cells upon treatment with different concentrations of mAb-AIE dots.

In addition, mAb-AIE dots shows very small cytotoxicity to cells through a standard CCK-8 assay, demonstrating its biocompatibility (FIG. 11). The cell viability of HCC 827, NIH 3T3, MDCK 2, and NCI-H23 cells upon treatment with different concentrations of mAb-AIE dots is shown in FIG. 11.

Figure 12:
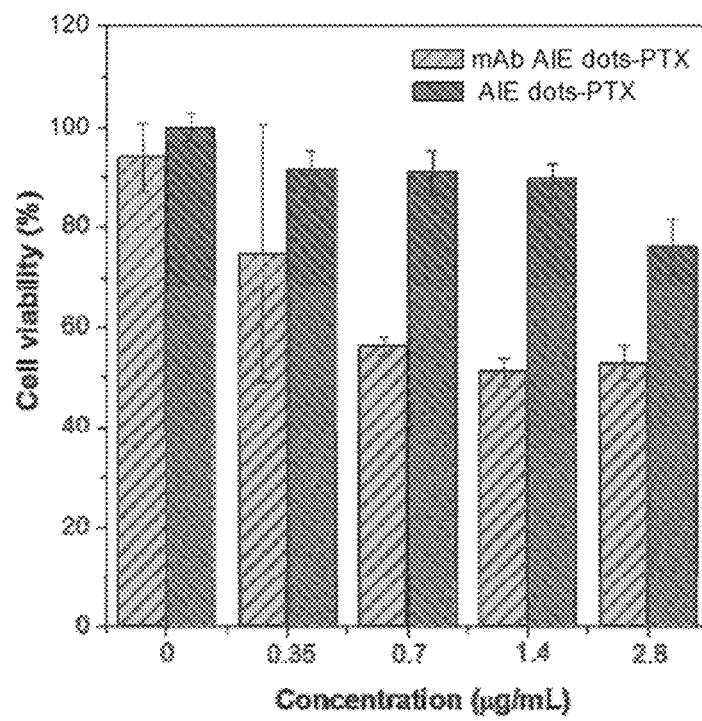
FIG. 12 shows cell viability of HCC 827 cells upon treatment with different concentrations of AIE dots-PTX and mAb-AIE dots-PTX.

Based on the specific binding ability of mAb-AIE dots to HCC-827 cells, the application of mAb-AIE dots in imaging guided therapy was explored (FIG. 12). By encapsulating the AIEgens and chemotherapeutic drug (Paclitaxel, PTX) simultaneously into the AIE dots, two kinds of AIE dots were prepared, namely mAb-AIE dots-PTX and AIE dots-PTX with and without C225 modification, respectively. Compared to the AIE dots-PTX, mAb-AIE dots-PTX show better lung cancer cell killing ability due to the stronger binding effect of the mAb-AIE dots-PTX towards EGFR overexpressed HCC-827 cells.

Preparation of Aptamer AIE-Dots

Figure 16:
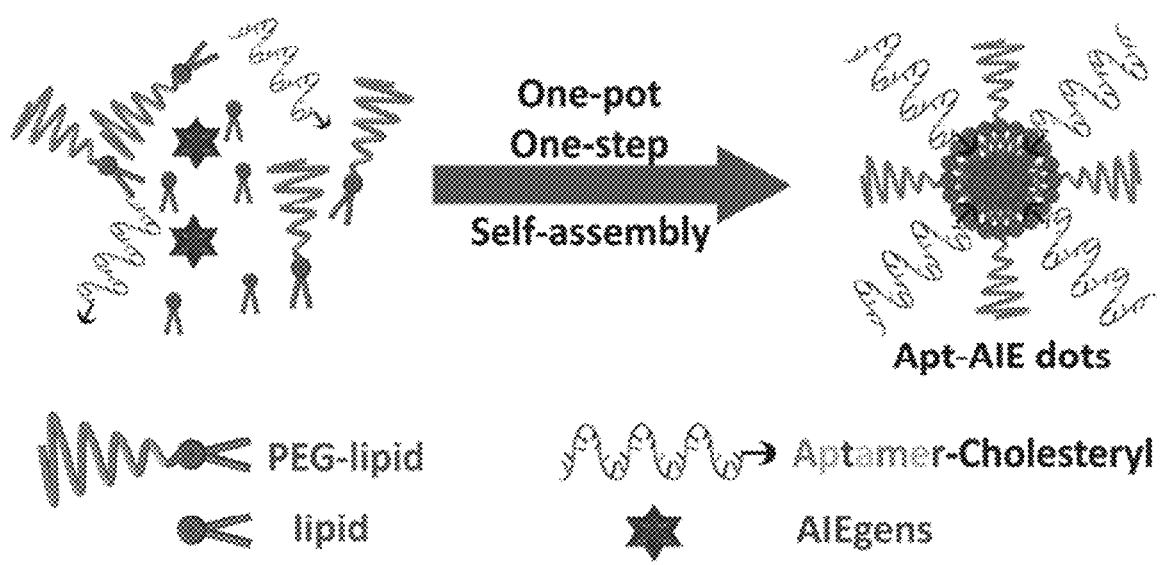
FIG. 16 shows the scheme of the fabrication of aptamer AIE dots.

The scheme of the fabrication of aptamer AIE dots is shown in FIG. 16.

Fabrication of aptamer AIE-dots: Stock solutions of 10 mg/ml of AIEgens (1-50%), DPPC (1-90%), cholesterol (1-90%), and mPEG2000-DSPE (1-90%) in chloroform were mixed in a scintillation vial. This mixture was blown dry with $N_2$ and further dried under vacuum overnight. After complete evaporation of the chloroform, the residue was heated at 80° C. The preparation buffer contained 25 mM 2-[4-(2-hydroxyethyl)-1-piperazinyl]-ethane sulfonic acid (HEPES, pH 7.4), 150 mM NaCl, 5 mM KCl, 1 mM $MgCl_2$, and 1 mM $CaCl_2$. The buffer solution (100-5000 μL) was added to the dry lipids and followed by addition of 1-100 nmol of cholesterol-tagged DNA. After the mixture was incubated for 1-6 hours at 10-80° C., and further incubated for 10-30 minutes at 10-37° C. during the sonication, the final product was stocked at 4° C.

Cell culture: MCF-7, A549, and 293T cells were purchased from ATCC. The first two cell lines were cultured in RPMI-1640 with 1% penicillin-streptomycin and 10% FBS, while the other two ones were cultured in Dulbecco's Modified Eagle's Medium with 1% penicillin-streptomycin and 10% FBS, at 37° C. in a humidified incubator with 5% $CO_2$. The culture medium was changed every 2 days, and the cells were collected by treating with 0.25% trypsin-EDTA solution after reaching confluence.

Specificity and Biocompatibility of Aptamer AIE-Dots to MCF-7 and A549 Cells

To determine the specificity of as-prepared AIE-dots for targeting nucleolin, cancer cell lines and normal healthy cells were incubated with aptamer AIE-dots and AIE-dots, separately. Non-limiting examples of cancer cell lines used include MCF-7 (human breast cancer cell line) and A549 cells (human lung cancer cell line). The normal healthy cells used were 293T cells (a human lung epithelial normal cell line).

Figure 17:
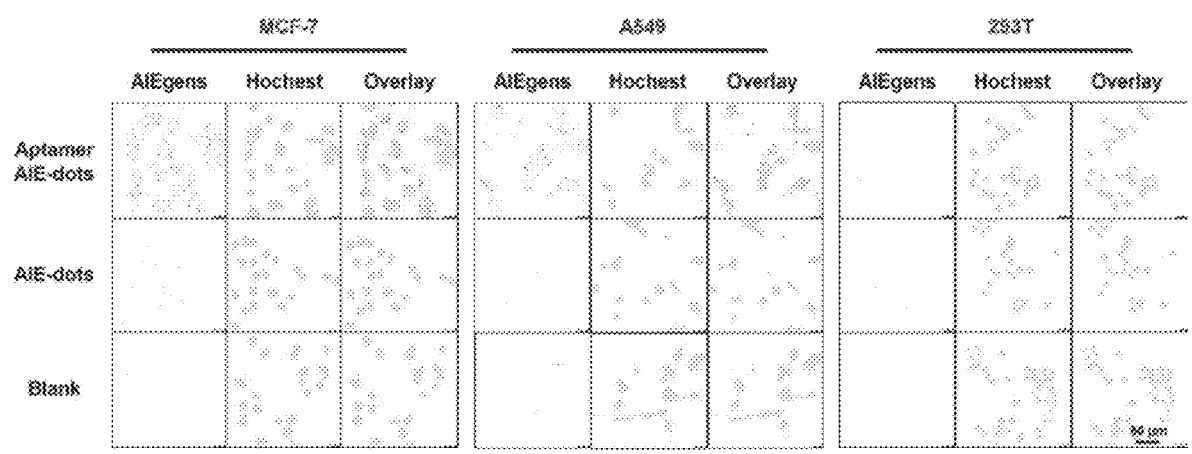
FIG. 17 shows confocal images of MCF-7, A549, and 293T cells after incubation with aptamer AIE dots for 1 hour.

The fluorescence of the treated cells was collected using laser confocal fluorescence microscopy and flow cytometry. As illustrated in FIG. 17, MCF-7 cells (the breast cancer cell line) and A549 cells (the lung cancer cell line) treated with aptamer AIE-dots were highly fluorescent when compared to those treated with the control. In contrast, in 293T cells (the normal healthy cell line), aptamer AIE-dots showed undetectable fluorescence intensity and there was no significant difference relative to the control.

Figure 18A:
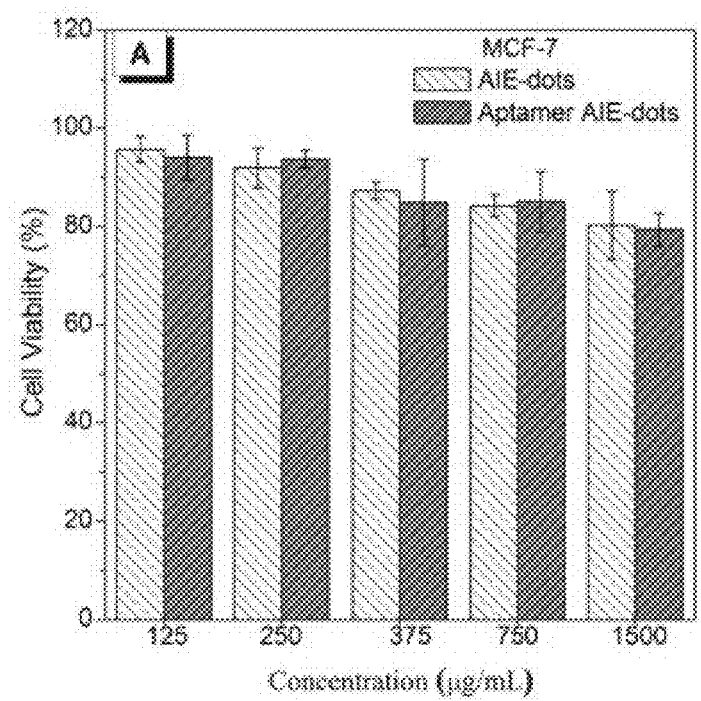
FIG. 18A-C shows cell viability of (A) MCF-7, (B) A549, and (C) 293T cells upon treatment with different concentrations of aptamer AIE dots.
Figure 18B:
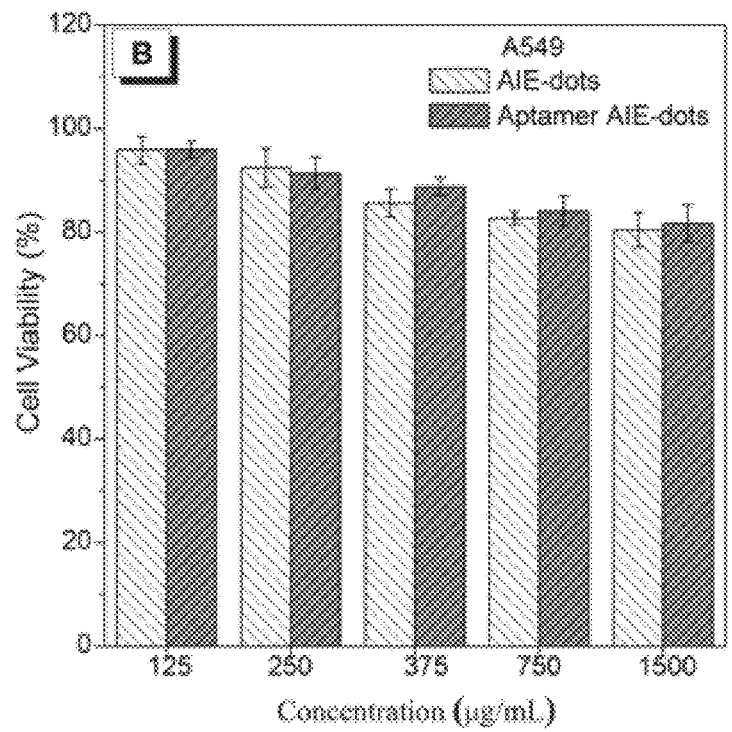
Figure 18C:
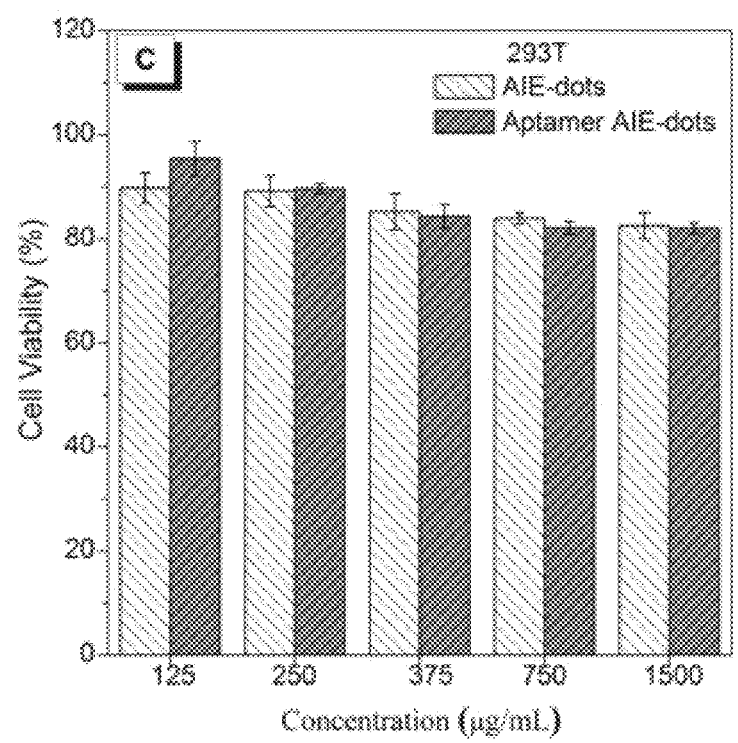

Results demonstrated the enhanced binding of aptamer AIE-dots to the nucleolin-overexpressed cancer cells (MCF-7 cells and A549 cells) compared with the normal cells (293T). Aptamer AIE-dots also demonstrate biocompatibility, as shown by the very small cytotoxicity to several cells through a standard CCK-8 assay (FIG. 18).

Antibody Probes

A fluorescent antibody probe may be clinically useful in at least the following non-limiting scenarios, such as in fluorescence guided surgery, endoscopic molecular imaging, and photodynamic therapy. Due to the high target to background ratio, which allows for a higher image contrast of cancer cells to normal cells, "turn-on" antibody probes are superior to conventional "always-on" antibody probes.

In addition, AIEgens have demonstrated advantages in biological applications, particularly selectivity, brightness, photostability, biocompatibility, and ease in functionalization. In this regard, luminogens in a molecularly dissolved state emit weak fluorescence but became highly emissive at high concentrations or in an aggregated state. Fluorescent materials having AIE characteristics have been developed and explored in many applications, including electronic devices, bio-imaging, and therapeutic treatment. Although AIEgens have been used for many different bio-applications, antibody labeling has remained unexplored, as most AIEgens are highly hydrophobic and form aggregates in aqueous solution, thereby reducing the possibility of conjugation with antibodies. Furthermore, most AIEgens give absorption and emission in blue to green regions, which discourages penetration due to the scattering and absorption in tissue, limiting the monitoring in deep regions. Therefore, the design and exploration of new AIEgens for antibody labeling and "turn-on" probes are desirable.

In the present subject matter, a new "turn-on" strategy for preparing antibody probes was developed based on AIE properties. Water-soluble luminogens with aggregation-induced emission characteristics (AIEgens) were designed and functionalized for antibody labeling. In particular, one non-limiting example of an AIEgen design is CSPP, which is (Z)-4-(4-(2-cyano-2-(4-(1-methylpyridin-1-ium-4-yl)phenyl)vinyl)phenyl)-1,1-dimethylpiperazin-1-ium iodide. In the design, a hydrophilic pyridium (Py) group serves as a strong electron-withdrawing group, a piperazine group serves as an electron-donating group, and α-Cyanostilbene was selected for attributing AIE characteristics. The red-emissive AIEgen was utilized for antibody labeling, enjoying the non-limited properties of wash-free imaging, high image contrast, long-term cellular retention, good photostability and biocompatibility.

Cetuximab, a monoclonal antibody, was used as a model for bio-conjugation. The mAb-AIEgen conjugate was AIE-active, and its fluorescence emission was attributed to "turn-on" properties controlled by antibody degradation after internalization through EGFR-mediated endocytosis. Thus, the mAb-AIEgen conjugate selectively stains cells with EGFR overexpression, such as the non-limiting example of HCC827 cells. The mAb-AIEgen conjugate also possesses good photostability and long-term cellular retention, which enables the conjugate to be used as a long-term cell tracker. The mAb-AIEgen conjugates may also be used for the non-limiting application of wash-free and "turn-on" imaging of specific cancer cells, which allow for high image contrast and low background signal.

A probe according to the present subject matter shows good biocompatibility, photostability, long-term cellular retention, and specificity to mitochondria. As such, there are a broad range of applications for the new strategy of preparing "turn-on" protein-AIEgen probes according to the present subject matter, such as non-limiting examples of cancer diagnosis with high TBR, cancer therapy, and tracking cell dynamics in real time, among others.

In an embodiment, the present subject matter is directed to an AIEgen comprising: a hydrophilic pyridium group as a strong electron-withdrawing group; a piperazine group as an electron-donating group; and a α-Cyanostilbene; wherein the AIEgen exhibits aggregation induced emission.

In an embodiment, the AIEgen of the present subject matter is CSPP having a structure of

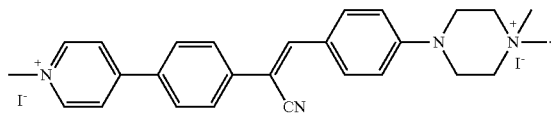

In an embodiment, the AIEgen of the present subject matter is CSPP—NHS having a structure of

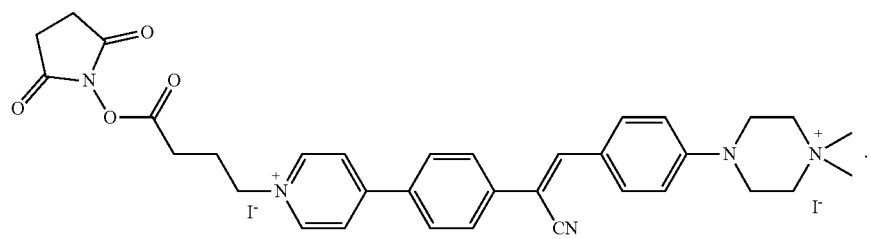

In an embodiment, the AIEgen of the present subject matter is used for turn-on imaging and wash-free imaging. In an embodiment, the AIEgen of the present subject matter exhibits specificity, resulting in image contrast. In an embodiment, the AIEgen of the present subject matter is used for long-term cellular retention. In an embodiment, the AIEgen of the present subject matter is used to target mitochondria. In an embodiment, the AIEgen of the present subject matter is used as a probe for antibody labeling.

In an embodiment, the present subject matter is directed to a method of synthesizing an AIEgen, comprising:
reacting

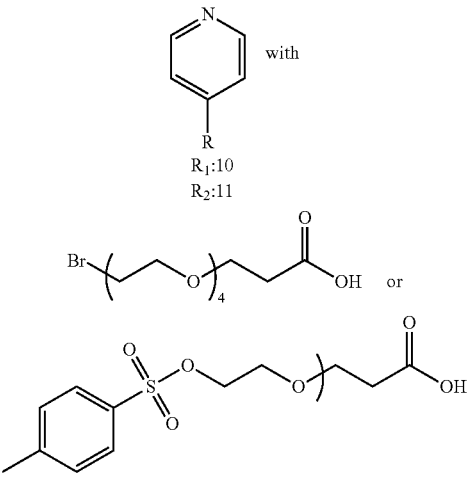

and toluene to obtain an intermediate; and
reacting the intermediate with DCC, NHS, and DMF to obtain the AIEgen;
wherein the intermediate is

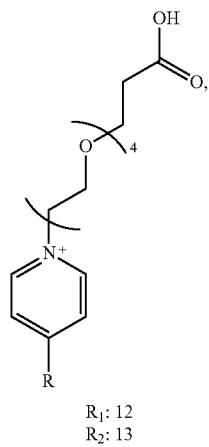

and the AIEgen is

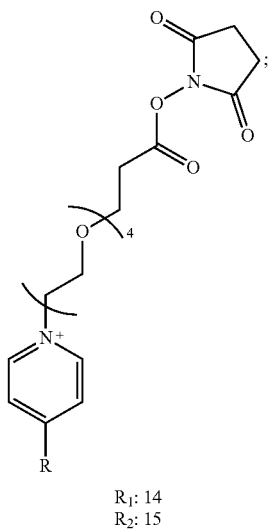

R₁: 14
R₂: 15 wherein R₁ comprises

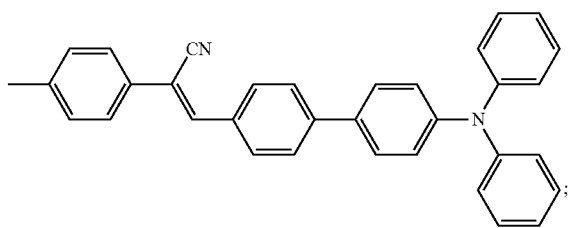 [SMILES: Cc1ccc(/C(C#N)=C/c2ccc(-c3ccc(N(c4ccccc4)c4ccccc4)cc3)cc2)cc1]

and
wherein R₂ comprises

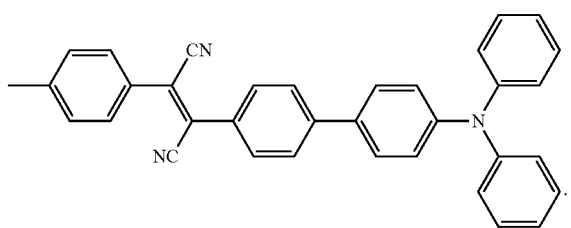 [SMILES: Cc1ccc(/C(C#N)=C(\C#N)c2ccc(-c3ccc(N(c4ccccc4)c4ccccc4)cc3)cc2)cc1]

In an embodiment according to the method of synthesizing an AIEgen of the present subject matter, the AIEgen is used for antibody-targeted photodynamic therapy.

In an embodiment, the present subject matter is directed to a method of labeling comprising incubating a subject having cells with a conjugate formed by conjugating an AIEgen with an antibody; and selectively labeling desired cells by turn-on imaging, wherein labeling occurs when the desired cells are selectively stained by fluorescent emission of the AIEgen upon degradation of the antibody after cellular internalization of the conjugate through endocytosis.

In an embodiment according to the method of labeling of the present subject matter, the method is used for labeling mitochondria, cancerous cells, long-term cellular tracking, and antibody-targeted photodynamic therapy.

Synthesis of CSPP and CSPP—NHS

The design and synthesis of the present subject matter was inspired by the simple design and synthesis of ASCP, which was further modified and the hydrophilicity was improved. To prevent denature of antibodies during conjugation, aqueous solution was used for the reaction. A water-soluble AIEgen having a long wavelength in absorption and emission was required. Piperazine (PZ) was introduced to the structure and served as the electron donating group and hydrophilic group; pyridium (Py) salt was kept as the strong electron withdrawing group and hydrophilic group; and α-Cyanostilbene was the core skeleton for attributing AIE characteristics. As such, a new AIEgen, CSPP, was synthesized by Knoevenagel condensation and Suzuki coupling and the targeted compound was successfully obtained. CSPP carries two positive charges, thus enjoying high water-solubility, and its donor-acceptor structure contributes to a long-wavelength absorption, as well as emission. The synthetic route to CSPP and CSPP—NHS is shown below, with the scheme of synthesis following.

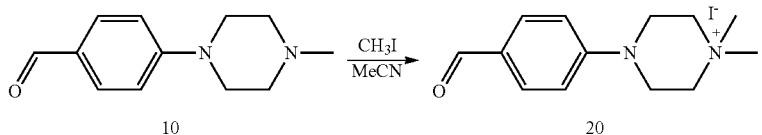

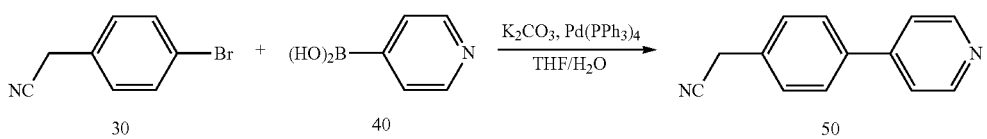

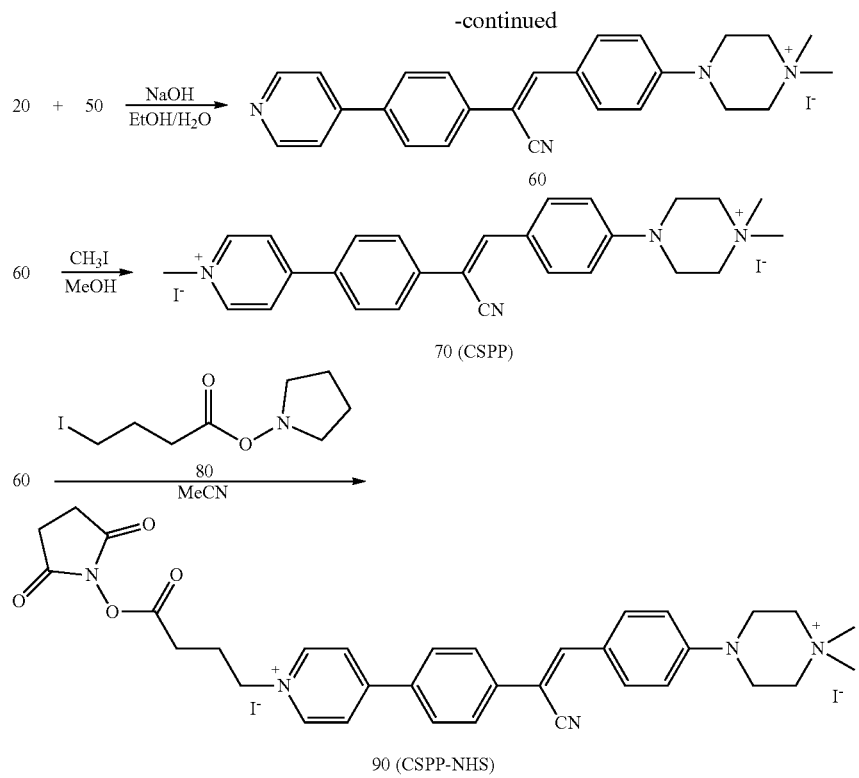

Synthesis of Compound 20: Into a 100 mL two-necked round bottom flask equipped with a condenser, was dissolved 10 (0.2 g, 0.98 mmol) in 15 mL acetonitrile. Iodomethane (0.15 mL) was then added and the mixture was heated to reflux for 4 hours. After cooling to room temperature, the mixture was poured into diethyl ether. The pale yellow precipitates formed were filtered by suction filtration. Yield: 95%. $^1$H NMR (400 MHz, DMSO-$d_6$), δ (ppm): 9.61 (s, 1H), 7.78 (d, 2H, J=8.8 Hz), 7.15 (d, 2H, J=8.8 Hz), 3.74 (t, 4H, J=4.4 Hz), 3.54 (t, 4H, J=4.8 Hz), 3.20 (s, 6H). $^{13}$C NMR (100 MHz, DMSO-$d_6$), δ (ppm): 190.5, 153.3, 131.2, 127.2, 113.8, 59.6, 50.2. HRMS (MALDI-TOF): m/z 219.1516 ($M^+$, calcd. 219.1497).

Synthesis of Compound 50: Into a 100 mL two-necked round bottom flask equipped with a condenser were added 2-(4-bromophenyl)acetonitrile (30, 0.50 g, 2.55 mmol), 4-pyridinylboronic acid (40; 0.31 g, 2.55 mmol), potassium carbonate (3.52 g, 25.5 mmol) and Pd(PPh$_3$)$_4$ (35 mg, 0.03 mmol) in 50 mL THF and 10 mL water under nitrogen. The mixture was stirred and heated to reflux overnight. After cooling to room temperature, the mixture was extracted with dichloromethane (DCM) three times. The organic phase was collected, washed with water and dried over anhydrous sodium sulfate. After solvent evaporation, the crude product was purified by silica-gel column chromatography using DCM/ethyl acetate (v/v=99:1) as eluent to furnish a white solid as product. Yield: 81%. $^1$H NMR (400 MHz, CDCl$_3$), δ (ppm): 8.69 (d, 2H, J=6.0 Hz), 7.67 (d, 2H, J=8.4 Hz), 7.51-7.46 (m, 4H), 3.83 (s, 2H). $^{13}$C NMR (100 MHz, CDCl$_3$), δ (ppm): 149.7, 146.7, 137.5, 130.2, 128.1, 127.1, 120.9, 116.9, 22.9. HRMS (MALDI-TOF): m/z 194.0914 ($M^+$, calcd. 194.0844).

Synthesis of Compound 60: Into a 50 mL round bottom flask were dissolved 50 (0.2 g, 1.03 mmol) and 20 (0.36 g, 1.03 mmol) in 8 mL ethanol and 2 mL water. Sodium hydroxide (41.2 mg, 1.03 mmol) in 2 mL ethanol water was then added slowly into the mixture. After stirring for 2 hours, the pale yellow precipitates were filtered, washed with cold ethanol and dried under reduced pressure. Yield: 87%. $^1$H NMR (400 MHz, DMSO-$d_6$), δ (ppm): 8.63 (d, 2H, J=6.0 Hz), 7.99 (s, 1H), 7.95-7.91 (m, 4H), 7.84 (d, 2H, J=8.4 Hz), 7.76 (d, 2H, J=6.0 Hz), 7.16 (d, 2H, J=8.8 Hz), 3.69 (t, 4H, J=4.8 Hz), 3.18 (s, 6H). $^{13}$C NMR (100 MHz, DMSO-$d_6$), δ (ppm): 150.1, 144.7, 137.3, 134.4, 131.4, 129.3, 127.6, 127.3, 125.8, 123.6, 121.0, 120.9, 114.1, 107.6, 59.7, 50.1. HRMS (MALDI-TOF): m/z 395.2261 ($M^+$, calcd. 395.2236).

Synthesis of Compound 70 (CSPP): Into a 100 mL two-necked round bottom flask equipped with a condenser, was dissolved 60 (50 mg, 0.096 mmol) in 5 mL acetonitrile. Iodomethane (0.1 mL) was then added and the mixture was heated to reflux for 4 hours. After cooling to room temperature, the mixture was poured into diethyl ether. The red precipitates formed were filtered by suction filtration. Yield: 97%. $^1$H NMR (400 MHz, DMSO-$d_6$), δ (ppm): 9.05 (d, 2H, J=6.8 Hz), 8.54 (d, 2H, J=6.8 Hz), 8.20 (d, 2H, J=8.8 Hz), 8.11 (s, 1H), 7.98-7.94 (m, 4H), 7.17 (d, 2H, J=9.2 Hz), 4.31 (s, 3H), 3.71 (d, 2H, J=4.8 Hz), 3.18 (s, 6H). $^{13}$C NMR (100 MHz, DMSO-$d_6$), δ (ppm): 145.2, 131.5, 131.2, 129.7, 128.8, 128.6, 126.1, 124.0, 123.7, 114.4, 59.8, 50.3, 40.6. HRMS (MALDI-TOF): m/z 537.1516 ($M^+$, calcd. 537.1515).

Synthesis of Compound 90 (CSPP—NHS): Into a 100 mL two-necked round bottom flask equipped with a condenser, was dissolved 60 (50 mg, 0.096 mmol) in 5 mL acetonitrile. 80 (36 mg, 0.1152 mmol) was then added and the mixture was heated to reflux until the spot of 60 on TLC plate disappeared. After cooling to room temperature, the mixture was poured into diethyl ether. The red precipitates formed were filtered by filtration and washed by cold ethanol. Yield:

72%. $^1$H NMR (400 MHz, DMSO-d$_6$), δ (ppm): 8.96 (d, 2H, J=6.8 Hz), 8.51 (d, 2H, J=6.8 Hz), 8.19 (d, 2H, J=8.8 Hz), 8.11 (s, 1H), 7.98-7.93 (m, 4H), 7.17 (d, 2H, J=9.2 Hz), 4.63 (t, 2H, J=6.4 Hz), 3.18 (s, 6H), 2.86 (t, 2H, J=7.2 Hz), 2.78 (s, 4H), 2.31 (t, 2H, J=7.6 Hz). $^{13}$C NMR (100 MHz, DMSO-d$_6$), δ (ppm): 170.6, 151.0, 144.6, 131.5, 131.2, 123.0, 128.7, 126.1, 124.3, 124.1, 114.4, 114.1, 103.7, 59.2, 50.2, 40.5, 36.5, 34.7, 28.6, 26.0. HRMS (MALDI-TOF): m/z 706.1880 (M$^+$, calcd. 706.1890).

Properties of CSPP

Figure 19:
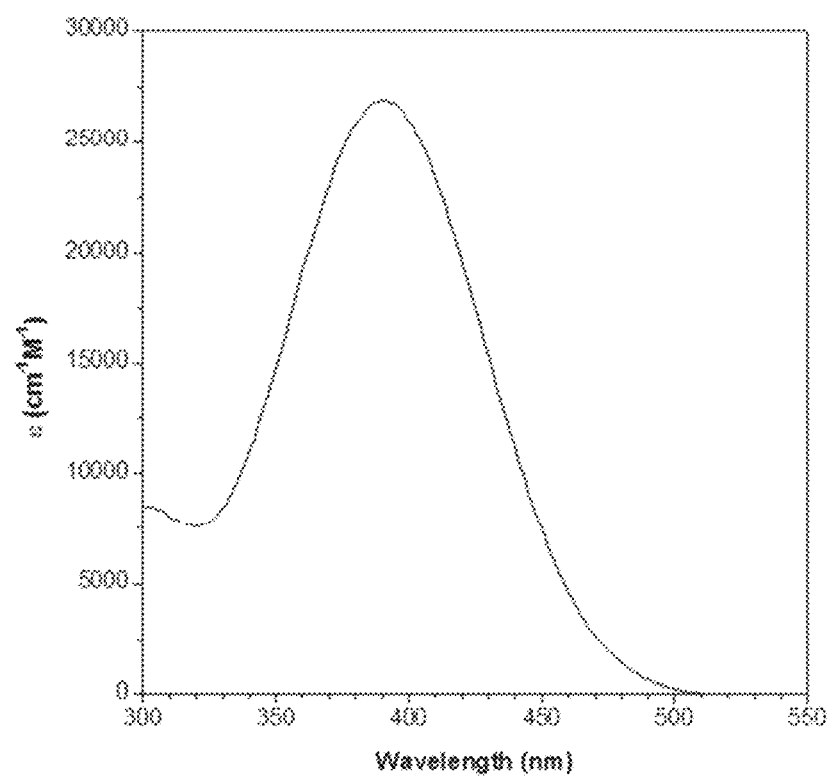
FIG. 19 shows absorption spectra of CSPP in water.

The photophysical properties of CSPP were studied. The absorption maximum was 395 nm in aqueous solution (FIG. 19) and showed very weak emission in pure water. However, the emission was enhanced at 640 nm in increments of isopropanol fraction (FIGS. 20a and b), which is a signature of AIE. The free intramolecular motion of a molecularly dissolved state in aqueous solution was in favor of non-radiative decay.

Figure 20:
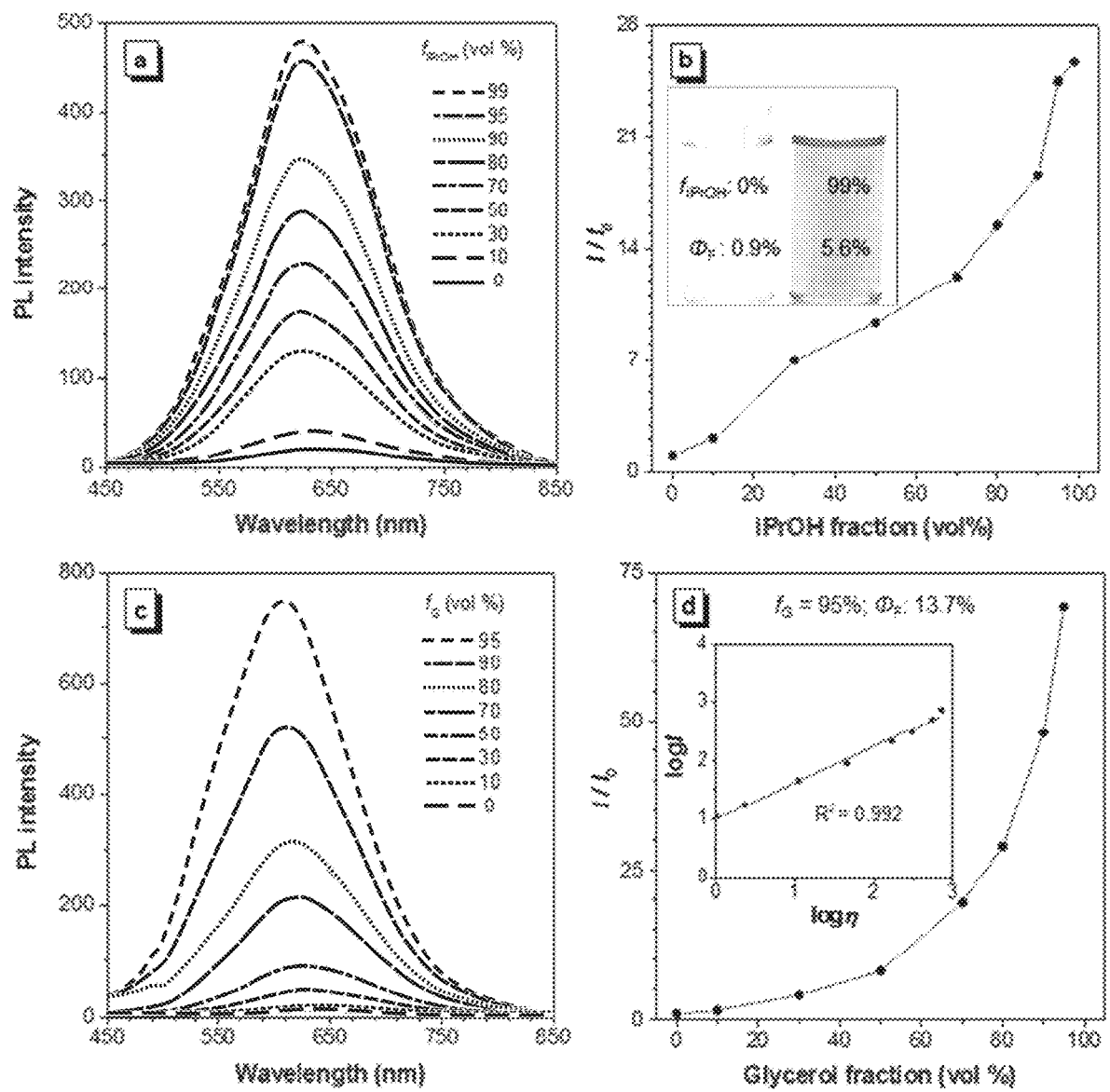
FIG. 20 shows (a) PL spectra of CSPP in water/iPrOH mixtures with different iPrOH fractions ($f_{iPrOH}$); (b) plot of relative intensity ($I/I_0$) at 640 nm versus $f_{iPrOH}$, where $I_0$ was the PL intensity in pure water. Inset: photographs of CSPP in water/iPrOH mixtures with 0% and 99% iPrOH fractions taken under 365 nm UV irradiation; (c) PL spectrum of CSPP in water/glycerol mixtures with different glycerol fractions ($f_G$); and (d) plot of $I/I_0$ at 620 nm versus $f_G$, where $I_0$ was the PL intensity in pure water. Inset: plot of log I against log η, where η was the solution viscosity. Concentration: 10 μM; $\lambda_{ex}$: 400 nm.

Addition of isopropanol induced the formation of aggregates and restricted the intramolecular motion (RIM), activating the radiative channel. Similarly, intramolecular motion can also be restricted in a highly viscous condition. As shown in FIGS. 20c and d, the fluorescent enhancement was demonstrated in the water and glycerol mixtures, meaning that process of RIM can be activated in a viscous condition. Table 1 summarizes the photophysical properties of CSPP and shows $\Phi_F$ in different solvent mixtures.

TABLE 1

Photophysical Properties of CSPP

| ASCP-PZ | $\lambda_{max, abs}$ [nm] | $\lambda_{max, em}$ [nm] | $\varphi_F$ [%] |
|---|---|---|---|
| In water | 395 | 640 | 0.9 |
| Aggregates in 99% isopropanol | 400 | 624 | 5.6 |
| In 95% glycerol | 405 | 610 | 13.7 |

Figure 21:
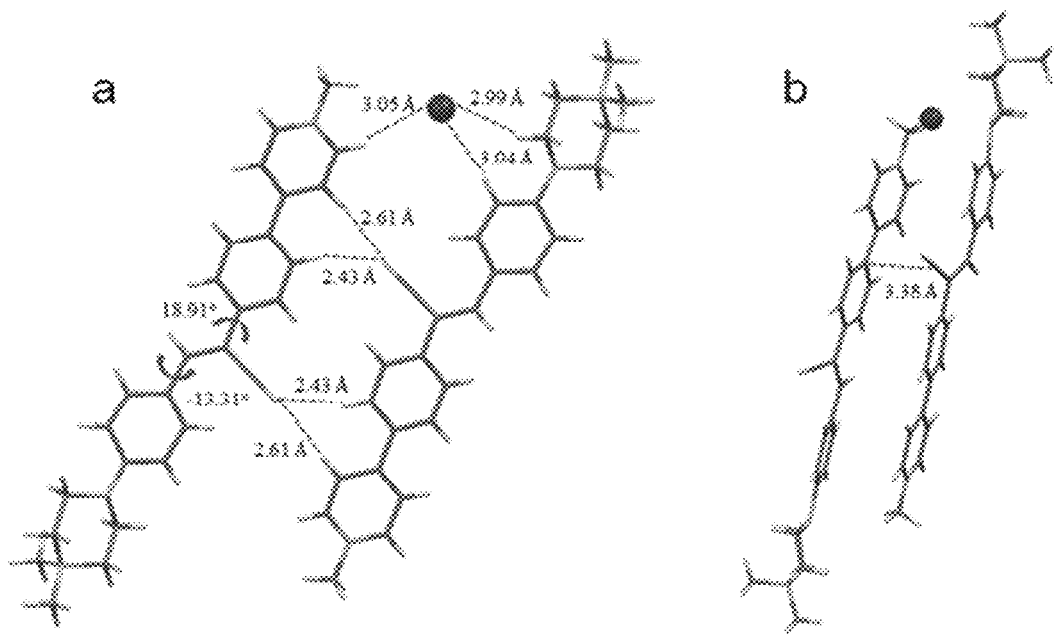
FIG. 21 shows intermolecular (a) C—H . . . N, C—H . . . I and (b) C—C . . . C—N interactions between neighbor molecules.

To further understand the molecular interactions of CSPP in solid state, its single crystal structure (FIG. 21) was studied. It was found that the process of RIM was caused by the C—H . . . N and C—H . . . I intermolecular interactions (FIG. 21a). These restrictions allowed CSPP to stay in a nearly planar arrangement, encouraging π conjugation in order to have a redder absorption and emission. On the other hand, J-aggregate was noticed in the packing of a single crystal (FIG. 21b), avoiding strong π-π stacking like in H-aggregates.

Figure 22:
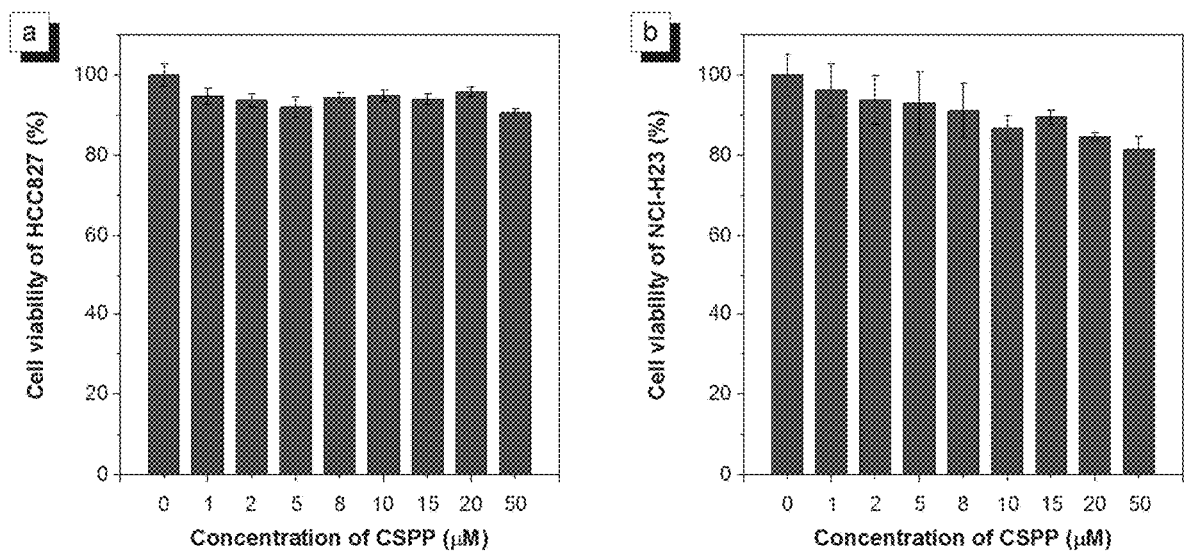
FIG. 22 shows cell viability of HCC827 (a) and NCI-H23 (b) cells incubated in culture medium with different concentrations of CSPP. HCC827 and NCI-H23 cells were seeded for 24 hours and incubated in CSPP of different concentration for 24 hours. Data given are the mean±SD (n=4).

Before CSPP was further functionalized for antibody labeling, its biocompatibility was verified by CCK-8 assay (FIG. 22). The cell viability of HCC827 and NCI-H23 cells were above 90% and 81%, respectively, at CSPP concentrations of up to 50 μM, demonstrating high biocompatibility.

Figure 23:
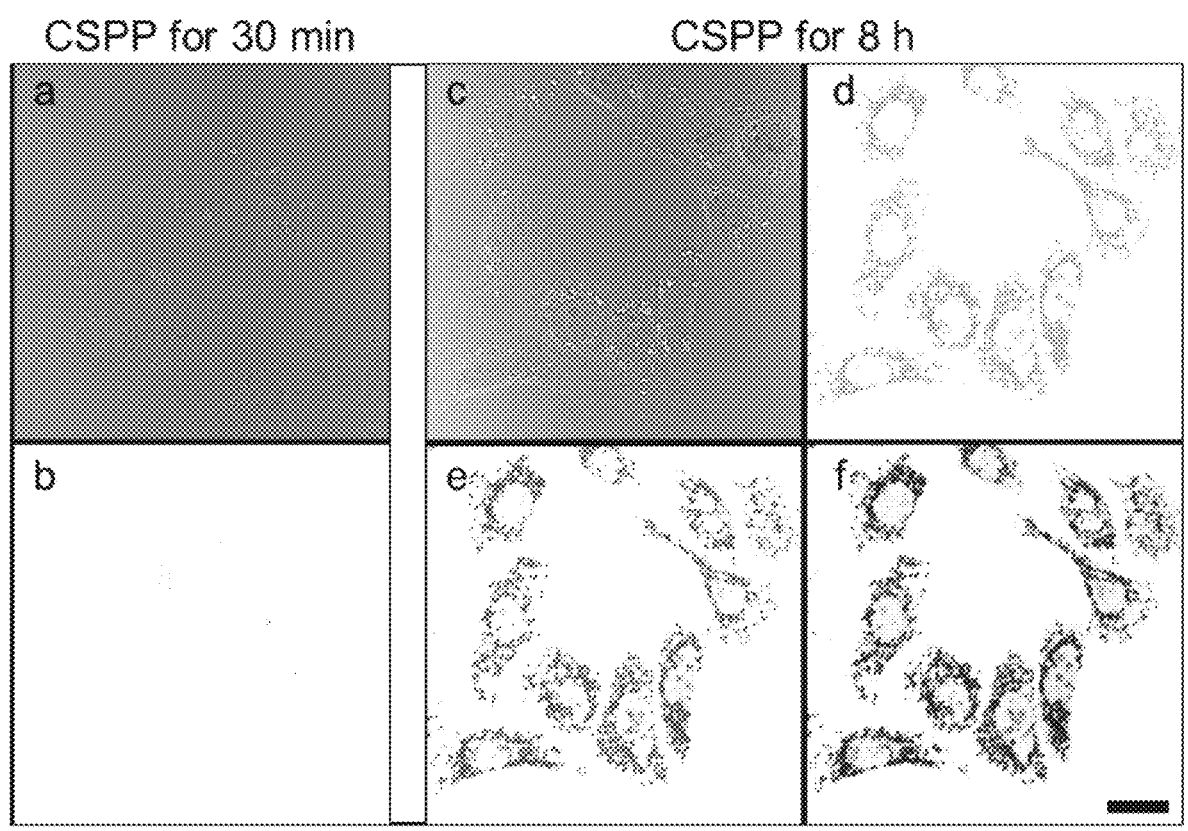
FIG. 23 shows (a) bright-field and (b) fluorescent images of HCC827 cells stained with 5 μM model CSPP for 30 minutes; and (c) bright-field and (d-f) fluorescent images of HCC827 cells stained with 5 μM CSPP (d, red) for 8 hours, then co-stained with MitoTracker Green (e, green), (f) the merged images of (d) and (e). Condition: CSPP: $\lambda_{ex}$=405 nm, $\lambda_{em}$=550-700 nm; MitoTracker Green: $\lambda_{ex}$=488 nm, $\lambda_{em}$=495-535 nm. Scale bars are 20 μm.

The cell imaging of CSPP molecule was also checked (FIG. 23). From the results, no emission from HCC827 cells stained by 5 μM of CSPP was observed in 30 minutes, but the mitochondria lit up after 8 hours. The co-staining experiment with MitoTracker Green showed a good overlap with CSPP with a Pearson correlation coefficient of 0.80. This indicated that the cationic CSPP itself can specifically target mitochondria, which was understandable because CSPP carries two positive charges and thus takes time to pass through the amphilic plasma membrane. After 8 hours of incubation, more dyes entered and accumulated in the mitochondria of the cells due to targeting of the pyridium group.

After studying the properties of CSPP, it was found to be water-soluble, long-wavelength fluorescent, and biocompatible, therefore making it a potential candidate for conjugation with antibodies.

Properties of CSPP—NHS

CSPP—NHS was synthesized by functionalizing CSPP with a N-hydroxysuccinimide (NHS) ester group. NHS is popularly used in bio-conjugation because of its high selectivity to a primary amine in aqueous solution. In the present subject matter, cetuximab, a chimeric anti-EGFR monoclonal antibody approved by the United States Food and Drug Administration (FDA), was used as a model for antibody labeling. EGFR overexpression has been associated with a number of cancers, including squamous-cell carcinoma of the lung (80% of cases), anal cancers, glioblastoma (50%), and epithelial tumors of the head and neck (80-100%). Based on the EGFR-targeting property of cetuximab, image contrast between specific cancer cells and normal cells may be greatly improved.

Figure 24:
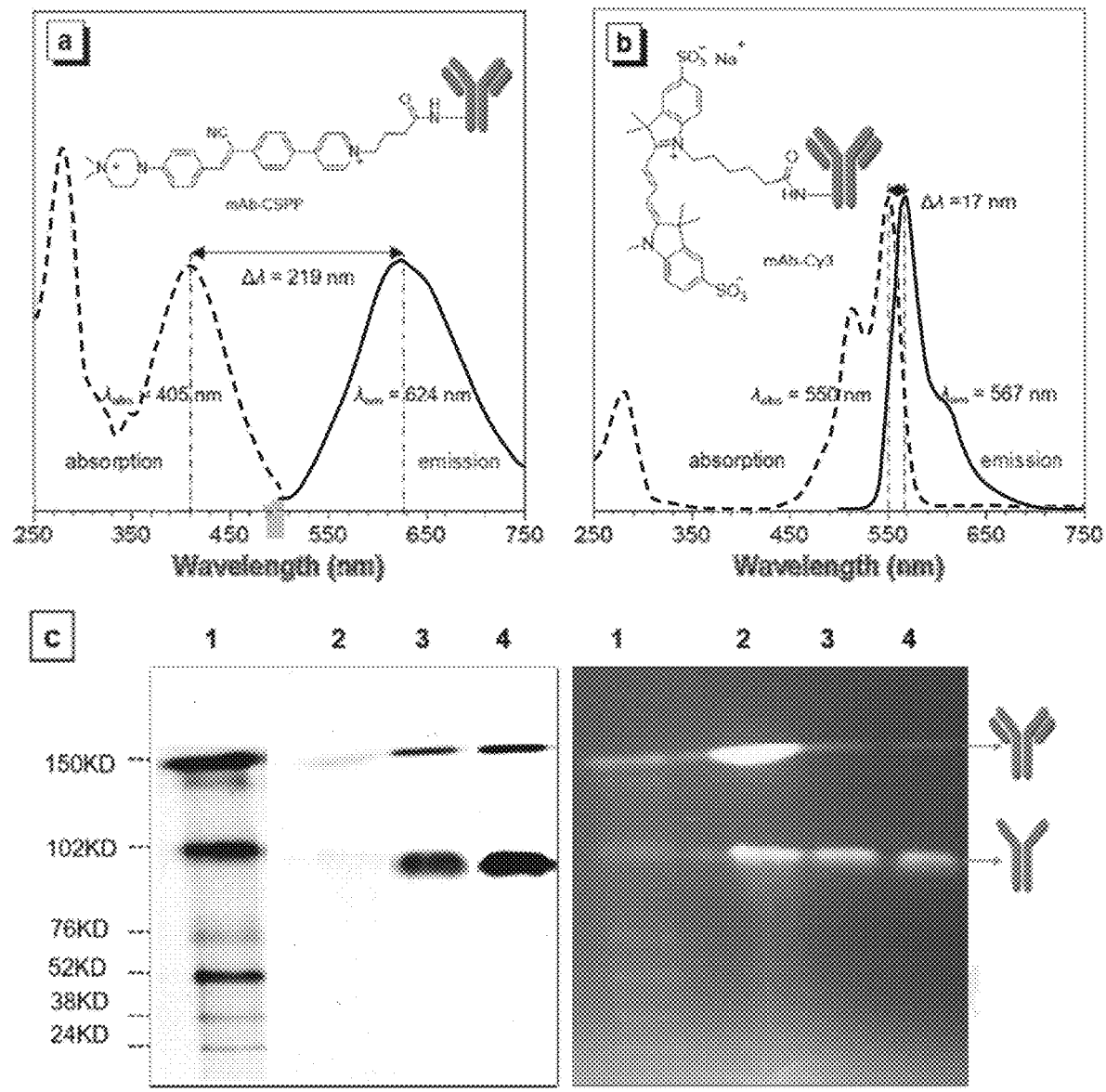
FIG. 24 shows (a and b) Absorption and emission spectra of (a) mAb-CSPP and (b) mAb-Cy3 conjugates. Conjugate concentration: 0.2 mg/mL. (c) SDS-PAGE of monoclonal antibody cetuximab (mAb), mAb-CSPP and mAb-Cy3 conjugates. Left: the protein marker was excited at Cy5 (635 nm) and Cy3 (532 nm) channels, mAb-CSPP was excited by UV channel and the mAb-Cy3 was excited at Cy3 channel. Right: all protein bands were stained with Coomassie blue showing the intact antibody and the partly reduced antibody with two heavy chains left.

CSPP—NHS was successfully conjugated to cetuximab, which was proven by SDS PAGE analysis (FIG. 24c). In FIG. 24b, the CSPP—NHS conjugated antibody (mAb-AIEgen conjugate) and commercial dye conjugated antibody (mAb-Cy3 conjugate) showed clear fluorescence bands corresponding to a naked antibody. Table 2 and FIG. 24a show the properties of mAb-CSPP and mAb-Cy3 conjugates, such as absorption and emission wavelength, Stokes shift, D/P ratio, and molar absorptivity.

TABLE 2

Parameters of mAb-CSPP and mAb-Cy3 conjugates$^a$

|  | D/P | CF@ 280 nm | ε (L mol$^{-1}$ cm$^{-1}$) | $\lambda_{abs}$ (nm) | $\lambda_{em}$ (nm) | Stokes shift (nm) |
|---|---|---|---|---|---|---|
| mAb-CSPP | 3.0 | 0.3 | 26800 | 405 | 624 | 219 |
| mAb-Cy3 | 3.5 | 0.06 | 162000 | 550 | 567 | 17 |

$^a$Abbreviation: D/P = dye/protein molar ratio, CF = correction factor for the fluorophore's contribution to the absorbance at 280 nm, ε = molar absorptivity, $\lambda_{abs}$ = maximum absorption wavelength, $\lambda_{em}$ = maximum emission wavelength.

Figure 25:
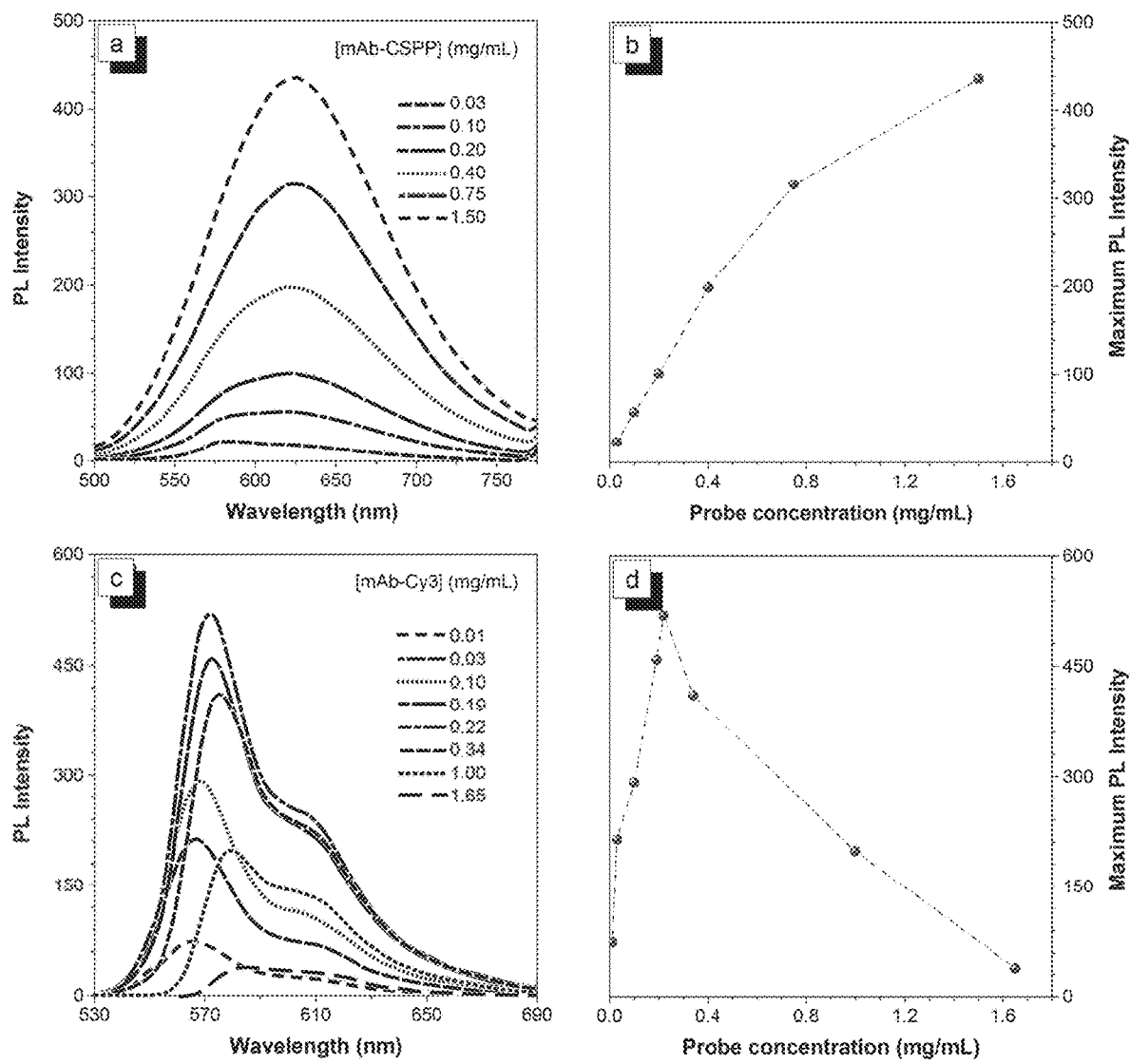
FIG. 25 shows (a and c) PL spectra and (b and d) plots of maximum fluorescence intensity of (a and b) mAb-CSPP and (c and d) mAb-Cy3 conjugates in PBS versus the probe concentration.

Cyanine dyes commonly suffer from the ACQ effect. As such, how the concentration of mAb-dye conjugates affects the fluorescent intensity was investigated. In FIG. 25, the emission intensities of mAb-dye conjugates of different concentrations were recorded. Fluorescence from mAb-Cy3 conjugate became weaker at a high concentration, but fluorescence from mAb-AIEgen conjugate became stronger, revealing the advantages of AIE characteristics. At the same time, it showed that AIE characteristics were kept after bio-conjugation.

The fluorescence of CSPP needed to be activated by high viscosity or a strong electrostatic interaction due to RIM. As such, it has potential to be used for wash-free cell imaging. HCC827 cells (human non-small lung cancer cells with EGFR overexpression) and HEK-293 cells (EGFR-negative human embryonic kidney cells) were used for cell imaging. After 12 hours of incubation, the mAb-AIEgen conjugate showed no fluorescence in normal cells and no background without washing. However, the background was too strong around normal cells by staining with the mAb-Cy3 conjugate (FIG. 26c), demonstrating the possibility of a wash-free labeling capability of the mAb-AIEgen conjugate.

Figure 26:
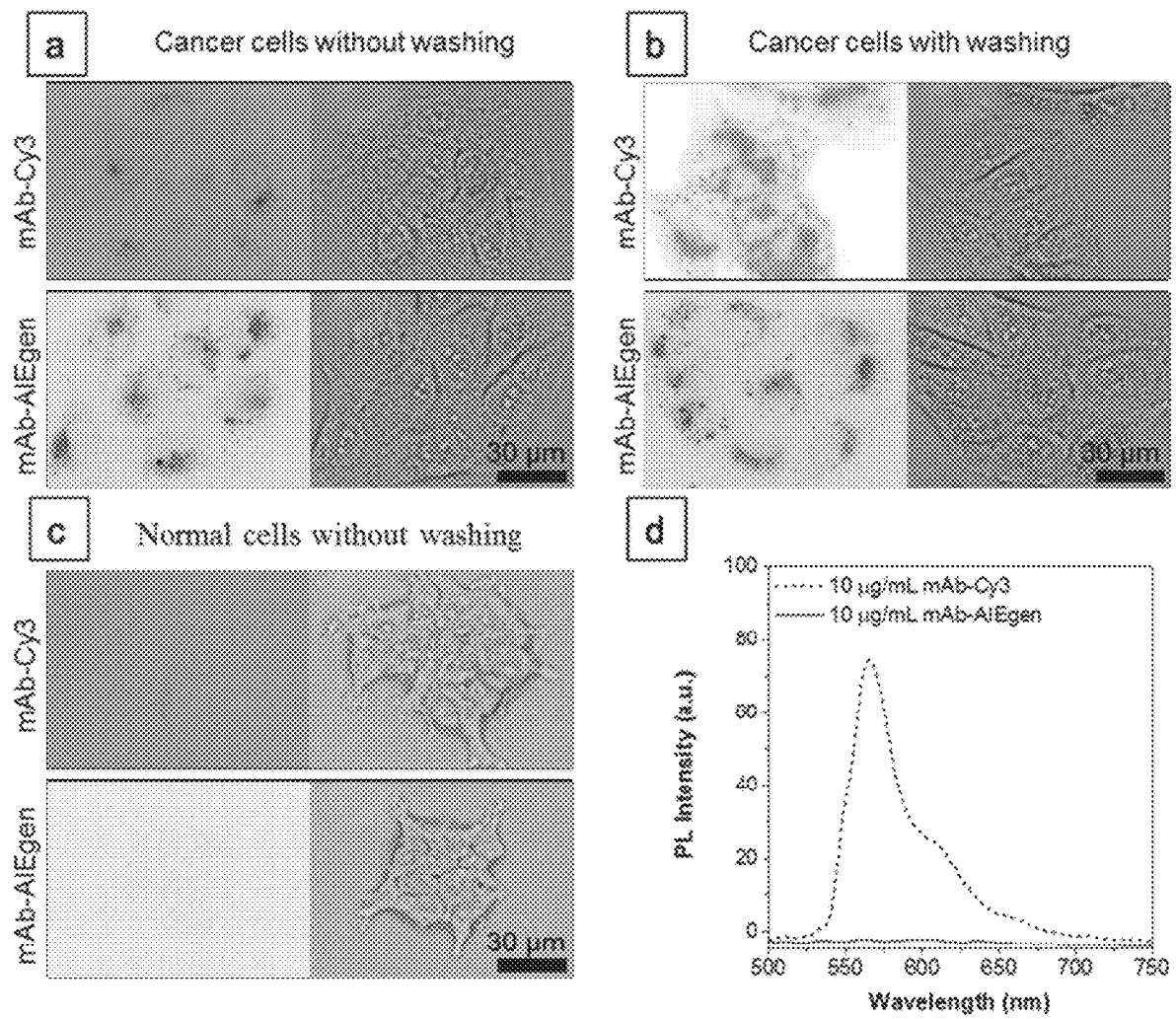
FIG. 26 shows the staining of (a and b) cancer cells (HCC827) and (c) normal cells (HEK-293) with mAb-Cy3 or mAb-AIEgen conjugates (10 μg/mL) without or with washing. Conditions: mAb-Cy3 conjugate: $\lambda_{ex}$=510-550 nm, filter >570 nm; mAb-AIEgen: $\lambda_{ex}$=400-440 nm, filter >455 nm. Exposure time is 1 second for all pictures. Scale bars are 30 μm. (d) PL spectra of mAb-Cy3 conjugate and mAb-AIEgen conjugate; concentration=10 μg/mL; mAb-AIEgen conjugate: $\lambda_{ex}$=405 nm; mAb-Cy3 conjugate: $\lambda_{ex}$=550 nm.

For cancer cells imaging, the cells should be washed after incubation to avoid a strong background by using the mAb-Cy3 conjugates (FIGS. 26a and b). In FIG. 26b, both the mAb-dye conjugates stained the cells clearly with washing, suggesting that the mAb-AIEgen conjugate can be used for wash-free imaging and have higher image contrast between cancer cells and normal cells compared with that of the mAb-Cy3 conjugates without washing. FIG. 26d shows the PL spectra of the mAb-Cy3 conjugate and the mAb-AIEgen conjugate.

Figure 27:
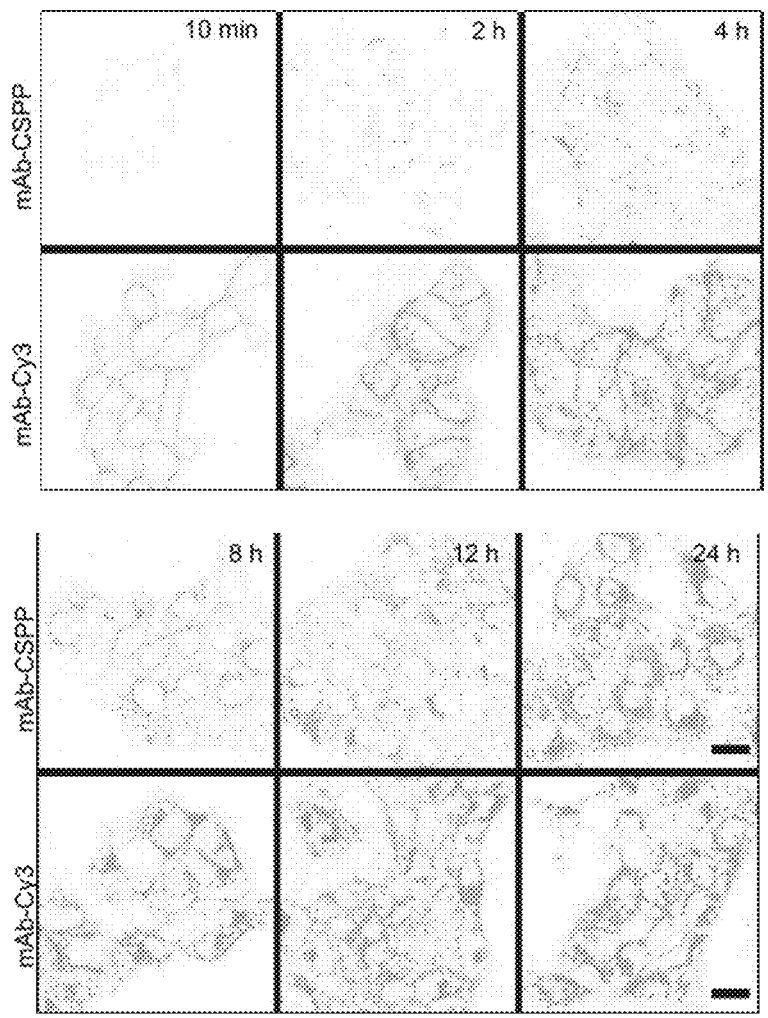
FIG. 27 shows confocal images of HCC827 cells stained with mAb-AIEgen without washing or mAb-Cy3 with washing (10 μg/mL) for 10 minutes, 2 hours, 4 hours, 8 hours, 12 hours, and 24 hours. Condition: mAb-AIEgen: $\lambda_{ex}$=405 nm, $\lambda_{em}$=550-700 nm; mAb-Cy3: $\lambda_{ex}$=560 nm, $\lambda_{em}$=563-700 nm.

To track the "turn-on" process, HCC827 cells were imaged after incubation by the mAb-AIEgen conjugates for different times (FIG. 27). Like many commercial fluorescent probes, the mAb-Cy3 showed strong light emission in the probe medium and required washing with PBS at a selected incubation time before acquiring the LSCM images. Because the washing steps take extra time, measurement of biological processes on a short time scale becomes impossible and thus, the time-based limitation to real-time cell imaging using the mAb-Cy3 was ignored. As shown in FIG. 27, HCC827 cells incubated with the mAb-Cy3 revealed fluorescence only on the cell membrane at the first 10 minutes, and bright fluorescence spots appeared inside the cells after 2 hours, indicating the endosomal-lysosomal uptake of the probe.

Figure 28:
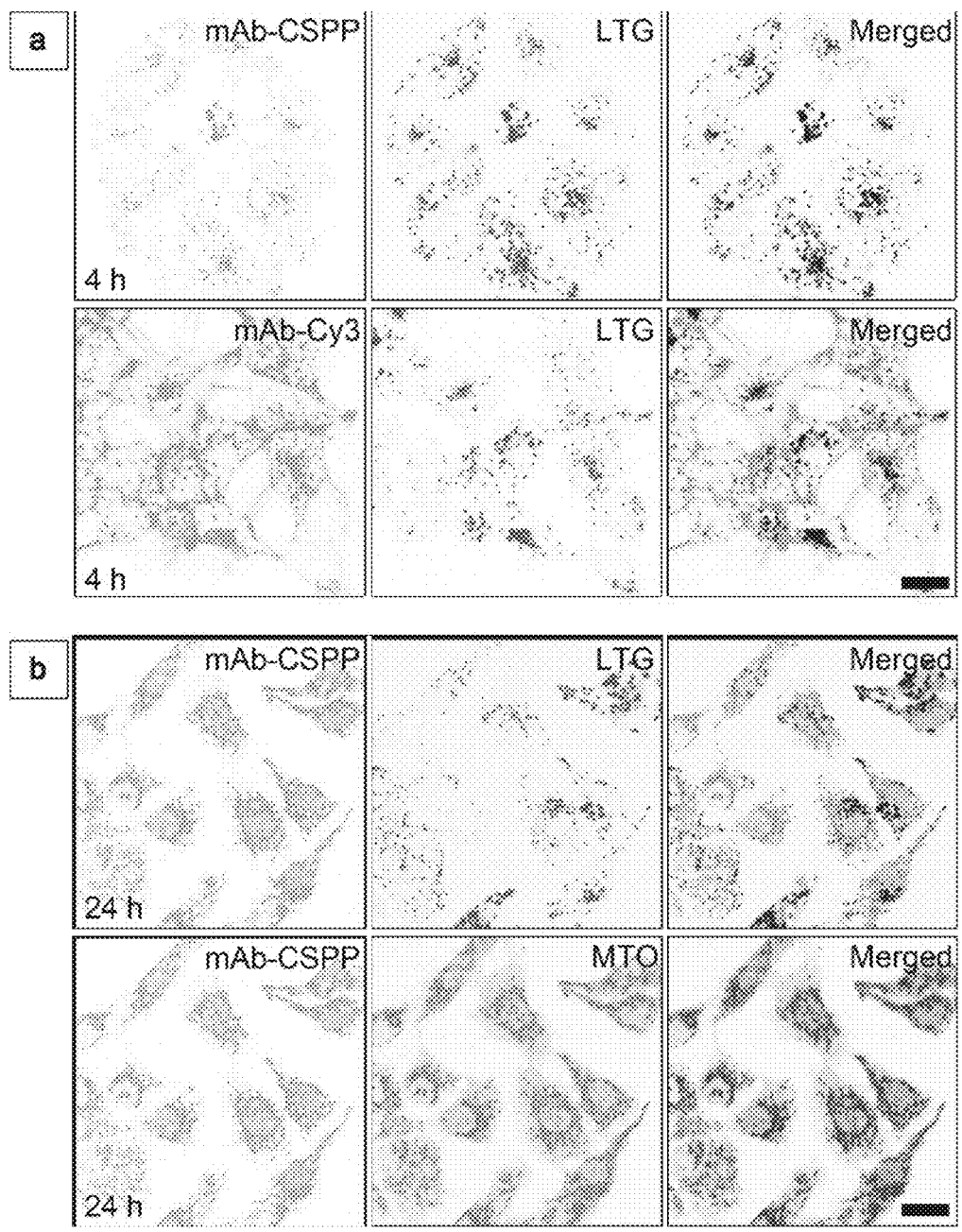
FIG. 28 shows (a) confocal images of HCC827 cells stained with 10 μg/mL of mAb-CSPP or mAb-Cy3 conjugates for 4 hours and then co-stained with LysoTracker Green (LTG) for 5 minutes. (b) Confocal images of HCC827 cells stained with 10 μg/mL of mAb-CSPP for 24 hours, followed by staining with LTG/Mito-Tracker Orange (MTO). Conditions: for mAb-Cy3, $\lambda_{ex}$=560 nm, emission filter=563-700 nm. For mAb-CSPP, $\lambda_{ex}$=405 nm, emission filter=550-700 nm. For LTR, $\lambda_{ex}$=488 nm, emission filter=495-535 nm. For MTO, $\lambda_{ex}$=560 nm, emission filter=565-585 nm. Scale bar: 20 μm.

The mAb-Cy3 showed strong fluorescence both on the cell membrane and inside the cells without spatial distinguishability, as proved by co-staining with LysoTracker Green at 4 hours incubation (FIG. 28a). In contrast, no fluorescence was observed on the cell membrane incubated with the mAb-CSPP at 10 minutes (FIG. 27). After ligand binding and receptor activation, cetuximab, together with EGFR, was slowly endocytosed into early endosome and transferred to lysosomes for degradation. Whereas, after 2 hours incubation, only a few punctuated fluorescent spots were observed inside the cells. The cells became brighter with the incubation time because more mAb-CSPP conjugates were endocytosed. At 4 hours, the fluorescence of the mAb-CSPP co-localized well with LysoTracker Green with a Pearson correlation coefficient of 0.87 (FIG. 28a).

Figure 29:
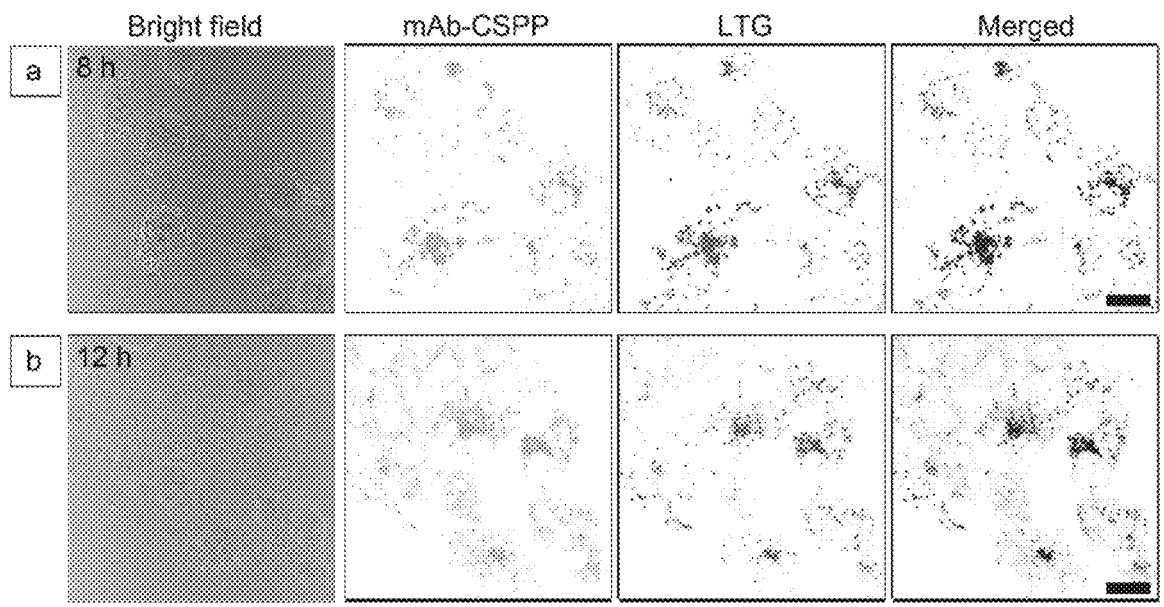
FIG. 29 shows confocal and bright-field images of HCC827 cells incubated with 10 g/mL of mAb-CSPP conjugate for (a) 8 hours and (b) 12 hours, followed by staining with LysoTracker Green (LTG) for 5 minutes. For mAb-CSPP, $\lambda_{ex}$=405 nm, emission filter=550-700 nm. For LTG, $\lambda_{ex}$=488 nm, emission filter=495-535 nm. Scale bar: 20 μm.

However, and surprisingly, the fluorescence of mAb-CSPP existed not only on lysosomes, but also on mitochondria at 24 hours, as revealed by the well co-localization with LysoTracker Green and MitoTracker Orange (FIG. 28b). In particular, mAb-CSPP was mainly located in lysosome at 8 hours, but began to migrate to other organelles at 12 hours, as its fluorescence did not overlap well with LysoTracker Green (FIG. 29). It was inferred that the mAb-CSPP conjugates in lysosome were hydrolyzed due to the harsh environments and turned on the fluorescence inside the lysosome probably through electrostatic interaction between the cationic AIEgens with surrounding biomolecules. Then, the released cationic CSPP catabolites accumulated in mitochondria driven by the high membrane potential of mitochondria.

Interestingly, fluorescence on the cell membrane was undetectable at the beginning of the mAb-AIEgen incubation. To determine whether or not the mAb-CSPP was located on the cell membrane, a set of immunofluorescence experiments were performed and imaged with LSCM. After probe incubation for 25 minutes, the cells were fixed, permeabalized, and blocked. Afterwards, they were incubated with goat F(ab')2 anti-human IgG F(ab')2 (FITC) that could specifically recognize human constant subunits presented on the IgG F(ab')2 of cetuximab.

Figure 30:
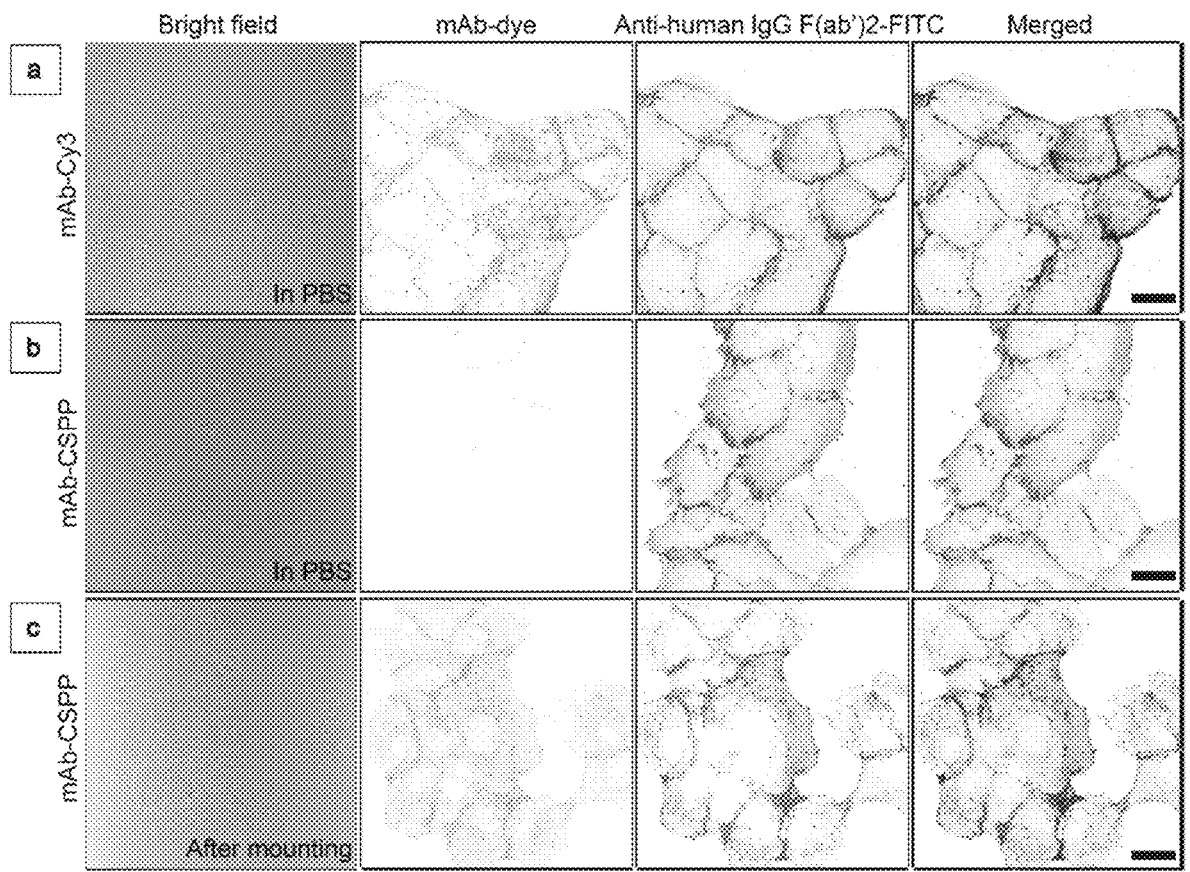
FIG. 30 shows (a) confocal images of HCC827 cells co-stained with mAb-Cy3 and anti-human IgG F(ab')$_2$-FITC taken in PBS; and (b and c) confocal images of HCC827 cells co-stained with mAb-CSPP and anti-human IgG F(ab')$_2$-FITC taken (b) in PBS and (c) after cell mounting with Fluoromount. Conditions: for mAb-Cy3, $\lambda_{ex}$: 560 nm; filter=563-700 nm. For FITC, $\lambda_{ex}$=488 nm, filter=495-535 nm. For mAb-CSPP, $\lambda_{ex}$=405 nm, filter=550-700 nm. Scale bar: 20 μm.

As shown in FIG. 30a, the pseudo green color of goat F(ab')2 was overlaid very well with the pseudo red color of the mAb-Cy3 on the cell membrane. For cells incubated with the mAb-CSPP probe, only the pseudo green color appeared (FIG. 30b), which indicated the mAb-CSPP indeed docked on cell membrane initially, but it was in the dark state. Unexpectedly, the emission of mAb-CSPP on the cell membrane turned on and was co-localized with the pseudo green color of goat F(ab')2 after the cells were mounted with a mounting medium (FIG. 30c).

When cetuximab-CSPP conjugates interacted with EGFR on the cell membrane, the intramolecular motion of CSPP was partially constrained, but was still not enough to give a detectable emission. However, the recognition between the mAb and the receptors did not help much to restrict the intramolecular motion of the AIEgen because the small molecular AIEgen might not necessarily conjugate at the recognition sites of the mAb. Thus, the dye molecule could freely rotate in the aqueous environment. When using a mounting medium to solidify the cell sample (FIG. 30c), the intramolecular motion of CSPP was largely restricted, leading to a high fluorescent emission. From this perspective, it is speculated that any AIEgen capable of labeling proteins may be used in immunocytochemistry, where the fluorescence of the dye molecule will turn on after cell mounting.

Figure 31:
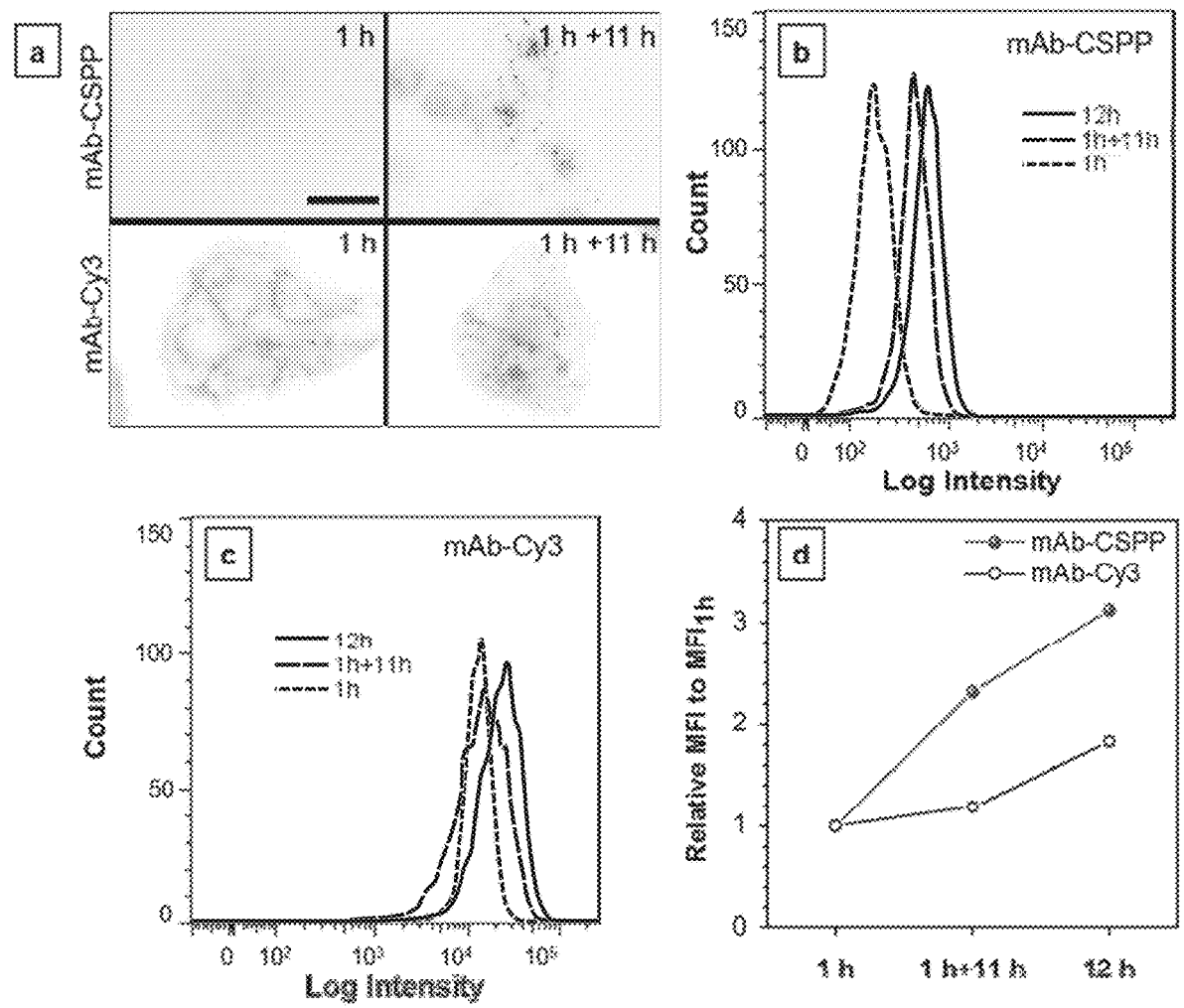
FIG. 31 shows (a) fluorescent images of HCC827 cells incubated with 10 μg/mL of mAb-CSPP and mAb-Cy3 conjugates for 1 hour and the fluorescent images of dye-stained cells followed by washing with PBS and further incubation in fresh medium for 11 hours. Conditions: for mAb-Cy3, $\lambda_{ex}$=510-550 nm, dichroic mirror=570 nm. For mAb-CSPP, $\lambda_{ex}$=400-440 nm, dichroic mirror=455 nm. Exposure time: 2 seconds. Scale bar: 30 μm. (b and c) Flow cytometric analysis of HCC827 cells after incubation with (b) mAb-CSPP and (c) mAb-Cy3 conjugates at different time intervals. Conditions: for mAb-Cy3, $\lambda_{ex}$=561 nm, detection with bandpass filter=583±7.5 nm. For mAb-CSPP, $\lambda_{ex}$=405 nm, detection with band-pass filter=610±10 nm. (d) Plot of relative fluorescent intensity (MFI/MFI$_{1h}$), where MFI$_{1h}$ is the mean fluorescence intensity after probe incubation for 1 hour.

To figure out the reason why fluorescence is turned on inside lysosome, the time-dependent endocytosis of the antibody-dye conjugates into HCC827 cells was investigated. The cell membrane incubated with the mAb-CSPP for 1 hour was non-emissive (FIG. 31a). When the cells were changed into fresh culture medium without the probe to promote the endocytosis of the antibodies on cell membrane, the emission was observed inside the cells after 11 hours (FIG. 31a). For the mAb-CSPP, the mean fluorescence intensity (MFI) increased by 1.4-fold after 11 hours of further incubation, while almost no increase of MFI was observed for the mAb-Cy3, as suggested by the results from flow cytometer (FIGS. 31b, c, and d). Therefore, it was indicated that the receptor-mediated endocytosis turned on the fluorescence.

Figure 32:
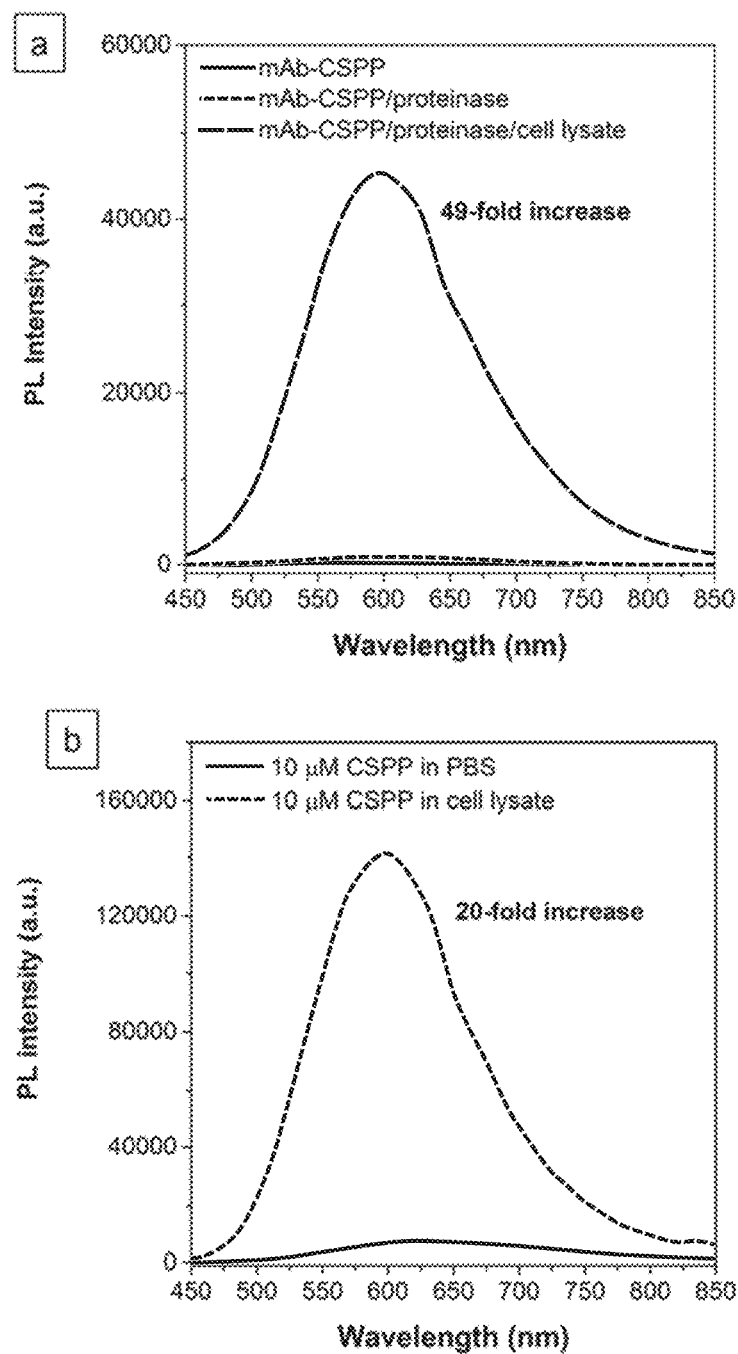
FIG. 32 shows (a) the PL intensity change of digested mAb-CSPP conjugates catalyzed by proteinase K upon addition of cell lysate. The mAb-CSPP conjugates of 0.2 mg/mL were pretreated by 4 M urea and 2 mg/mL proteinase K at 37° C. for 12 hours. Cell lysate was prepared by ultrasonicating HeLa cells of 8×10$^5$ cells/mL in water for 30 minutes. The concentration of mAb-CSPP used for fluorescence measurement was 0.1 mg/mL; and (b) the PL intensity change of CSPP induced by cell lysate.

It was hypothesized that the fluorescence may have been slowly turned on because the antibody degradation inside lysosome controls the fluorescence emission. To prove this, the proteinase K was used to digest the antibody, allowing the release of CSPP residues, which interact with the surrounding environment freely. Results showed that the intact mAb-AIEgen and the mixtures of the degraded mAb-AIEgen with proteinase K emitted very weakly (FIG. 32a). However, the fluorescence increased about 49 times after the addition of cell lysate to simulate the environment of a lysosome (FIG. 32a). Because the cationic CSPP molecule is water-soluble, the great fluorescence increase may be attributed to the electrostatic interactions with biomolecules inside cells (FIG. 32b).

Figure 33:
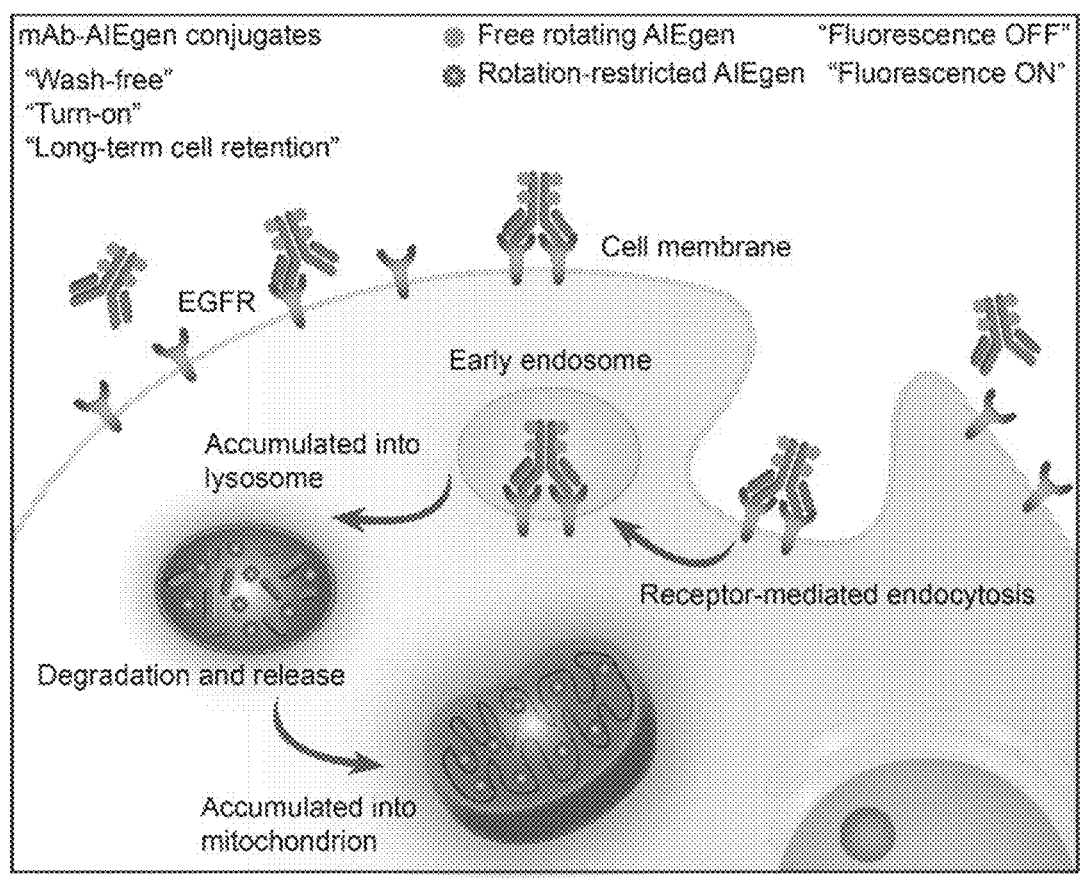
FIG. 33 shows a schematic representation of the "turn-on" process of specific cancer cells by mAb-AIEgen conjugates.

After drawing conclusions from the results of FIGS. 27-32, a working mechanism of the mAb-AIEgen conjugates was proposed (FIG. 33), wherein it was first bound to the EGFR on a cell membrane. At that stage, the fluorescence was silent because CSPP was still under free intramolecular motions. The mAb-AIEgen conjugates were then internalized into cells after binding to EGFR. Then, the mAb-AIEgen conjugates were directed to lysosomes, where the conjugates were digested by lysosomal enzymes. The released cationic AIEgens strongly interacted with surrounding biomolecules through electrostatic interactions, triggering the fluorescence emission due to the restriction of intramolecular rotation of AIEgens. Consequently, the released CSPP slowly diffused out from lysosome and moved to mitochondria, owing to the high affinity of Py to mitochondria.

After understanding the working mechanism of the mAb-AIEgen conjugates, specificity to cancer cells was checked. Cetuximab has been widely applied for targeting non-small cell lung cancer (NSCLC) with overexpressed EGFR.

Figure 34:
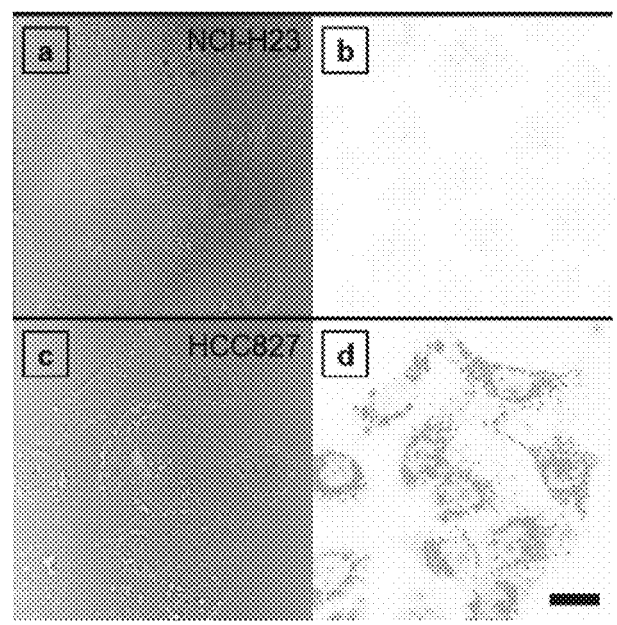
FIG. 34 shows (a and c) bright-field and (b and d) confocal fluorescence images of (a and b) EGFR-negative NCI-H23 cells and (c and d) EGFR-positive HCC827 cells incubated with 10 μg/mL of mAb-CSPP conjugate for 24 hours. $\lambda_{ex}$: 405 nm; emission filter: 550-700 nm; scale bar: 20 μm.

Among different NSCLC cell lines, HCC827 cells have the highest level of EGFR expression, and NCI-H23 cells have the lowest expression. These two cell lines were used to evaluate the bioactivity of mAb-CSPP conjugates which underwent covalent conjugation and several purification processes. As shown in FIG. 34, no fluorescence was detected in NCI-H23 cells after being incubated with mAb-CSPP for 24 hours, while bright fluorescence was observed in HCC827 cells, indicating the good bioactivity and selectivity of mAb-CSPP conjugates.

Figure 35:
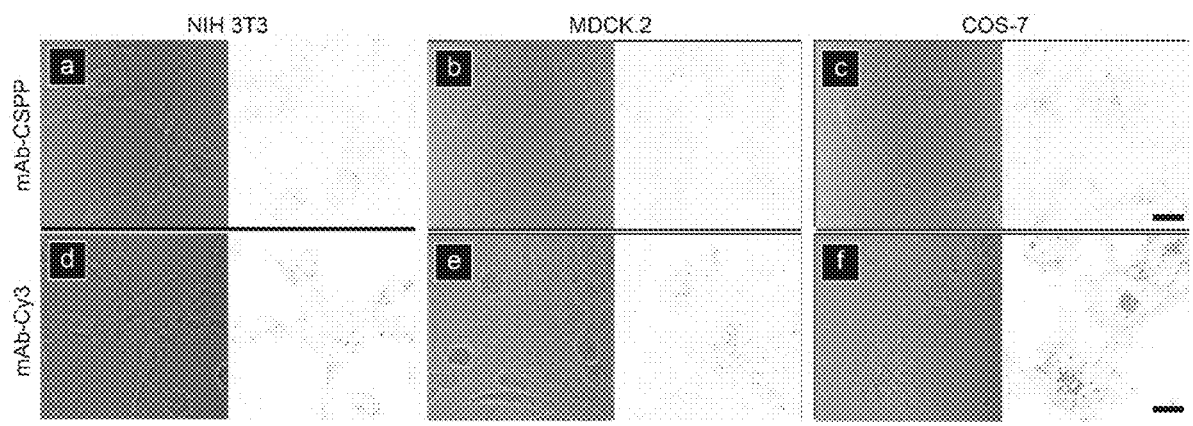
FIG. 35 shows confocal fluorescence and bright-field images of different normal cells (mouse embryo NIH 3T3, *Canis familiaris* kidney MDCK.2, and monkey kidney COS-7) stained with mAb-AIE conjugate or mAb-Cy3 conjugate (10 μg/mL) for 12 hours. Conditions: mAb-AIEgen conjugate: $\lambda_{ex}$=405 nm, $\lambda_{em}$=550-700 nm; mAb-Cy3 conjugate: $\lambda_{ex}$=560 nm, $\lambda_{em}$=563-700 nm. Scale bar: 20 μm.

The background signals from normal cells were also checked. Different normal cells (mouse embryo NIH 3T3, *Canis familiaris* kidney MDCK.2, and monkey kidney COS-7) with different levels of EGFR expression were incubated by mAb-dye conjugates for 12 hours (FIG. 35), and the images were taken after washing. From the results, the mAb-AIEgen conjugates showed almost no fluorescence in the normal cells, but some fluorescent signals were found in normal cells incubated by the mAb-Cy3 conjugates. The difference may be attributed to the "turn-on" property of the mAb-AIEgen conjugates controlled by antibody degradation. Specifically, the mAb-AIEgen conjugates were not emissive on the cell membrane and only showed considerable fluorescence after antibody degradation. However, mAb-Cy3 always showed fluorescence and may also give background signals due to the nonspecific adsorption. The results revealed that the "turn-on" process of antibody-AIEgen conjugates was beneficial to have a higher image contrast than the "always-on" antibody conjugates in order to distinguish between cancer cells and normal cells.

Figure 36:
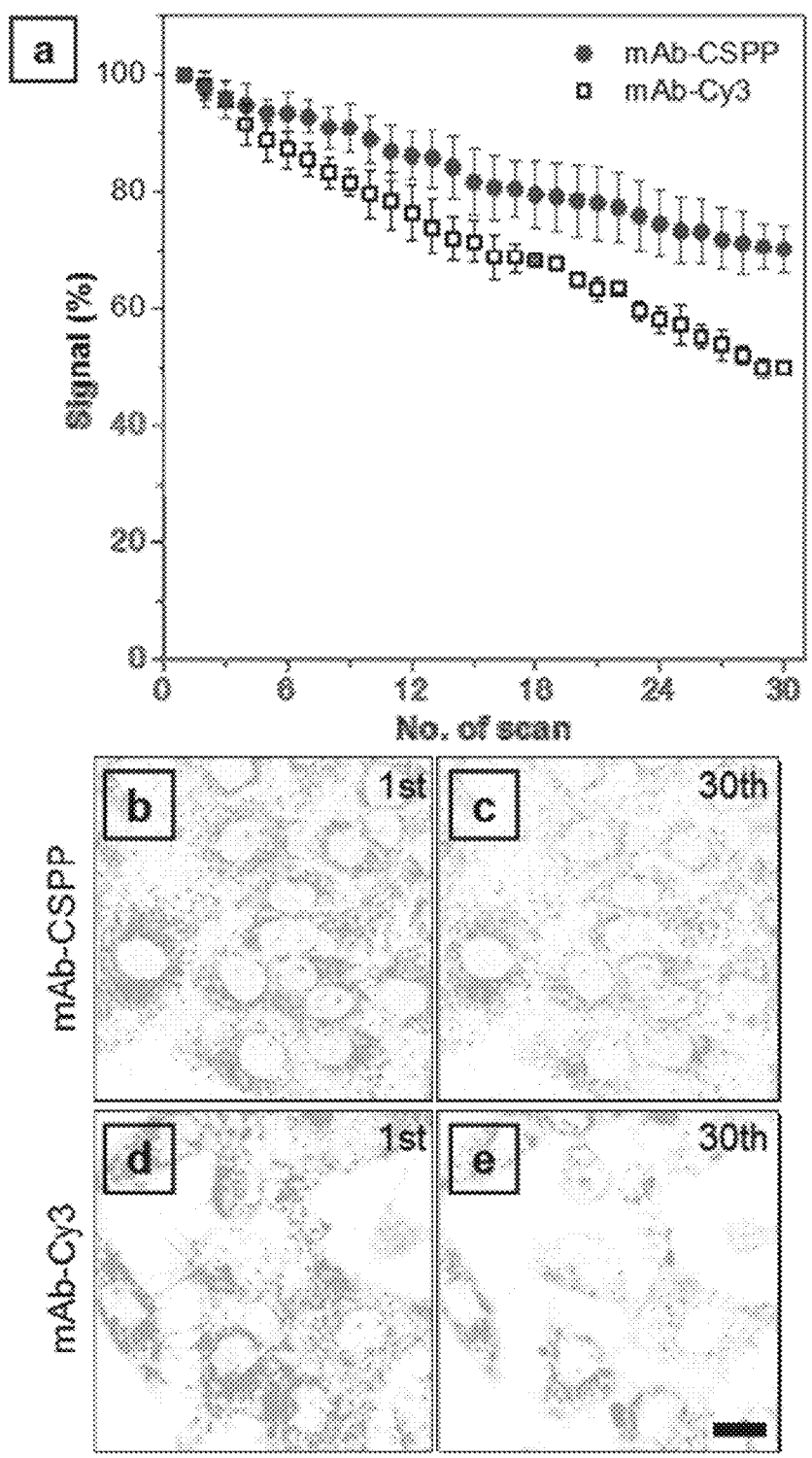
FIG. 36 shows (a) loss in fluorescence signal of (circle) mAb-CSPP- and (blank square) mAb-Cy3-stained HCC827 cells after continuous scanning using LSCM. Data are the mean±SD (n=4). (b-e) LSCM images of HCC827 cells stained with (b and c) mAb-CSPP and (d and e) mAb-Cy3 conjugates at the 1st and 30th scans. Concentration: 10 μg/mL; laser power: 32 μW; scale bar: 20 μm. For mAb-CSPP: $\lambda_{ex}$=405 nm; emission filter=550-700 nm. For mAb-Cy3: $\lambda_{ex}$=560 nm, emission filter=563-700 nm.

Photostability is a pivotal parameter for fluorescence imaging. The photostability of the mAb-AIEgen conjugate and the mAb-Cy3 conjugate were investigated and compared. They were continuously scanned by their corresponding excitation, and the mAb-AIEgen conjugate was found to be more photostable than the mAb-Cy3 conjugate, demonstrating the potential of long-term tracking (FIG. 36).

Figure 37:
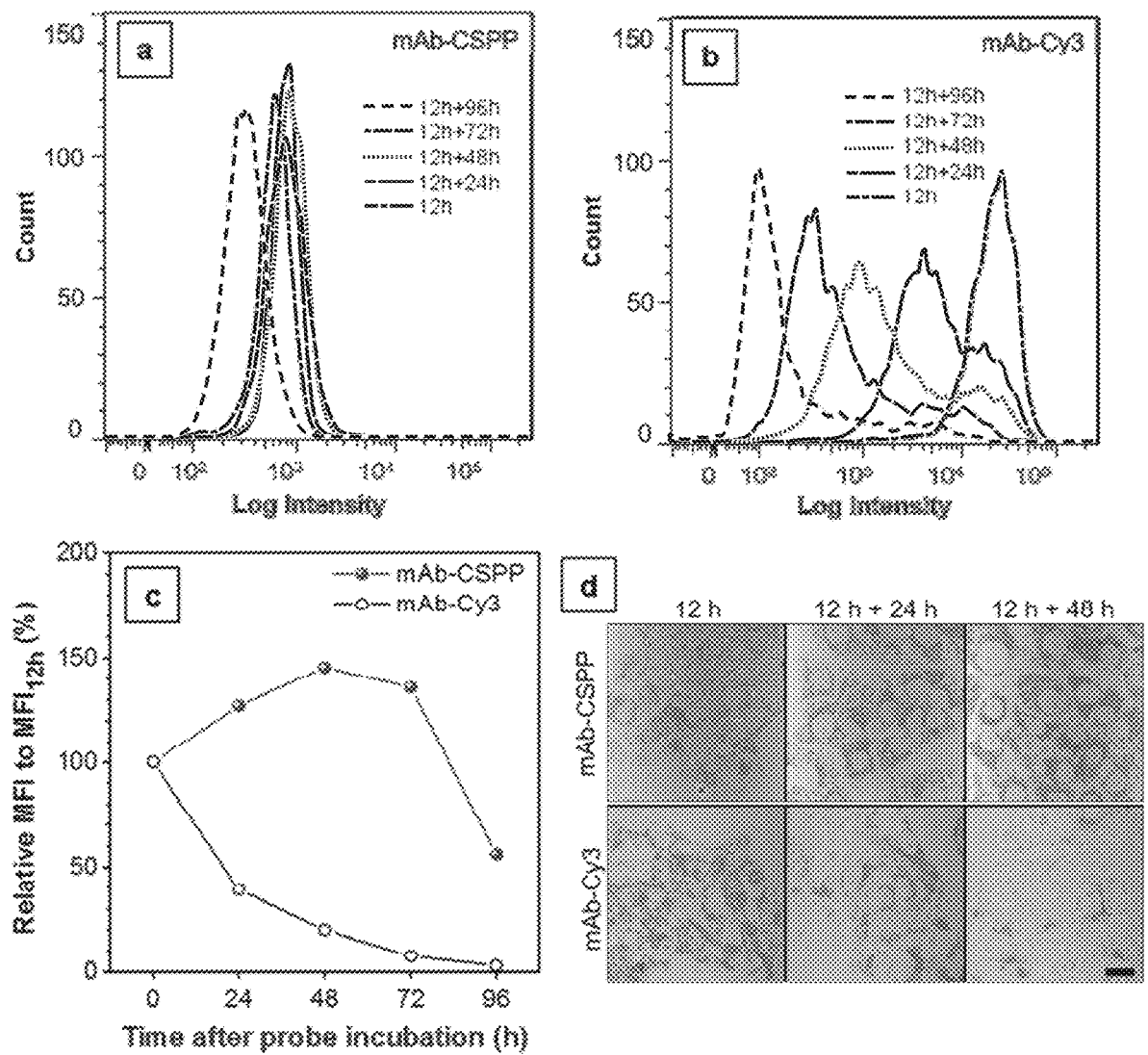
FIG. 37 shows (a and b) flow cytometric analysis of HCC827 cancer cells incubated with 10 μg/mL of (a) mAb-CSPP and (b) mAb-Cy3 at different time intervals. (c) A plot of relative fluorescent intensity (MFI/MFI$_{12h}$), where MFI$_{12h}$ is the mean fluorescence intensity at 12 hours incubation. Conditions: for mAb-Cy3, $\lambda_{ex}$=561 nm, detection with bandpass filter of 583±7.5 nm. For CSPP, $\lambda_{ex}$=405 nm, detection with band-pass filter of 610±10 nm. (d) The merged confocal images of the bright field and fluorescent images of cells incubated with mAb-dye conjugates for 12 hours, and cells further incubated in fresh medium for 24 and 48 hours. Conditions: for mAb-Cy3, $\lambda_{ex}$=560 nm, emission filter=563-700 nm. For mAb-CSPP, $\lambda_{ex}$=405 nm, emission filter=550-700 nm. Scale bar: 20 μm.

Apart from photostability, biostability of a fluorescent probe is a pivotal requirement for in vitro and in vivo long-term imaging application. Once the fluorophore is conjugated to an antibody, the fluorescence may be compromised by catabolism. To assess the biostability of the mAb-dye conjugates, HCC827 cells were first incubated with the antibody conjugates for 12 hours and then with fresh culture medium for a required time. Afterwards, they were subjected to analysis by flow cytometer (FIGS. 37*a* and 18*b*) and LSCM (FIG. 37*d*) every 24 hours. The results from flow cytometry showed that the MFI of cells incubated with mAb-Cy3 rapidly decreased with time (FIG. 37*c*). Compared with the MFI at 12 hours, the relative values for cells cultured for further 24, 48, 72, and 96 hours were 39%, 20%, 7.4%, and 2.7%, respectively. In contrast, the MFI of cells incubated with the mAb-CSPP increased to its maximum value at 48 hours with a relative MFI of 146% (FIG. 37*c*).

EGFR downregulation activated by cetuximab is very slow and was only apparent after 24 hours (60% EGFR remain on cell membrane). When the time was prolonged from 24 hours to 96 hours, more activated EGFR would thus be internalized and degraded. It was plausible that the fluorescence increase for cells incubated with mAb-CSPP was attributed to the receptor-mediated endocytosis into the lysosome and the accumulation of CSPP catabolites in mitochondria after the probe degradation. The fluorescence decreased at 72 hours and down to a relative MFI of 56% at 96 hours, probably due to the diminishment of dye molecules in each cell by cell proliferation.

Additionally, the fluorescence enhancement was also revealed in the LSCM images of cells incubated with mAb-CSPP at both day 1 (12 hours+24 hours) and day 2 (12 hours+48 hours) (FIG. 37*d*). In contrast, fluorescence of cells incubated with the mAb-Cy3 reduced largely (FIG. 37*d*) due to the fast diffusion from the cells after the probe degradation. Thus, the mAb-CSPP not only possesses the capability of long-term cell retention, attributing to the accumulation of CSPP residues in mitochondria after catabolism, but its fluorescence can be further enhanced because of the continuous endocytosis and degradation and the strong restriction of intramolecular rotation of CSPP in mitochondria. In contrast, the mAb-Cy3 showed very short cell retention characteristics due to the rapid cell leakage.

Based on the above findings, a synthetic route for developing other water-soluble AIEgens with properties of generating reactive oxygen species or near-infrared emission was developed. The synthetic route of the new dyes is:

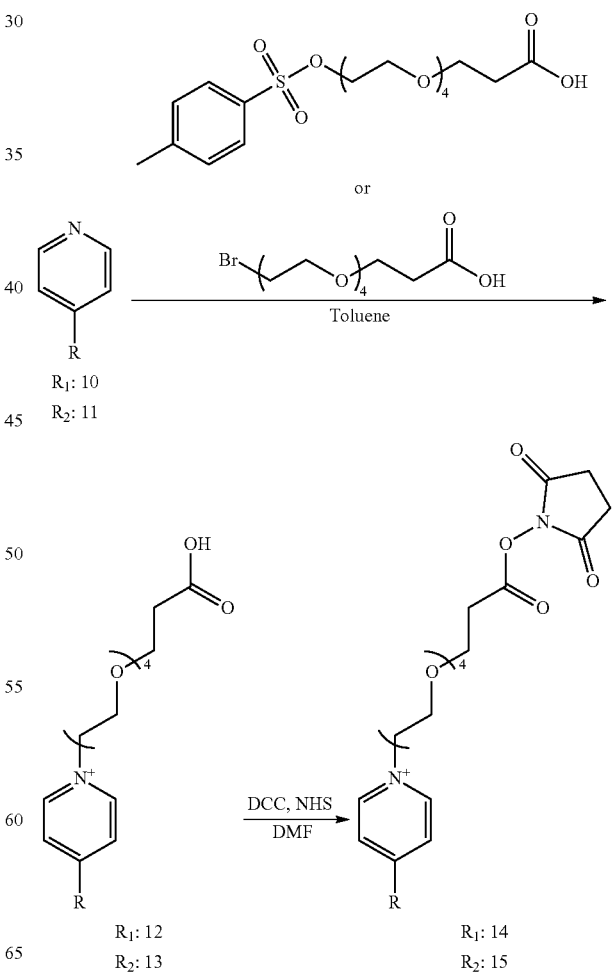

R₁:
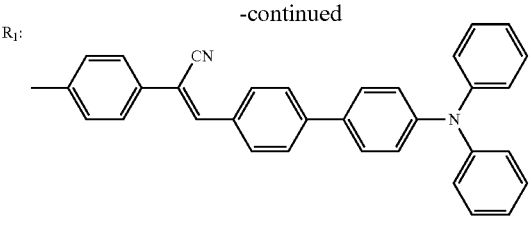

R₂:
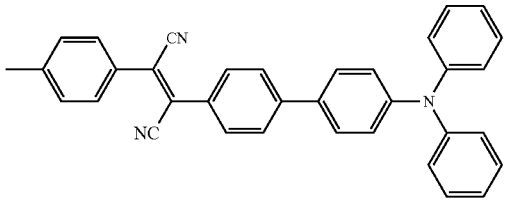

Figure 38A:
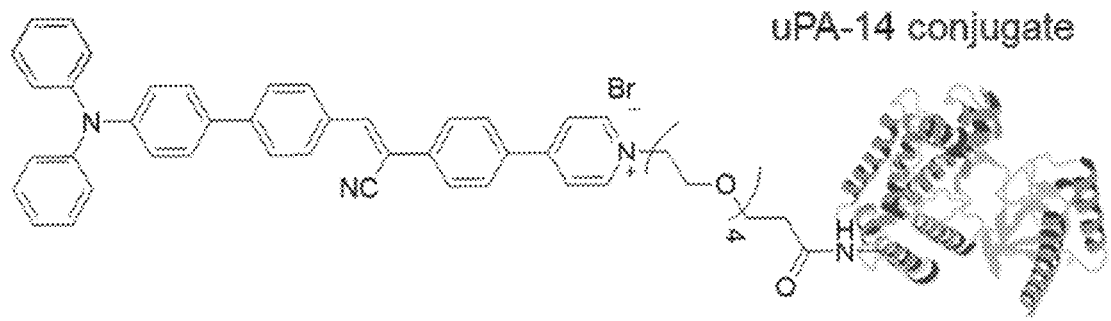
FIG. 38 shows (A) the scheme structure of uPA-14 conjugates; and (B) the fluorescence emission of uPA-14 conjugates, 14 in PBS, and the aggregates of 12 acquired in ethyl acetate. The weak emission of uPA-14 conjugates indicates their potential application in "turn-on" fluorescence imaging.
Figure 38B:
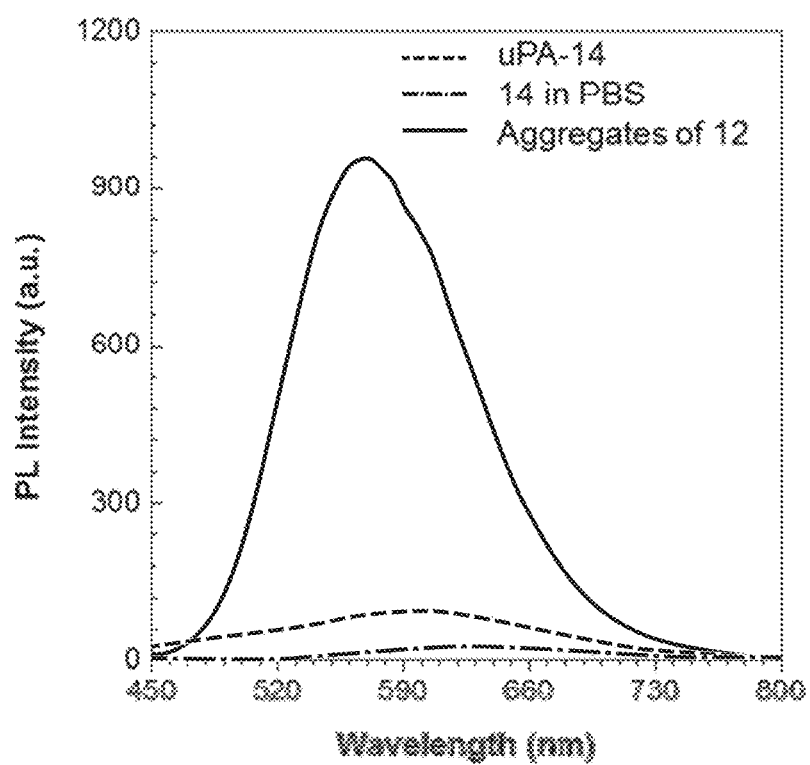

The resulting AIEgens may be used for antibody-targeted photodynamic therapy, as a non-limiting example. Furthermore, the strategy of preparing "turn-on" protein-AIEgen probes may extend to other AIEgens and other proteins. Preliminary results of the PL intensity of AIEgen-conjugated urokinase-type plasminogen activator (uPA) are shown in FIG. 38A-B, wherein the weak emission of uPA-14 conjugates indicates potential application in "turn-on" fluorescence imaging.

With the information contained herein, various departures from precise descriptions of the present subject matter will be readily apparent to those skilled in the art to which the present subject matter pertains, without departing from the spirit and the scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter which are obvious to those skilled in chemistry, biochemistry, or related fields are intended to be within the scope of the following claims.

We claim:

1. An AIEgen comprising a compound selected from the group consisting of:

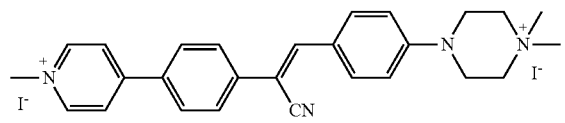

and

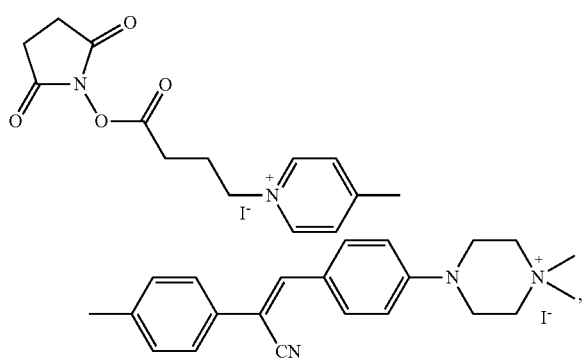

wherein the AIEgen exhibits aggregation induced emission.

2. The AIEgen of claim 1, wherein the AIEgen is used for turn-on imaging and wash-free imaging.

3. The AIEgen of claim 1, wherein the AIEgen is used for long-term cellular retention.

4. The AIEgen of claim 1, wherein the AIEgen is used to target mitochondria.

5. The AIEgen of claim 1, wherein the AIEgen is used as a probe for antibody labeling.

* * * * *

UNITED STATES PATENT AND TRADEMARK OFFICE
CERTIFICATE OF CORRECTION

PATENT NO. : 11,578,265 B2  
APPLICATION NO. : 16/319436  
DATED : February 14, 2023  
INVENTOR(S) : Benzhong Tang et al.

Page 1 of 1

It is certified that error appears in the above-identified patent and that said Letters Patent is hereby corrected as shown below:

In the Claims

Claim 1, Column 46, Line 2, please remove the word "A1Egen" and replace with "AIEgen".
Claim 1, Column 46, Line 30, please remove the word "A1Egen" and replace with "AIEgen".
Claim 2, Column 46, Line 32, please remove the word "A1Egen" and replace with "AIEgen".
Claim 3, Column 46, Line 34, please remove the word "A1Egen" and replace with "AIEgen".
Claim 4, Column 46, Line 36, please remove the word "A1Egen" and replace with "AIEgen".
Claim 5, Column 46, Line 38, please remove the word "A1Egen" and replace with "AIEgen".

Signed and Sealed this  
Twenty-eighth Day of March, 2023

Katherine Kelly Vidal  
*Director of the United States Patent and Trademark Office*